US008158625B2

(12) United States Patent
Castanedo et al.

(10) Patent No.: US 8,158,625 B2
(45) Date of Patent: Apr. 17, 2012

(54) BICYCLIC INDOLE-PYRIMIDINE PI3K INHIBITOR COMPOUNDS SELECTIVE FOR P110 DELTA, AND METHODS OF USE

(75) Inventors: Georgette Castanedo, Redwood City, CA (US); David Goldstein, Nutley, NJ (US); Rama Kondru, Nutley, NJ (US); Matthew Lucas, Nutley, NJ (US); Wylie Palmer, Nutley, NJ (US); Stephen Price, Harlow (GB); Brian Safina, Redwood City, CA (US); Pascal Pierre Alexandre Savy, Harlow (GB); Eileen Mary Seward, Harlow (GB); Daniel P. Sutherlin, Burlingame, CA (US); Zachary K. Sweeney, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/787,608

(22) Filed: May 26, 2010

(65) Prior Publication Data

US 2010/0305084 A1    Dec. 2, 2010

Related U.S. Application Data

(60) Provisional application No. 61/181,458, filed on May 27, 2009.

(51) Int. Cl.
*A61K 31/535* (2006.01)
*C07D 413/14* (2006.01)

(52) U.S. Cl. ..................... 514/234.2; 544/117
(58) Field of Classification Search .............. 544/117; 514/234.2
See application file for complete search history.

(56) References Cited

U.S. PATENT DOCUMENTS

| 3,475,429 | A | 10/1969 | Woitun et al. |
| 3,661,908 | A | 5/1972 | Woitun et al. |
| 3,763,156 | A | 10/1973 | Woitun et al. |
| 3,838,121 | A | 9/1974 | Woitun et al. |
| 3,850,917 | A | 11/1974 | Mueller et al. |
| 3,888,851 | A | 6/1975 | Narr et al. |
| 4,007,187 | A | 2/1977 | Fauran et al. |
| 4,146,716 | A | 3/1979 | Cox et al. |
| 4,196,207 | A | 4/1980 | Webber et al. |
| 5,075,305 | A | 12/1991 | Hobbs et al. |
| 6,187,777 | B1 | 2/2001 | Norman et al. |
| 6,492,383 | B1 | 12/2002 | Munchhof et al. |
| 6,608,056 | B1 | 8/2003 | Hayakawa et al. |
| 7,750,002 | B2 | 7/2010 | Shuttleworth et al. |
| 7,776,856 | B2 | 8/2010 | Shuttleworth et al. |
| 7,781,433 | B2 | 8/2010 | Chuckowree et al. |
| 2006/0229306 | A1 | 10/2006 | Terricabras Belart et al. |
| 2007/0185139 | A1 | 8/2007 | Binnun et al. |
| 2007/0249587 | A1 | 10/2007 | Yonetoku et al. |
| 2008/0039459 | A1 | 2/2008 | Folkes et al. |
| 2008/0076758 | A1 | 3/2008 | Folkes et al. |
| 2008/0207609 | A1 | 8/2008 | Shuttleworth et al. |
| 2008/0242665 | A1 | 10/2008 | Bayliss et al. |
| 2008/0269210 | A1 | 10/2008 | Castanedo et al. |
| 2009/0118275 | A1 | 5/2009 | Castanedo et al. |
| 2009/0318411 | A1 | 12/2009 | Castanedo et al. |

FOREIGN PATENT DOCUMENTS

| WO | WO 2006/046035 A1 * | 5/2006 |
| WO | 2006/114606 | 11/2006 |
| WO | 2007/122410 | 11/2007 |
| WO | 2007/127183 | 11/2007 |
| WO | 2007/129161 | 11/2007 |
| WO | 2007/132171 | 11/2007 |
| WO | 2008/152390 | 12/2008 |
| WO | 2008/152394 | 12/2008 |
| WO | 2009/042607 | 4/2009 |
| WO | 2009/053715 | 4/2009 |
| WO | 2009/053716 | 4/2009 |

OTHER PUBLICATIONS

Cancer and Metastasis Reviews (1998), 17(1), 91-106.*
Science (1999), vol. 286, 531-537.*
Cecil Textbook of Medicine, 20th edition (1996), vol. 2, pp. 2050-2057.*
Cecil Textbook of Medicine, 20th edition (1996), vol. 2, pp. 1992-1996.*

(Continued)

*Primary Examiner* — Rebecca Anderson
(74) *Attorney, Agent, or Firm* — Alex Andrus

(57) ABSTRACT

Formula I (Ia and Ib) compounds wherein (i) $X^1$ is N and $X^2$ is S, (ii) $X^1$ is $CR^7$ and $X^2$ is S, (iii) $X^1$ is N and $X^2$ is $NR^2$, (iv) $X^1$ is $CR^7$ and $X^2$ is O, or (v) $X^1$ is $CR^7$ and $X^2$ is $NR^2$, including stereoisomers, tautomers, metabolites and pharmaceutically acceptable salts thereof, are useful for inhibiting the delta isoform of PI3K, and for treating disorders mediated by lipid kinases such as inflammation, immunological, and cancer. Methods of using compounds of Formula I for in vitro, in situ, and in vivo diagnosis, prevention or treatment of such disorders in mammalian cells, or associated pathological conditions, are disclosed.

7 Claims, No Drawings

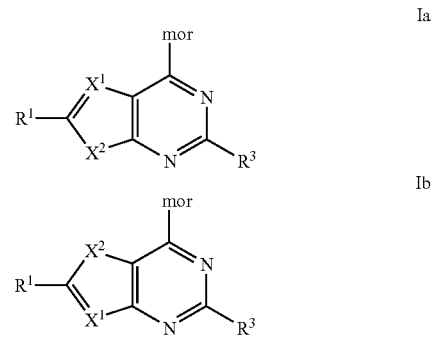

OTHER PUBLICATIONS

FDA mulls drug to slow late-stage Alzheimer's [online], [retrieved on Sep. 23, 2003]. Retrieved from the Internet, URL;http://www.cnn.com/2003/HEALTH/conditions/09/24/alzheimers.drug.ap/index.html>.*

Huff, Joel R., "HIV Protease: A Novel Chemotherapeutic Target for AIDS," Journal of Medicinal Chemistry, vol. 34, No. 8, Aug. 1991, pp. 2305-2314.*

Bourguinon et al., "Synthesis of 2- and 4-substituted thieno[2,3-d]pyrimidines II" *Bulletin de la Societe Chimique de France* 11-12:2483-2487 (1975).

Bourguinon et al., "Synthesis of thieno[2,3-d]pyrimidines substituted at 2 and 4" *Bulletin de la Societe Chimique de France* 3-4(pt 2):815-819 (1975).

Briel at al., "Selective Nucleophilic Replacement of the Benzylsulfanyl Group in 2,4-Disulfanyl-substituted Thieno[2,3-d]pyrimidin-6-carboxylic Acid Derivatives by Secondary Amines" *Journal Heterocyclic Chem*. 42(5):841-846 (Jul.-Aug. 2005).

Brian Safina, "Discovery of Potent and Highly Selective PI3K-Kinase Delta Inhibitors: Taming Time-dependent Inhibition" Slides 242nd ACS National Meeting, Denver, CO, (Aug. 28, 2011).

* cited by examiner

BICYCLIC INDOLE-PYRIMIDINE PI3K INHIBITOR COMPOUNDS SELECTIVE FOR P110 DELTA, AND METHODS OF USE

CROSS REFERENCE TO RELATED APPLICATIONS

This non-provisional application filed under 37 CFR §1.53(b), claims the benefit under 35 USC §119(e) of U.S. Provisional Application Ser. No. 61/181,458 filed on 27 May 2009, which is incorporated by reference in entirety.

FIELD OF THE INVENTION

The invention relates generally to compounds for treating disorders mediated by lipid kinases such as inflammation, immunological, and cancer, and more specifically to compounds which inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol (PI), a phospholipid found in cell membranes, plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

Phosphoinositide 3-kinases (PI3K) are lipid kinases that phosphorylate lipids at the 3-hydroxyl residue of the inositol ring of phosphoinositols (Whitman et al (1988) Nature, 332: 664). The 3'-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

PI3 kinase is a heterodimer consisting of p85 and p110 subunits (Otsu et al (1991) Cell 65:91-104; Hiles et al (1992) Cell 70:419-29). Four distinct Class I PI3Ks have been identified, designated PI3K α (alpha), β (beta), δ (delta), and γ (gamma), each consisting of a distinct 110 kDa catalytic subunit and a regulatory subunit. More specifically, three of the catalytic subunits, i.e., p110 alpha, p110 beta and p110 delta, each interact with the same regulatory subunit, p85; whereas p110 gamma interacts with a distinct regulatory subunit, p101. The patterns of expression of each of these PI3Ks in human cells and tissues are also distinct.

The p110 delta isoform has been implicated in biological functions related to immune-inflammatory diseases, including signaling from the B-cell receptor, T cell receptor, FcR signaling of mast cells and monocyte/macrophage, and osteoclast function/RANKL signaling (Deane J and Fruman D A (2004) Annu Rev. Immunol. 2004. 22:563-98; Janas et al., The Journal of Immunology, 2008, 180: 739-746; Marone R et al., Biochim. Biophy. Acta 2007, 1784:159-185. Deletion of the PI3K delta gene or selective introduction of a catalytically inactive mutant of PI3K delta causes a nearly complete ablation of B cell proliferation and signaling, and impairment of signaling through T cells as well.

SUMMARY OF THE INVENTION

The invention relates generally to Formula I compounds with PI3 kinase inhibitory activity and selective binding to the p110 delta isoform relative to binding to the p110 alpha isoform. Formula I compounds are at least 10 fold selective in binding to the p110 delta isoform relative to binding to the p110 alpha isoform.

Formula I compounds have the structures Ia and Ib:

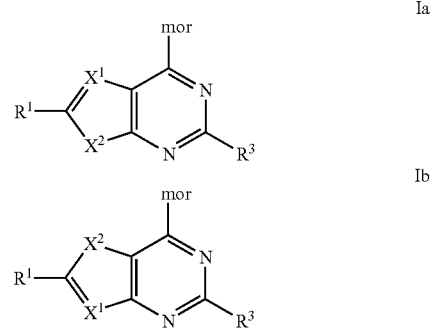

including stereoisomers, tautomers, or pharmaceutically acceptable salts thereof. The various substituents are as defined herein.

Another aspect of the invention provides a pharmaceutical composition comprising a Formula I compound and a pharmaceutically acceptable carrier, glidant, diluent, or excipient.

Another aspect of the invention provides the use of a Formula I compound in the manufacture of a medicament for treating a disease or disorder selected from immune disorders, cancer, cardiovascular disease, viral infection, inflammation, metabolism/endocrine function disorders and neurological disorders, and mediated by the p110 delta isoform of PI3 kinase.

Another aspect of the invention provides the use of a Formula I compound in the manufacture of a medicament for treating a disease or disorder selected from immune disorders, cancer, cardiovascular disease, viral infection, inflammation, metabolism/endocrine function disorders and neurological disorders, and mediated by the p110 delta isoform of PI3 kinase.

The invention also relates to methods of using the Formula I compounds for in vitro, in situ, and in vivo diagnosis or treatment of mammalian cells, organisms, or associated pathological conditions, such as systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Another aspect of the invention provides a method of treating a disease or disorder which method comprises administering a Formula I compound to a patient with a disease or disorder selected from immune disorders, cancer, cardiovascular disease, viral infection, inflammation, metabolism/endocrine function disorders and neurological disorders, and mediated by the p110 delta isoform of PI3 kinase. The method may further comprise administering an additional therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

Another aspect of the invention provides a kit for treating a condition mediated by the p110 delta isoform of PI3 kinase, comprising a first pharmaceutical composition comprising a Formula I compound; and instructions for use.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-pentyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynyl radical may be optionally. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted independently with one or more substituents described below.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S), or a bicycle having 7 to 10 ring members (4 to 9 carbon atoms and 1 to 6 heteroatoms selected from N, O, P, and S) for example a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with Formula I compounds encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase $A_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, II), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega11 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole;

Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this invention," and "compounds of the present invention" and "compounds of Formula I" include compounds of Formulas I and stereoisomers, tautomers, solvates, metabolites, and pharmaceutically acceptable salts and prodrugs thereof.

Formula I Compounds of the Invention

Formula I compounds include compounds selected from Formulas Ia and Ib:

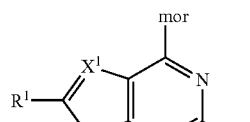

Ia

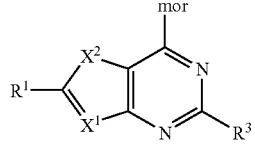

Ib including stereoisomers, tautomers, or pharmaceutically acceptable salts thereof, wherein (i) $X^1$ is N and $X^2$ is S, (ii) $X^1$ is $CR^7$ and $X^2$ is S, (iii) $X^1$ is N and $X^2$ is $NR^2$, (iv) $X^1$ is $CR^7$ and $X^2$ is O, or (v) $X^1$ is $CR^7$ and $X^2$ is $NR^2$;

$R^1$ is selected from $C_1$-$C_{12}$ alkyl, $C_2$-$C_8$ alkenyl, $C_2$-$C_8$ alkynyl, $C_6$-$C_{20}$ aryl, —($C_1$-$C_{12}$ alkylene)-($C_3$-$C_{12}$ carbocyclyl), —($C_1$-$C_{12}$ alkylene)-O—($C_1$-$C_{12}$ alkylene)-($C_3$-$C_{12}$ heterocyclyl), —($C_1$-$C_{12}$ alkylene)-O—($C_1$-$C_{12}$ alkylene)-C(=O)—($C_3$-$C_{12}$ heterocyclyl), —($C_1$-$C_{12}$ alkylene)-($C_2$-$C_{20}$ heterocyclyl), —($C_1$-$C_{12}$ alkylene)-($C_2$-$C_{20}$ heterocyclyl)-($C_2$-$C_{20}$ heterocyclyl), —($C_1$-$C_{12}$ alkylene)-($C_2$-$C_{20}$ heterocyclyl)-($C_3$-$C_{12}$ carbocyclyl), —($C_1$-$C_{12}$ alkylene)-($C_2$-$C_{20}$ heterocyclyl)-C(=O)—($C_2$-$C_{20}$ heterocyclyl), —($C_1$-$C_{12}$ alkylene)-($C_1$-$C_{20}$ heteroaryl), —($C_1$-$C_{12}$ alkylene)-($C_2$-$C_{20}$ heterocyclyl)-($C_1$-$C_{12}$ alkyl), —($C_1$-$C_{12}$ alkylene)-($C_6$-$C_{20}$ aryl)-($C_1$-$C_{12}$ alkyl), —($C_1$-$C_{12}$ alkylene)-($C_1$-$C_{20}$ heteroaryl)-($C_1$-$C_{12}$ alkyl), —($C_1$-$C_{12}$ alkylene)-C(=O)—($C_2$-$C_{20}$ heterocyclyl), —($C_1$-$C_{12}$ alkylene)-$NHR^2$, —($C_1$-$C_{12}$ alkylene)N($C_1$-$C_{12}$ alkyl)$R^2$, —($C_1$-$C_{12}$ alkylene)-N($C_1$-$C_{12}$ alkyl)($C_2$-$C_{20}$ heterocyclyl), —($C_1$-$C_{12}$ alkylene)-NH—($C_1$-$C_{12}$ alkylene)-($C_1$-$C_{20}$ heteroaryl), —($C_1$-$C_{12}$ alkylene)-NH—($C_1$-$C_{12}$ alkylene)-($C_1$-$C_{20}$ heterocyclyl), —($C_1$-$C_{12}$ alkylene)-NH—($C_1$-$C_{12}$ alkylene)-NHC(=O)—($C_1$-$C_{20}$ heteroaryl), —($C_1$-$C_{12}$ alkylene)-($C_2$-$C_{20}$ heterocyclyl)-N($C_1$-$C_{12}$ alkyl)$R^{2'}$, —($C_1$-$C_{12}$ alkylene)-($C_2$-$C_{20}$ heterocyclyl)-($C_1$-$C_{12}$ alkyl)N($C_1$-$C_{12}$ alkyl)$R^{2'}$, and —($C_1$-$C_{12}$ alkylene)-N($C_2$-$C_{20}$ heterocyclyl)$R^{2'}$, where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$C(CH_3)_3$, —$CH_2OH$, —$CH_2CH_2OH$, —$C(CH_3)_2OH$, —$C(CH_3)_2OCH_3$, —CN, —$CF_3$, —$CO_2H$, —$COCH_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —N($CH_3)_2$, —$NHCOCH_3$, —$NHS(O)_2CH_3$, —N($CH_3$)C($CH_3)_2$$CONH_2$, —N($CH_3$)$CH_2CH_2S(O)_2CH_3$, =O, —OH, —$OCH_3$, —$S(O)_2N(CH_3)_2$, —$SCH_3$, —$CH_2OCH_3$, —$S(O)_2$$CH_3$, cyclopropyl, morpholino, and 1,1-dioxo-thiopyran-4-yl;

$R^2$ and $R^{2'}$ are independently selected from $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2OH$, —CN, —$CF_3$, —$CO_2H$, —$COCH_3$, —$CO_2CH_3$, —$CONH_2$, —$CONHCH_3$, —CON($CH_3)_2$, —$NO_2$, —$NH_2$, —$NHCH_3$, —$NHCOCH_3$, —$NHS(O)_2CH_3$, —OH, —$OCH_3$, —$S(O)_2N(CH_3)_2$, —$SCH_3$, —$CH_2OCH_3$, and —$S(O)_2CH_3$;

$R^3$ is selected from:

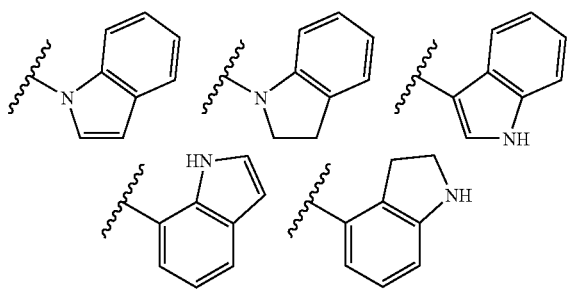

where the wavy line indicates the site of attachment;

each of which are optionally substituted with one or more groups independently selected from F, Cl, Br, I, —CH$_3$, —CH$_2$CH$_3$, —CH$_2$CH$_2$CH$_3$, —CH(CH$_3$)$_2$, —C(CH$_3$)$_3$, —CH$_2$OCH$_3$, —CHF$_2$, —CN, —CF$_3$, —CH$_2$OH, —CH$_2$OCH$_3$, —CH$_2$CH$_2$OH, —CH$_2$C(CH$_3$)$_2$OH, —CH(CH$_3$)OH, —CH(CH$_2$CH$_3$)OH, —CH$_2$CH(OH)CH$_3$, —C(CH$_3$)$_2$OH, —C(CH$_3$)$_2$OCH$_3$, —CH(CH$_3$)F, —C(CH$_3$)F$_2$, —CH(CH$_2$CH$_3$)F, —C(CH$_2$CH$_3$)$_2$F, —CO$_2$H, —CONH$_2$, —CON(CH$_2$CH$_3$)$_2$, —COCH$_3$, —CON(CH$_3$)$_2$, —NO$_2$, —NH$_2$, —NHCH$_3$, —N(CH$_3$)$_2$, —NHCH$_2$CH$_3$, —NHCH(CH$_3$)$_2$, —NHCH$_2$CH$_2$OH, —NHCH$_2$CH$_2$OCH$_3$, —NHCOCH$_3$, —NHCOCH$_2$CH$_3$, —NHCOCH$_2$OH, —NHS(O)$_2$CH$_3$, —N(CH$_3$)S(O)$_2$CH$_3$, =O, —OH, —OCH$_3$, —OCH$_2$CH$_3$, —OCH(CH$_3$)$_2$, —SH, —NHC(=O)NHCH$_3$, —NHC(=O)NHCH$_2$CH$_3$, —S(O)CH$_3$, —S(O)CH$_2$CH$_3$, —S(O)$_2$CH$_3$, —S(O)$_2$NH$_2$, —S(O)$_2$NHCH$_3$, —S(O)$_2$N(CH$_3$)$_2$, —CH$_2$S(O)$_2$CH$_3$;

R$^7$ is selected from H, C$_1$-C$_{12}$ alkyl, C$_2$-C$_8$ alkenyl, C$_2$-C$_8$ alkynyl, —(C$_1$-C$_{12}$ alkylene)-(C$_3$-C$_{12}$ carbocyclyl), —(C$_1$-C$_{12}$ alkylene)-(C$_2$-C$_{20}$ heterocyclyl), —(C$_1$-C$_{12}$ alkylene)-C(=O)—(C$_2$-C$_{20}$ heterocyclyl), —(C$_1$-C$_{12}$ alkylene)-(C$_6$-C$_{20}$ aryl), and —(C$_1$-C$_{12}$ alkylene)-(C$_1$-C$_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$OH, —CN, —CF$_3$, —CO$_2$H, —COCH$_3$, —CO$_2$CH$_3$, —CONH$_2$, —CONHCH$_3$, —CON(CH$_3$)$_2$, —NO$_2$, —NH$_2$, —NHCH$_3$, —NHCOCH$_3$, —NHS(O)$_2$CH$_3$, —OH, —OCH$_3$, —S(O)$_2$N(CH$_3$)$_2$, —SCH$_3$, —CH$_2$OCH$_3$, and —S(O)$_2$CH$_3$; and mor is a morpholine group unsubstituted or substituted with one or more groups selected from F, Cl, Br, I, —CH$_3$, —CH$_2$CH$_3$, —CH$_2$CH$_2$CH$_3$, —CH(CH$_3$)$_2$, —C(CH$_3$)$_3$, —CH$_2$OCH$_3$, —CHF$_2$, —CN, —CF$_3$, —CH$_2$OH, —CH$_2$OCH$_3$, —CH$_2$CH$_2$OH, —CH$_2$C(CH$_3$)$_2$OH, —CH(CH$_3$)OH, —CH(CH$_2$CH$_3$)OH, —CH$_2$CH(OH)CH$_3$, —C(CH$_3$)$_2$OH, —C(CH$_3$)$_2$OCH$_3$, —CH(CH$_3$)F, —C(CH$_3$)F$_2$, —CH(CH$_2$CH$_3$)F, —C(CH$_2$CH$_3$)$_2$F, —CO$_2$H, —CONH$_2$, —CON(CH$_2$CH$_3$)$_2$, —COCH$_3$, —CON(CH$_3$)$_2$, —NO$_2$, —NH$_2$, —NHCH$_3$, —N(CH$_3$)$_2$, —NHCH$_2$CH$_3$, —NHCH(CH$_3$)$_2$, —NHCH$_2$CH$_2$OH, —NHCH$_2$CH$_2$OCH$_3$, —NHCOCH$_3$, —NHCOCH$_2$CH$_3$, —NHCOCH$_2$OH, —NHS(O)$_2$CH$_3$, —N(CH$_3$)S(O)$_2$CH$_3$, =O, —OH, —OCH$_3$, —OCH$_2$CH$_3$, —OCH(CH$_3$)$_2$, —SH, —NHC(=O)NHCH$_3$, —NHC(=O)NHCH$_2$CH$_3$, —S(O)CH$_3$, —S(O)CH$_2$CH$_3$, —S(O)$_2$CH$_3$, —S(O)$_2$NH$_2$, —S(O)$_2$NHCH$_3$, —S(O)$_2$N(CH$_3$)$_2$, —CH$_2$S(O)$_2$CH$_3$.

Exemplary Formula I compounds include thiazolopyrimidines where (i) X$^1$ is N and X$^2$ is S:

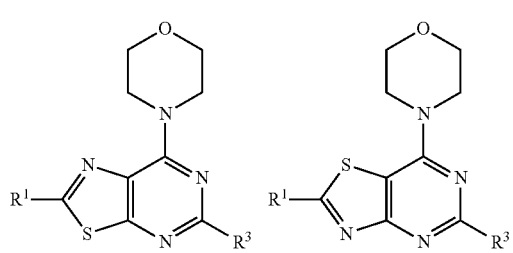

Exemplary Formula I compounds include thienopyrimidines where (ii) X$^1$ is CR$^7$ and X$^2$ is S:

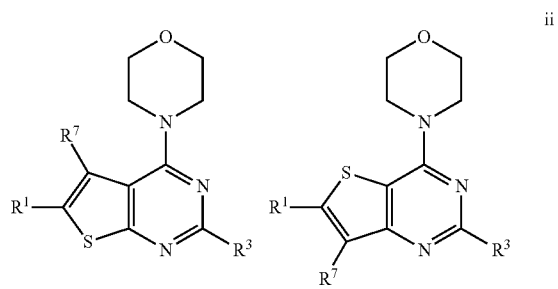

Exemplary Formula I compounds include purines where (iii) X$^1$ is N and X$^2$ is NR$^2$:

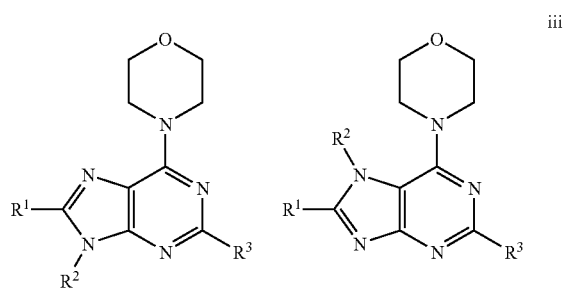

Exemplary Formula I compounds include furanopyrimidines where (iv) X$^1$ is CR$^7$ and X$^2$ is O:

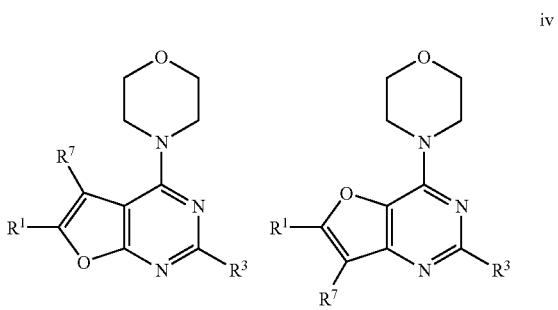

Exemplary Formula I compounds include pyrrolopyrimidines where (v) X$^1$ is CR$^7$ and X$^2$ is NR$^2$:

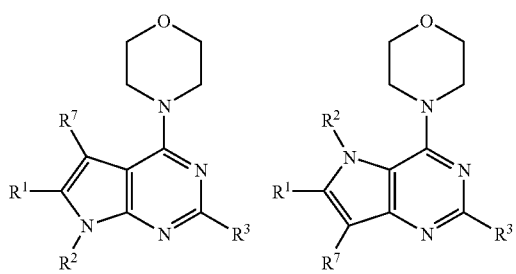

Exemplary embodiments of R¹ include the groups:
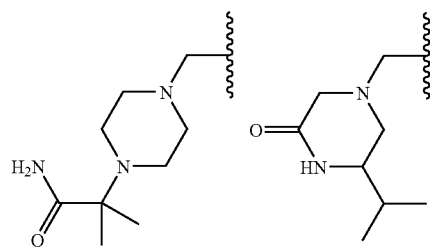
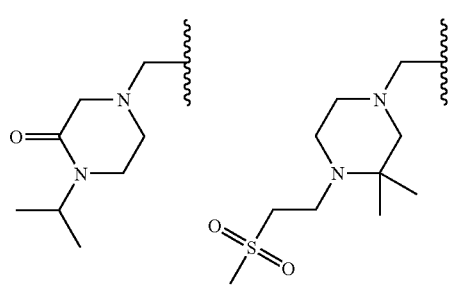
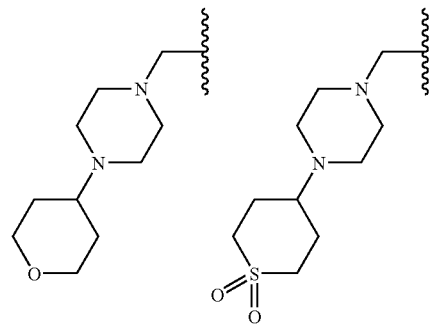
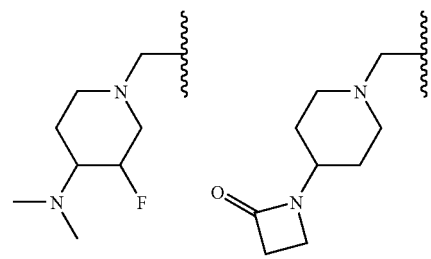
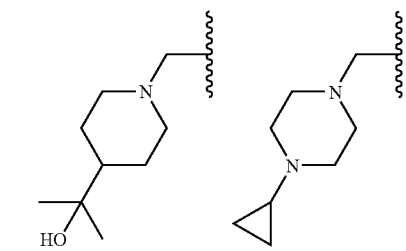
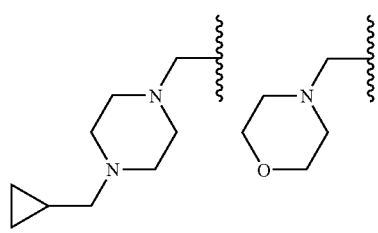
-continued
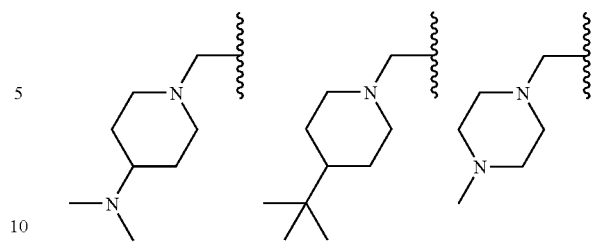
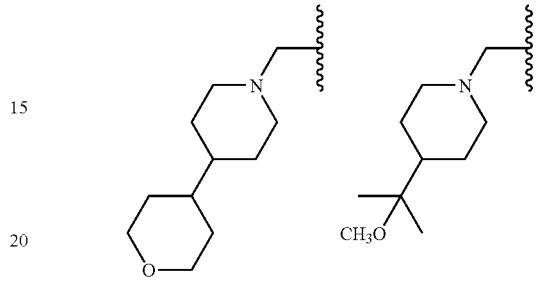
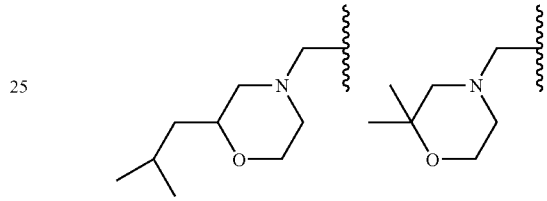
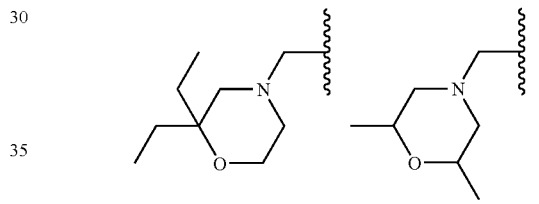
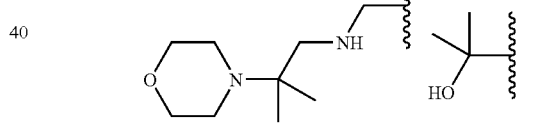
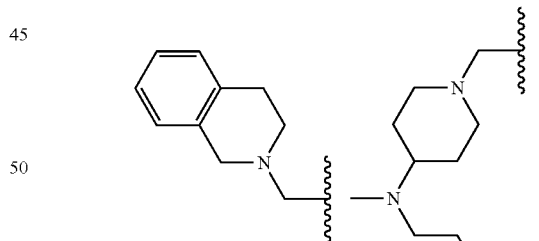
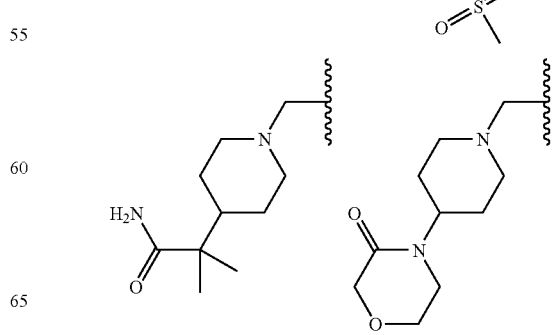

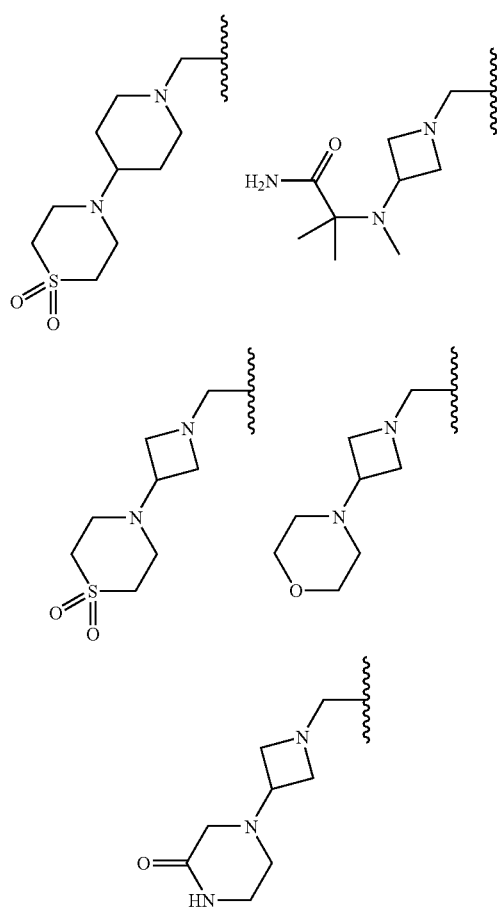
where the wavy line indicates the site of attachment to the Formula I structure.
Exemplary embodiments of R[1] also include the groups:
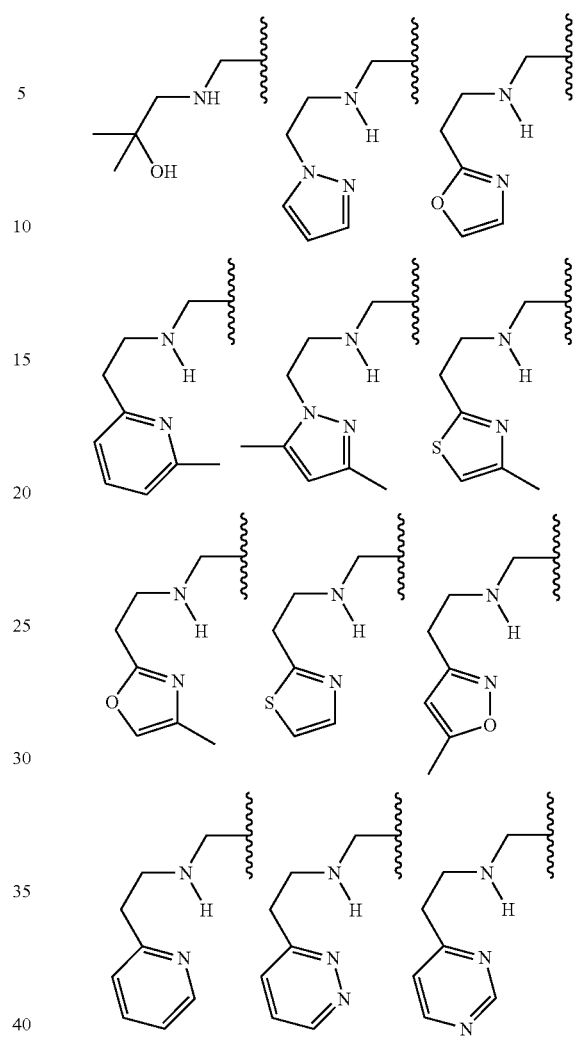
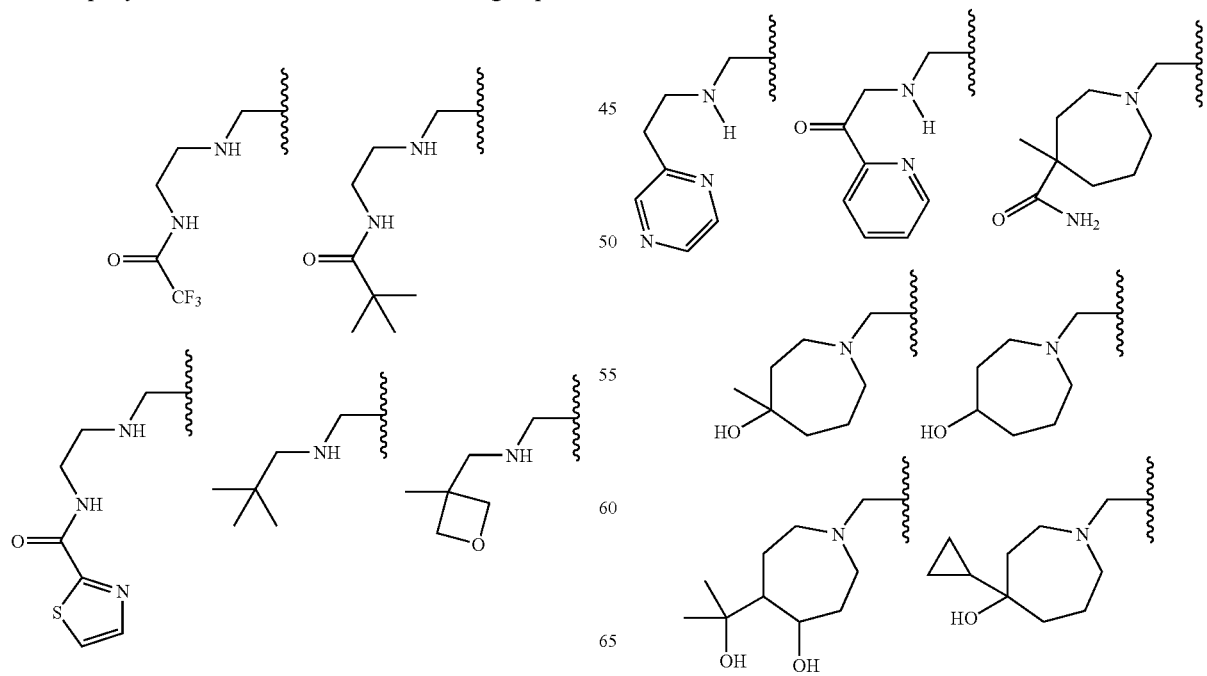

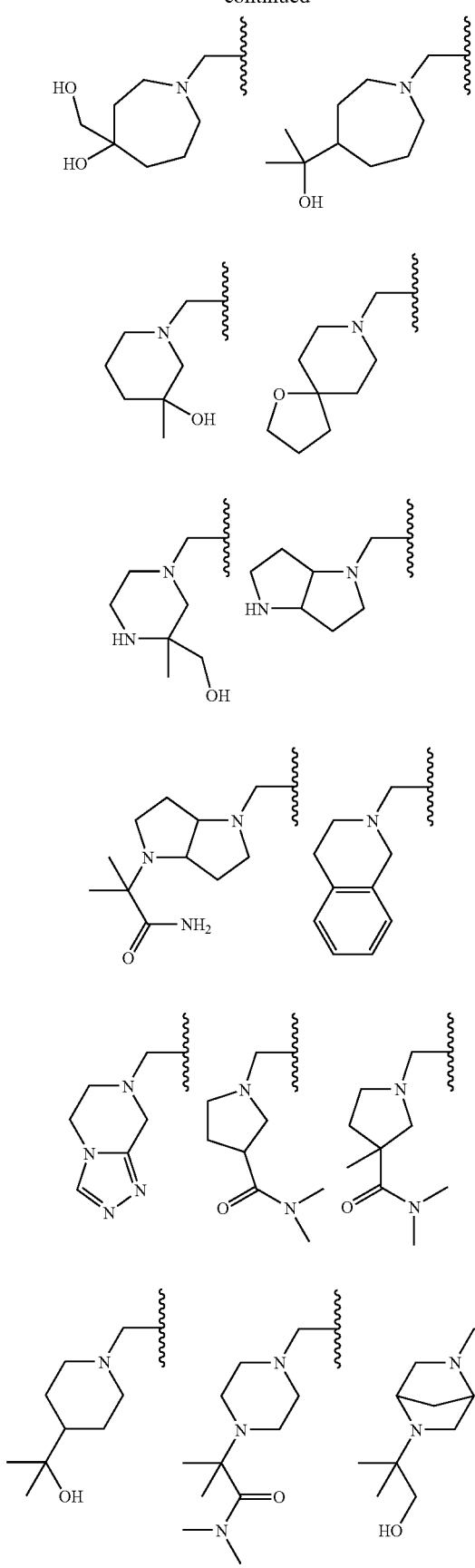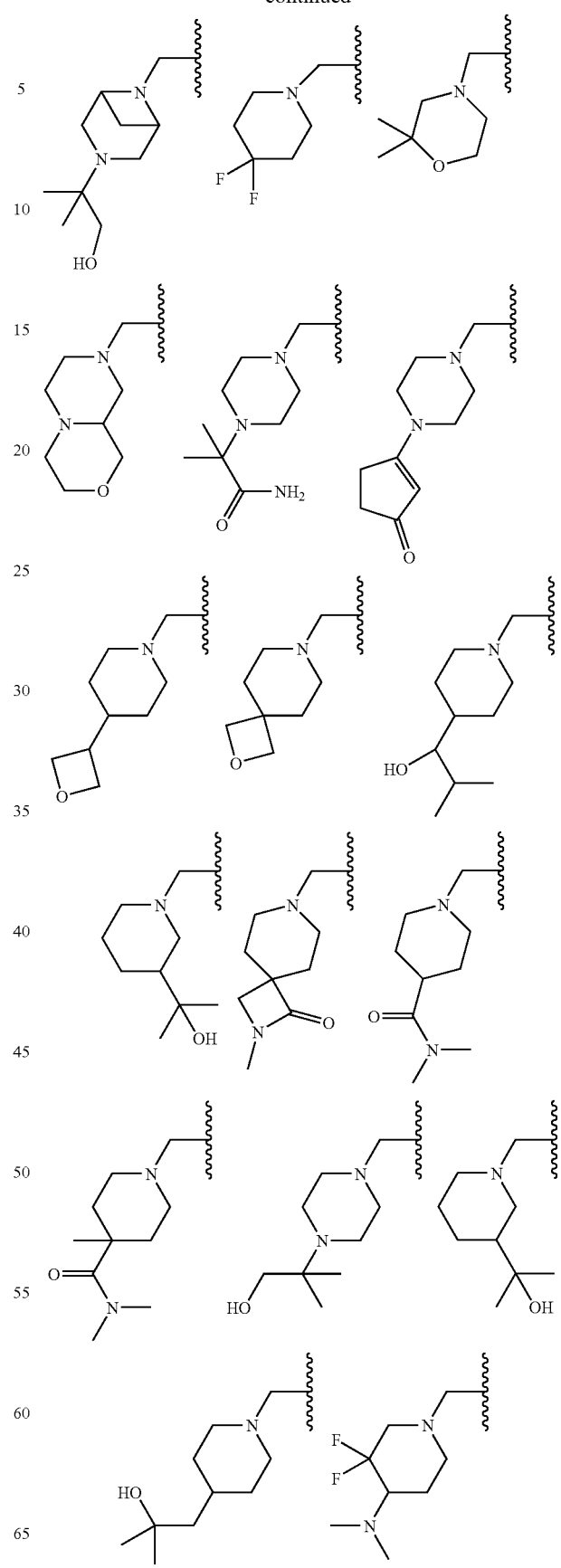

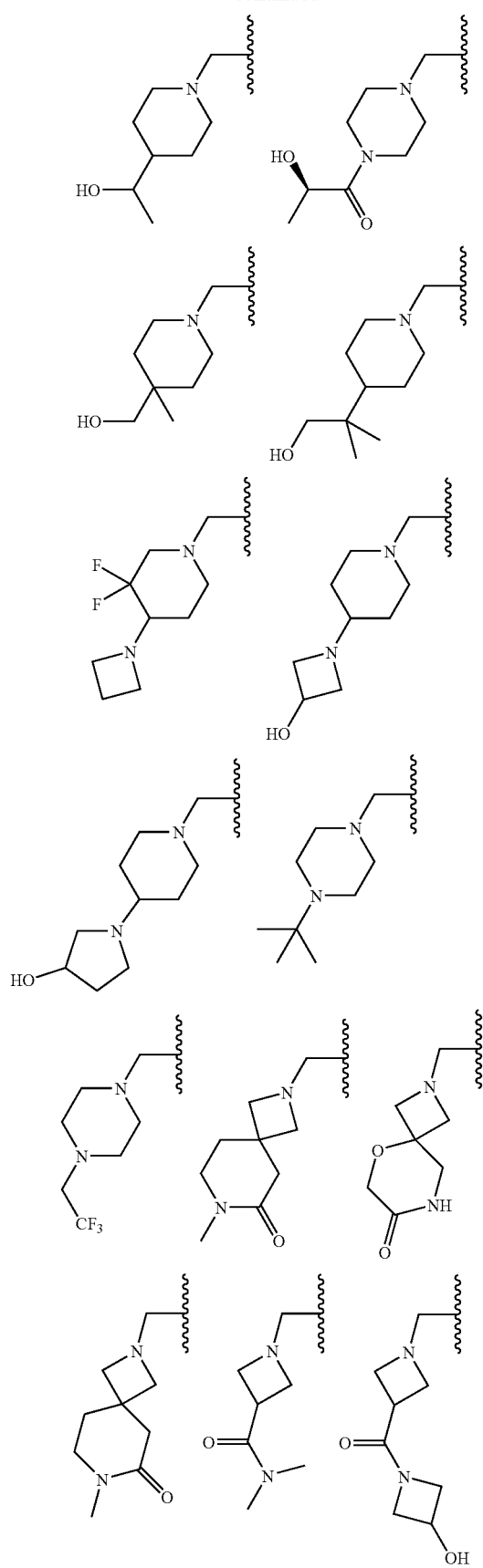
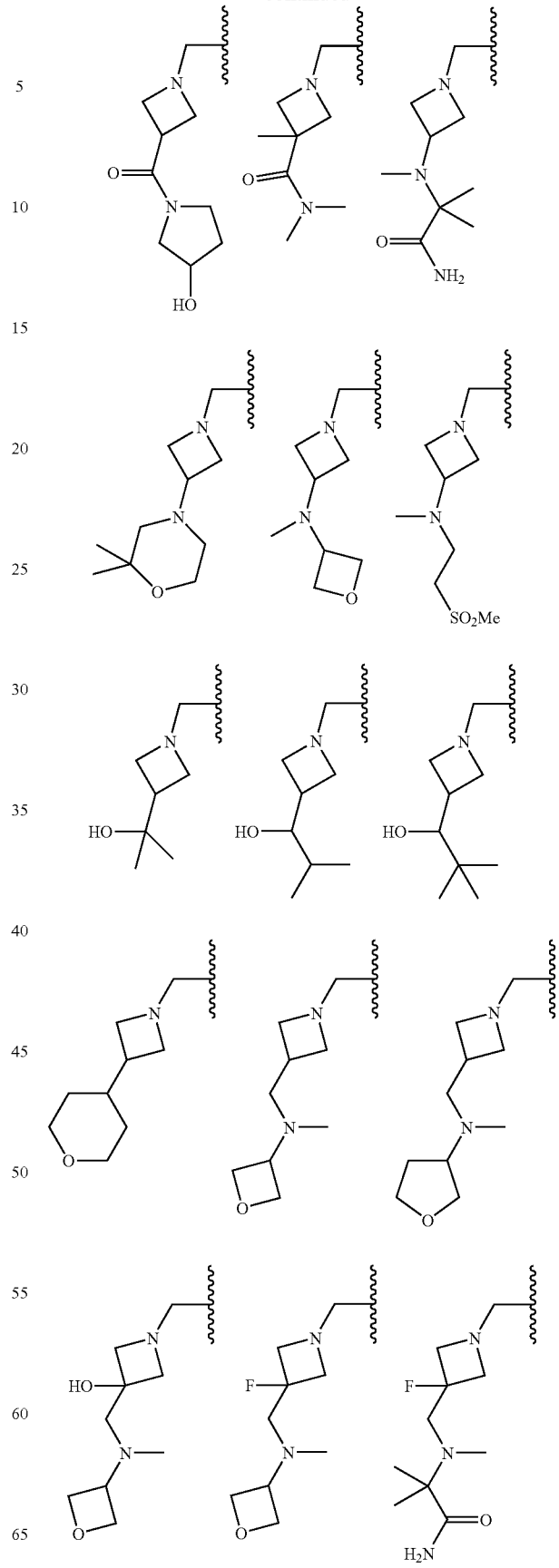

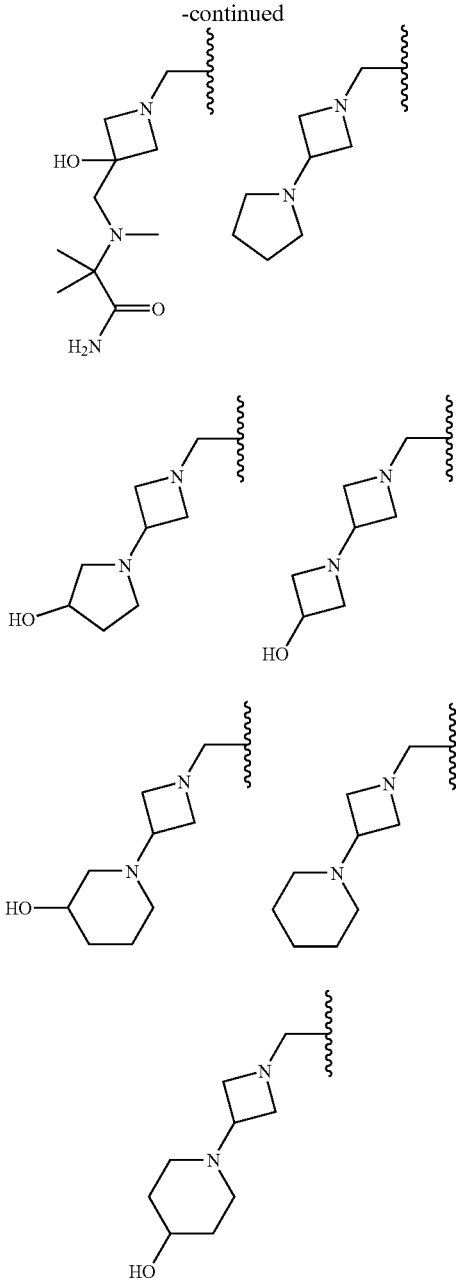

where the wavy line indicates the attachment to the Formula I structure.

Formula I compounds include compounds selected from Formulas Ia' and Ib':

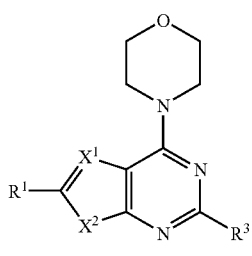

Ia'

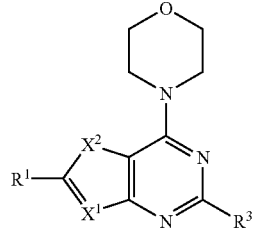

Ib' and stereoisomers, geometric isomers, tautomers, or pharmaceutically acceptable salts thereof, wherein (i) $X^1$ is N and $X^2$ is S, (ii) $X^1$ is $CR^7$ and $X^2$ is S, (iii) $X^1$ is N and $X^2$ is $NR^2$, (iv) $X^1$ is $CR^7$ and $X^2$ is O, or (v) $X^1$ is $CR^7$ and $X^2$ is $NR^2$;

$R^1$ is selected from $C_1$-$C_{12}$ alkyl, $C_2$-$C_8$ alkenyl, $C_2$-$C_8$ alkynyl, $C_6$-$C_{20}$ aryl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-($C_2$-$C_{20}$ heterocyclyl)-($C_2$-$C_{20}$ heterocyclyl), —($C_1$-$C_{12}$ alkylene)-($C_2$-$C_{20}$ heterocyclyl)-($C_3$-$C_{12}$ carbocyclyl), —($C_1$-$C_{12}$ alkylene)-($C_2$-$C_{20}$ heterocyclyl)-C(=O)—($C_2$-$C_{20}$ heterocyclyl), —($C_1$-$C_{12}$ alkylene)-($C_1$-$C_{20}$ heteroaryl), —($C_1$-$C_{12}$ alkylene)-($C_2$-$C_{20}$ heterocyclyl)-($C_1$-$C_{12}$ alkyl), —($C_1$-$C_{12}$ alkylene)-($C_6$-$C_{20}$ aryl)-($C_1$-$C_{12}$ alkyl), —($C_1$-$C_{12}$ alkylene)-($C_1$-$C_{20}$ heteroaryl)-($C_1$-$C_{12}$ alkyl), —($C_1$-$C_{12}$ alkylene)-C(=O)—($C_2$-$C_{20}$ heterocyclyl), —($C_1$-$C_{12}$ alkylene)-$NHR^2$, —($C_1$-$C_{12}$ alkylene)-N($C_1$-$C_{12}$ alkyl)$R^2$, —($C_1$-$C_{12}$ alkylene)-N($C_1$-$C_{12}$ alkyl)($C_2$-$C_{20}$ heterocyclyl), —($C_1$-$C_{12}$ alkylene)-NH—($C_1$-$C_{12}$ alkylene)-($C_1$-$C_{20}$ heteroaryl), —($C_1$-$C_{12}$ alkylene)-NH—($C_1$-$C_{12}$ alkylene)-($C_1$-$C_{20}$ heterocyclyl), —($C_1$-$C_{12}$ alkylene)-NH—($C_1$-$C_{12}$ alkylene)-NHC(=O)—($C_1$-$C_{20}$ heteroaryl), —($C_1$-$C_{12}$ alkylene)-($C_2$-$C_{20}$ heterocyclyl)-N($C_1$-$C_{12}$ alkyl)$R^2$, —($C_1$-$C_{12}$ alkylene)-($C_2$-$C_{20}$ heterocyclyl)-($C_1$-$C_{12}$ alkyl)-N($C_1$-$C_{12}$ alkyl)$R^2$, and —($C_1$-$C_{12}$ alkylene)-N($C_2$-$C_{20}$ heterocyclyl)$R^2$, where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$CH_2OH$, —$CH_2CH_2OH$, —CN, —$CF_3$, —$CO_2H$, —$COCH_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$CH_2OCH_3$, —$S(O)_2CH_3$, cyclopropyl, and morpholino;

$R^2$ is selected from $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2OH$, —CN, —$CF_3$, —$CO_2H$, —$COCH_3$, —$CO_2CH_3$, —$CONH_2$, —$CONHCH_3$, —$CON(CH_3)_2$, —$NO_2$, —$NH_2$, —$NHCH_3$, —$NHCOCH_3$, —$NHS(O)_2CH_3$, —OH, —$OCH_3$, —$S(O)_2N(CH_3)_2$, —$SCH_3$, —$CH_2OCH_3$, and —$S(O)_2CH_3$;

$R^3$ is selected from:

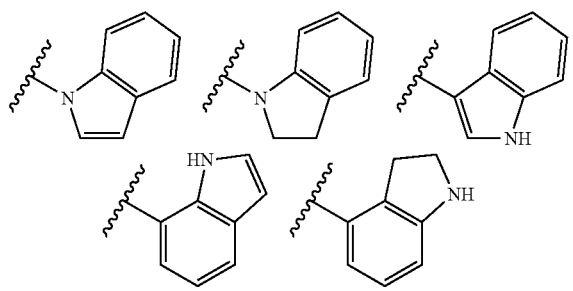

where the wavy line indicates the site of attachment;

each of which are optionally substituted with one or more groups independently selected from F, Cl, Br, I, —$CH_3$, —$CH_2CH_3$, —$CH_2CH_2CH_3$, —$CH(CH_3)_2$, —$C(CH_3)_3$, —$CH_2OCH_3$, —$CHF_2$, —CN, —$CF_3$, —$CH_2OH$, —$CH_2OCH_3$, —$CH_2CH_2OH$, —$CH_2C(CH_3)_2OH$, —CH($CH_3$)OH, —CH($CH_2CH_3$)OH, —$CH_2CH(OH)CH_3$, —C($CH_3$)$_2$OH, —C($CH_3$)$_2OCH_3$, —CH($CH_3$)F, —C($CH_3$)$F_2$, —CH($CH_2CH_3$)F, —C($CH_2CH_3$)$_2$F, —$CO_2H$, —$CONH_2$, —CON($CH_2CH_3$)$_2$, —$COCH_3$, —CON($CH_3$)$_2$, —$NO_2$, —$NH_2$, —$NHCH_3$, —N($CH_3$)$_2$, —$NHCH_2CH_3$, —NH$CH(CH_3)_2$, —$NHCH_2CH_2OH$, —$NHCH_2CH_2OCH_3$, —$NHCOCH_3$, —$NHCOCH_2CH_3$, —$NHCOCH_2OH$, —$NHS(O)_2CH_3$, —$N(CH_3)S(O)_2CH_3$, =O, —OH, —$OCH_3$, —$OCH_2CH_3$, —$OCH(CH_3)_2$, —SH, —NHC(=O)$NHCH_3$, —NHC(=O)$NHCH_2CH_3$, —$S(O)CH_3$, —$S(O)CH_2CH_3$, —$S(O)_2CH_3$, —$S(O)_2NH_2$, —$S(O)_2NHCH_3$, —$S(O)_2N(CH_3)_2$, —$CH_2S(O)_2CH_3$; and $R^7$ is selected from H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)-($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2OH$, —CN, —$CF_3$, —$CO_2H$, —$COCH_3$, —$CO_2CH_3$, —$CONH_2$, —$CONHCH_3$, —CON($CH_3$)$_2$, —$NO_2$, —$NH_2$, —$NHCH_3$, —$NHCOCH_3$, —$NHS(O)_2CH_3$, —OH, —$OCH_3$, —$S(O)_2N(CH_3)_2$, —$SCH_3$, —$CH_2OCH_3$, and —$S(O)_2CH_3$.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all geometric and positional isomers. For example, if a Formula I compound incorporates a double bond or a fused ring, the cis- and trans-forms, as well as mixtures thereof, are embraced within the scope of the invention. Both the single positional isomers and mixture of positional isomers are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}N$, $^{15}O$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^3H$ and $^{14}C$) are useful in compound and/or substrate tissue distribution assays. Tritiated ($^3H$) and carbon-14 ($^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Biological Evaluation

The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Accordingly, a "selective PI3K delta inhibitor" can be understood to refer to a compound that exhibits a 50% inhibitory concentration ($IC_{50}$) with respect to PI3K delta that is at least at least 10-fold lower than the IC50 value with respect to any or all of the other Class I PI3K family members.

Determination of the activity of PI3 kinase activity of Formula I compounds is possible by a number of direct and indirect detection methods. Certain exemplary compounds described herein were assayed for their ability to inhibit PI3K alpha, beta, gamma, and delta isoforms (Example 901). The range of IC50 values for inhibition of PI3K delta was less than 1 nM (nanomolar) to about 10 µM (micromolar). Certain exemplary compounds of the invention had PI3K delta inhibitory $IC_{50}$ values less than 10 nM. The compounds are selective for the p110δ (delta) isoform, which is a class Ia PI3 kinase, over other class Ia PI3 kinases, and are thus selective for the p110δ isoform over both the p110α (alpha) isoform and the p110β (beta) isoform. In particular, they are selective for p110δ (delta) over p110α (alpha). The compounds are also selective for the p110δ isoform over p110γ (gamma), which is a class Ib kinase. The selectivity exhibited by Formula I compounds of the invention for p110δ (delta) over the p110α (alpha) isoform of PI3 kinase is at least 10 fold, as exemplified by the ratios of biochemical $IC_{50}$ values. (Example 901).

Certain Formula I compounds may have antiproliferative activity to treat hyperproliferative disorders such as cancer. The Formula I compounds may inhibit tumor growth in mammals and may be useful for treating human cancer patients. Formula I compounds may be tested for in vitro cell proliferation activity and in vivo tumor growth inhibition according to the methods in WO 2006/046031; US 2008/0039459; US 2008/0076768; US 2008/0076758; WO 2008/070740; WO 2008/073785, which are incorporated by reference herein.

Evaluation of drug-induced immunosuppression by the compounds of the invention may be performed using in vivo functional tests, such as rodent models of induced arthritis and therapeutic or prophylactic treatment to assess disease score, T cell-dependent antibody response (TDAR), and delayed-type hypersensitivity (DTH). Other in vivo systems including murine models of host defense against infections or tumor resistance (Burleson G R, Dean J H, and Munson A E. *Methods in Immunotoxicology, Vol.* 1. Wiley-Liss, New York, 1995) may be considered to elucidate the nature or mechanisms of observed immunosuppression. The in vivo test systems can be complemented by well-established in vitro or ex vivo functional assays for the assessment of immune competence. These assays may comprise B or T cell proliferation in response to mitogens or specific antigens, measurement of signaling through the PI3K pathway in B or T cells or immortalized B or T cell lines, measurement of cell surface markers in response to B or T cell signaling, natural killer (NK) cell activity, mast cell activity, mast cell degranulation, macrophage phagocytosis or kill activity, and neutrophil oxidative burst and/or chemotaxis. In each of these tests determination of cytokine production by particular effector cells (e.g., lymphocytes, NK, monocytes/macrophages, neutrophils) may be included. The in vitro and ex vivo assays can be applied in both preclinical and clinical testing using lymphoid tissues and/or peripheral blood (House R V. "Theory and practice of cytokine assessment in immunotoxicology" (1999) Methods 19:17-27; Hubbard A K. "Effects of xenobiotics on macrophage function: evaluation in vitro" (1999) Methods; 19:8-16; Lebrec H, et al (2001) Toxicology 158:25-29).

Collagen-Induced Arthritis (CIA) 6-week detailed study was employed using an autoimmune mechanism to mimic human arthritis; rat and mouse models (Example 902). Collagen-induced arthritis (CIA) is one of the most commonly used animal models of human rheumatoid arthritis (RA). Joint inflammation, which develops in animals with CIA, strongly resembles inflammation observed in patients with RA. Blocking tumor necrosis factor (TNT) is an efficacious treatment of CIA, just as it is a highly efficacious therapy in treatment of RA patients. CIA is mediated by both T-cells and antibodies (B-cells). Macrophages are believed to play an important role in mediating tissue damage during disease development. CIA is induced by immunizing animals with collagen emulsified in Complete Freund's Adjuvant (CFA). It is most commonly induced in the DBA/1 mouse strain, but the disease can also be induced in Lewis rats. Formula I compounds were tested in the CIA test (Example 902).

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. (2004) Annu Rev Med 55:477). CD69 is the early activation marker in leukocytes including T cells, thymocytes, B cells, NK cells, neutrophils, and eosinophils. The CD69 human whole blood assay (Example 903) determines the ability of compounds to inhibit the production of CD69 by B lymphocytes in human whole blood activated by crosslinking surface IgM with goat $F(ab')_2$ anti-human IgM.

The T-cell Dependent Antibody Response (TDAR) is a predictive assay for immune function testing when potential immunotoxic effects of compounds need to be studied. The IgM-Plaque Forming Cell (PFC) assay, using Sheep Red Blood Cells (SRBC) as the antigen, is currently a widely accepted and validated standard test. TDAR has proven to be a highly predictable assay for adult exposure immunotoxicity detection in mice based on the US National Toxicology Program (NTP) database (M. I. Luster et al (1992) Fundam. Appl. Toxicol. 18:200-210). The utility of this assay stems from the fact that it is a holistic measurement involving several important components of an immune response. A TDAR is dependent on functions of the following cellular compartments: (1) antigen-presenting cells, such as macrophages or dendritic cells; (2) T-helper cells, which are critical players in the genesis of the response, as well as in isotype switching; and (3) B-cells, which are the ultimate effector cells and are responsible for antibody production. Chemically-induced changes in any one compartment can cause significant changes in the overall TDAR (M. P. Holsapple In: G. R. Burleson, J. H. Dean and A. E. Munson, Editors, *Modern Methods in Immunotoxicology, Volume* 1, Wiley-Liss Publishers, New York, N.Y. (1995), pp. 71-108). Usually, this assay is performed either as an ELISA for measurement of soluble antibody (R. J. Smialowicz et al (2001) Toxicol. Sci. 61:164-175) or as a plaque (or antibody) forming cell assay (L. Guo et al (2002) Toxicol. Appl. Pharmacol. 181:219-227) to detect plasma cells secreting antigen specific antibodies. The antigen of choice is either whole cells (e.g. sheep erythrocytes) or soluble protein antigens (T. Miller et al (1998) Toxicol. Sci. 42:129-135).

Exemplary Formula I compounds No. 101-137 in Table 1, were made, characterized, and tested for inhibition of PI3K delta and selectivity according to the methods of this invention, and have the following structures and corresponding names (ChemDraw Ultra, Version 9.0.1, CambridgeSoft Corp., Cambridge Mass.).

TABLE 1

| No. | Structure | Name |
|---|---|---|
| 101 | 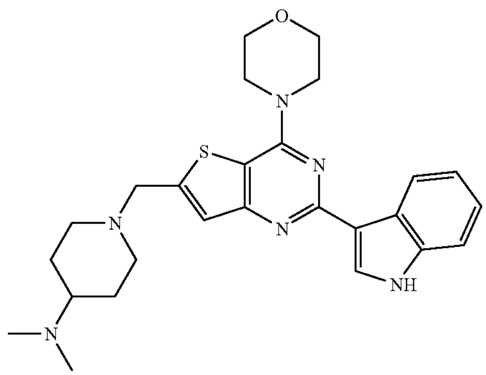 | 1-((2-(1H-indol-3-yl)-4-morpholinothieno[3,2-d]pyrimidin-6-yl)methyl)-N,N-dimethylpiperidin-4-amine |
| 102 | 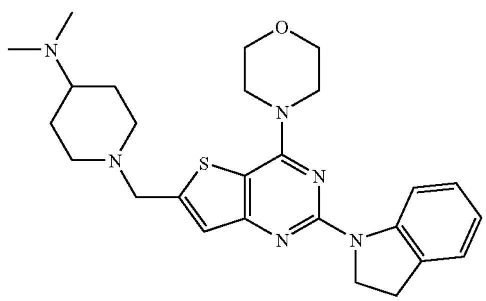 | 1-((2-(indolin-1-yl)-4-morpholinothieno[3,2-d]pyrimidin-6-yl)methyl)-N,N-dimethylpiperidin-4-amine |
| 103 | 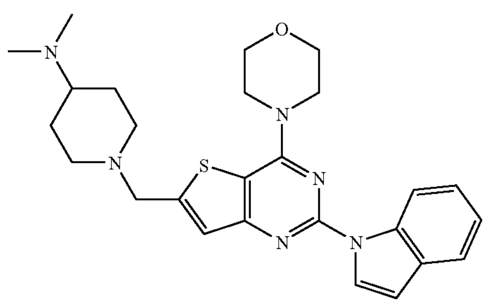 | 1-((2-(1H-indol-1-yl)-4-morpholinothieno[3,2-d]pyrimidin-6-yl)methyl)-N,N-dimethylpiperidin-4-amine |
| 104 | 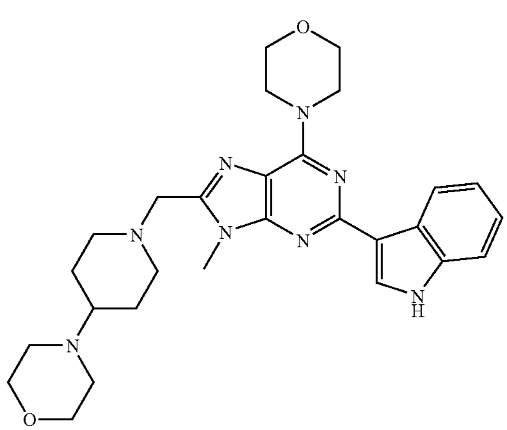 | 4-(1-((2-(1H-indol-3-yl)-9-methyl-6-morpholino-9H-purin-8-yl)methyl)piperidin-4-yl)morpholine |

TABLE 1-continued

| No. | Structure | Name |
|---|---|---|
| 105 | 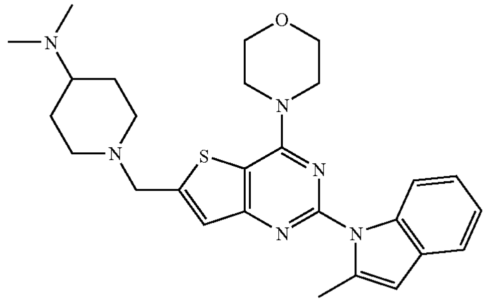 | N,N-dimethyl-1-((2-(2-methyl-1H-indol-1-yl)-4-morpholinothieno[3,2-d]pyrimidin-6-yl)methyl)piperidin-4-amine |
| 106 | 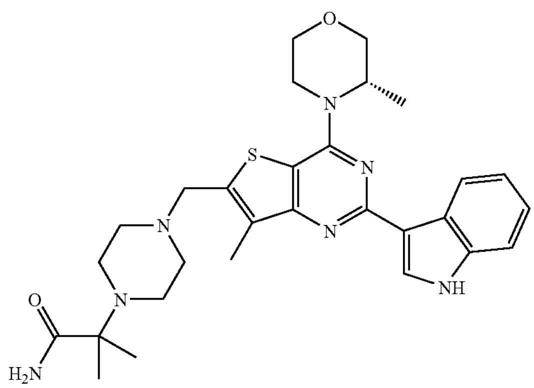 | (S)-2-(4-((2-(1H-indol-3-yl)-7-methyl-4-(3-methylmorpholino)thieno[3,2-d]pyrimidin-6-yl)methyl)piperazin-1-yl)-2-methylpropanamide |
| 107 | 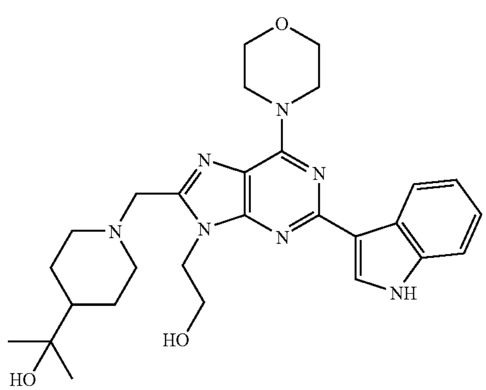 | 2-(1-((9-(2-hydroxyethyl)-2-(1H-indol-3-yl)-6-morpholino-9H-purin-8-yl)methyl)piperidin-4-yl)propan-2-ol |
| 108 | 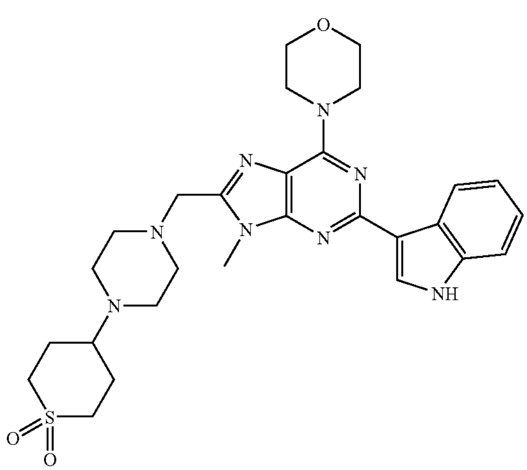 | 4-(2-(1H-indol-3-yl)-9-methyl-8-((4-(tetrahydro-2H-1,1-dioxo-thiopyran-4-yl)piperazin-1-yl)methyl)-9H-purin-6-yl)morpholine |

TABLE 1-continued

| No. | Structure | Name |
|---|---|---|
| 109 | 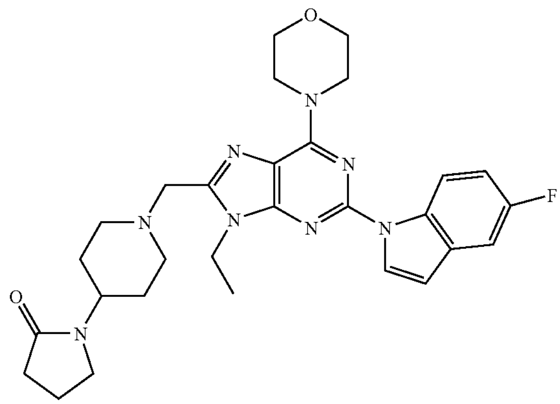 | 1-(1-((9-ethyl-2-(5-fluoro-1H-indol-1-yl)-6-morpholino-9H-purin-8-yl)methyl)piperidin-4-yl)pyrrolidin-2-one |
| 110 | 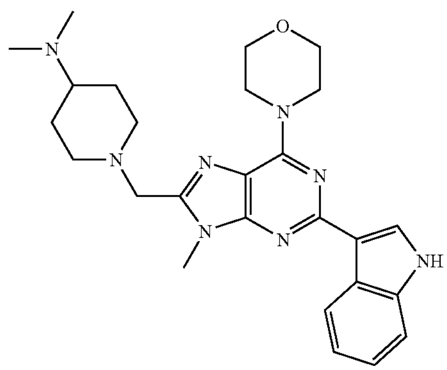 | 1-((2-(1H-indol-3-yl)-9-methyl-6-morpholino-9H-purin-8-yl)methyl)-N,N-dimethylpiperidin-4-amine |
| 111 | 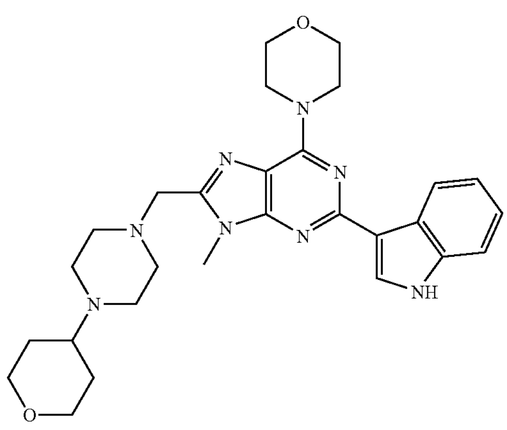 | 4-(2-(1H-indol-3-yl)-9-methyl-8-((4-(tetrahydro-2H-pyran-4-yl)piperazin-1-yl)methyl)-9H-purin-6-yl)morpholine |
| 112 | 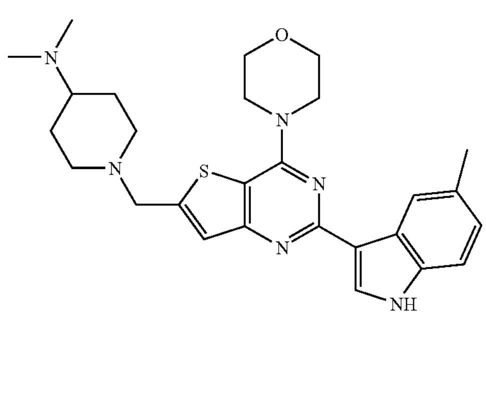 | N,N-dimethyl-1-((2-(5-methyl-1H-indol-3-yl)-4-morpholinothieno[3,2-d]pyrimidin-6-yl)methyl)piperidin-4-amine |

TABLE 1-continued

| No. | Structure | Name |
|---|---|---|
| 113 | 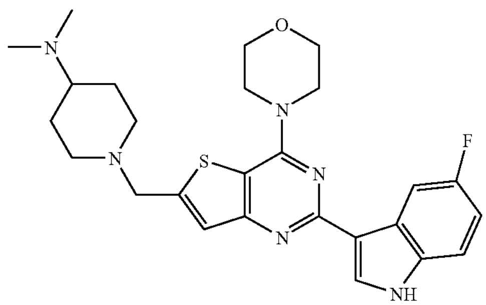 | 1-((2-(5-fluoro-1H-indol-3-yl)-4-morpholinothieno[3,2-d]pyrimidin-6-yl)methyl)-N,N-dimethylpiperidin-4-amine |
| 114 | 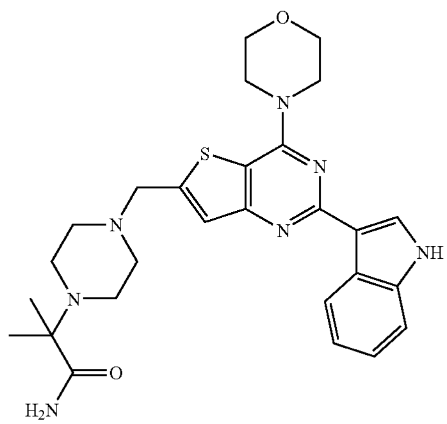 | 2-(4-((2-(1H-indol-3-yl)-4-morpholinothieno[3,2-d]pyrimidin-6-yl)methyl)piperazin-1-yl)-2-methylpropanamide |
| 115 | 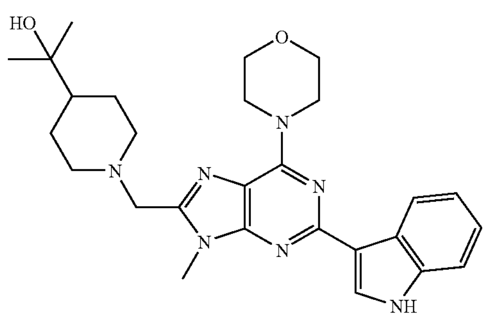 | 2-(1-((2-(1H-indol-3-yl)-9-methyl-6-morpholino-9H-purin-8-yl)methyl)piperidin-4-yl)propan-2-ol |
| 116 | 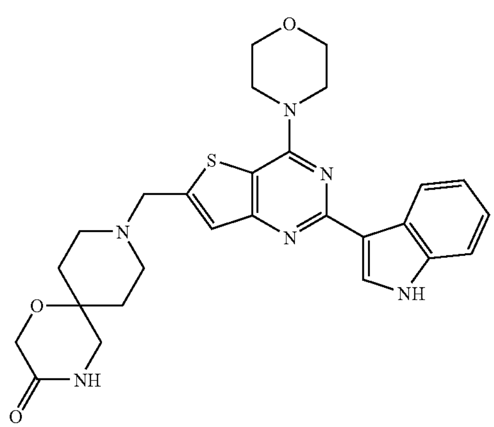 | 9-((2-(1H-indol-3-yl)-4-morpholinothieno[3,2-d]pyrimidin-6-yl)methyl)-1-oxa-4,9-diazaspiro[5.5]undecan-3-one |

TABLE 1-continued

| No. | Structure | Name |
|-----|-----------|------|
| 117 | 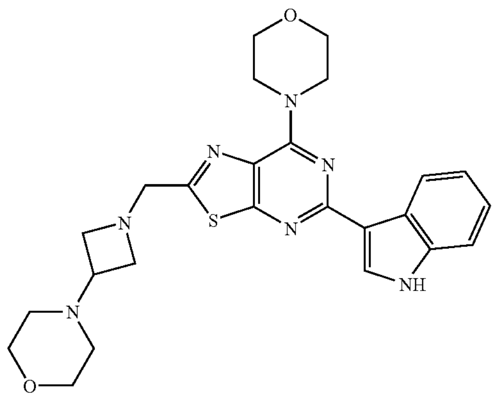 | 4-(5-(1H-indol-3-yl)-2-((3-morpholinoazetidin-1-yl)methyl)thiazolo[5,4-d]pyrimidin-7-yl)morpholine |
| 118 | 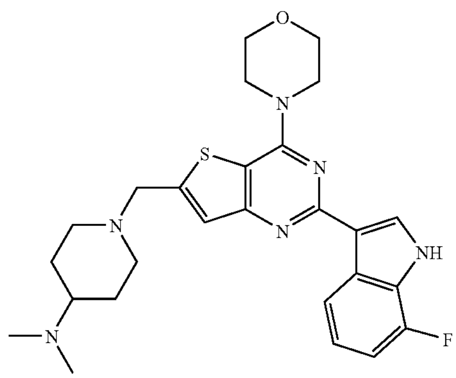 | 1-((2-(7-fluoro-1H-indol-3-yl)-4-morpholinothieno[3,2-d]pyrimidin-6-yl)methyl)-N,N-dimethylpiperidin-4-amine |
| 119 | 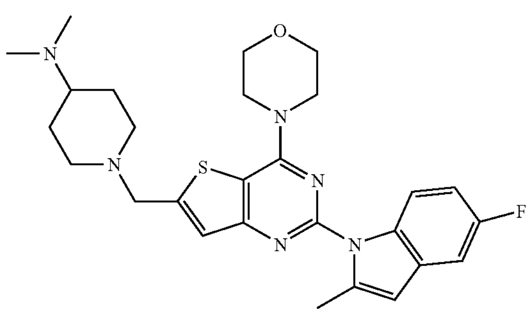 | 1-((2-(5-fluoro-2-methyl-1H-indol-1-yl)-4-morpholinothieno[3,2-d]pyrimidin-6-yl)methyl)-N,N-dimethylpiperidin-4-amine |
| 120 | 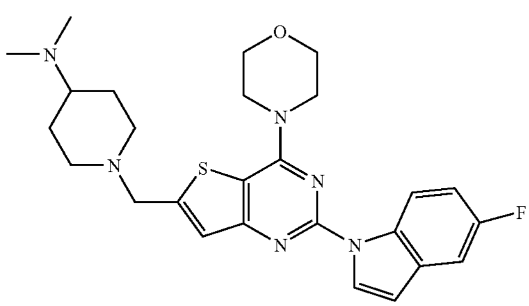 | 1-((2-(5-fluoro-1H-indol-1-yl)-4-morpholinothieno[3,2-d]pyrimidin-6-yl)methyl)-N,N-dimethylpiperidin-4-amine |

TABLE 1-continued

| No. | Structure | Name |
|---|---|---|
| 121 | 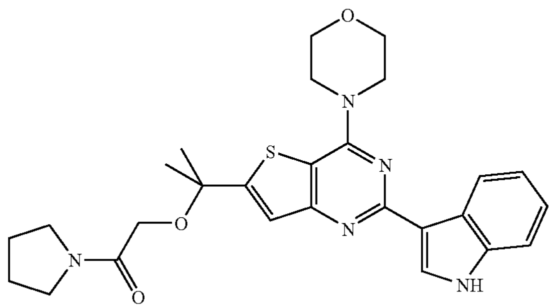 | 2-(2-(2-(1H-indol-3-yl)-4-morpholinothieno[3,2-d]pyrimidin-6-yl)propan-2-yloxy)-1-(pyrrolidin-1-yl)ethanone |
| 122 | 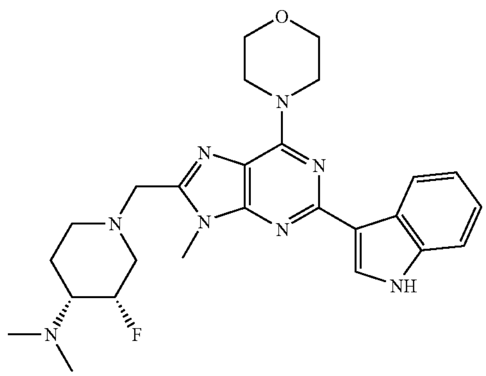 | (3S,4R)-1-((2-(1H-indol-3-yl)-9-methyl-6-morpholino-9H-purin-8-yl)methyl)-3-fluoro-N,N-dimethylpiperidin-4-amine |
| 123 | 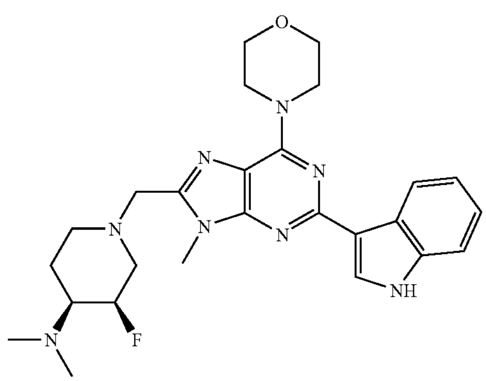 | (3R,4S)-1-((2-(1H-indol-3-yl)-9-methyl-6-morpholino-9H-purin-8-yl)methyl)-3-fluoro-N,N-dimethylpiperidin-4-amine |
| 124 | 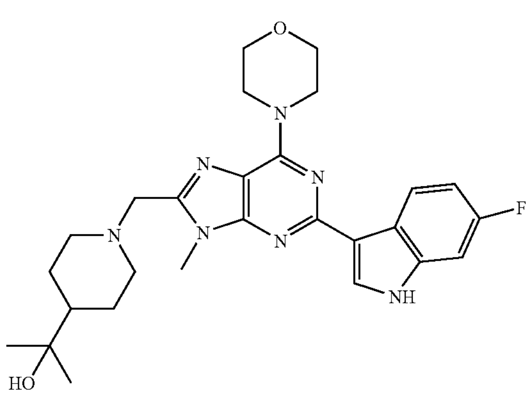 | 2-(1-((2-(6-fluoro-1H-indol-3-yl)-9-methyl-6-morpholino-9H-purin-8-yl)methyl)piperidin-4-yl)propan-2-ol |

TABLE 1-continued

| No. | Structure | Name |
|---|---|---|
| 125 | 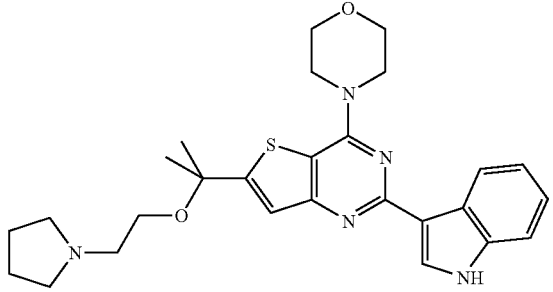 | 4-(2-(1H-indol-3-yl)-6-(2-(2-(pyrrolidin-1-yl)ethoxy(propan-2-yl)thieno[3,2-d]pyrimidin-4-yl)morpholine |
| 126 | 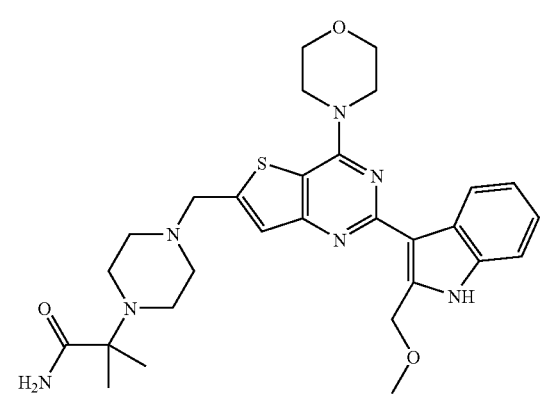 | 2-(4-((2-(2-(methoxymethyl)-1H-indol-3-yl)-4-morpholinothieno[3,2-d]pyrimidin-6-yl)methyl)piperazin-1-yl)-2-methylpropanamide |
| 127 | 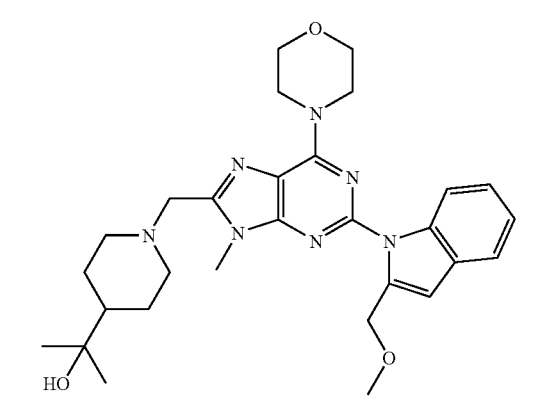 | 2-(1-((2-(2-(methoxymethyl)-1H-indol-1-yl)-9-methyl-6-morpholino-9H-purin-8-yl)methyl)piperidin-4-yl)propan-2-ol |
| 128 | 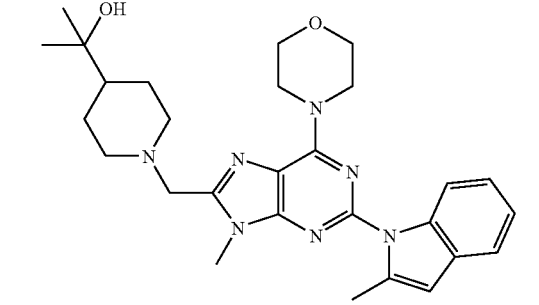 | 2-(1-((9-methyl-2-(2-methyl-1H-indol-1-yl)-6-morpholino-9H-purin-8-yl)methyl)piperidin-4-yl)propan-2-ol |

| No. | Structure | Name |
|---|---|---|
| 129 | 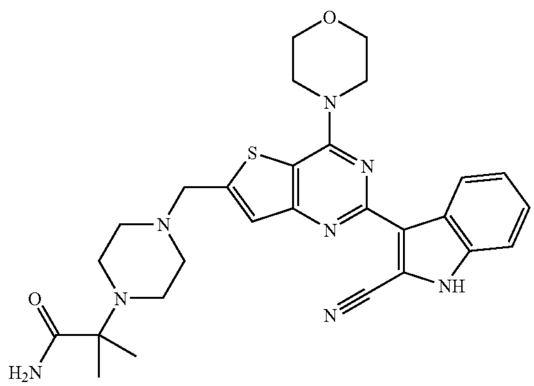 | 2-(4-((2-(2-cyano-1H-indol-3-yl)-4-morpholinothieno[3,2-d]pyrimidin-6-yl)methyl)piperazin-1-yl)-2-methylpropanamide |
| 130 | 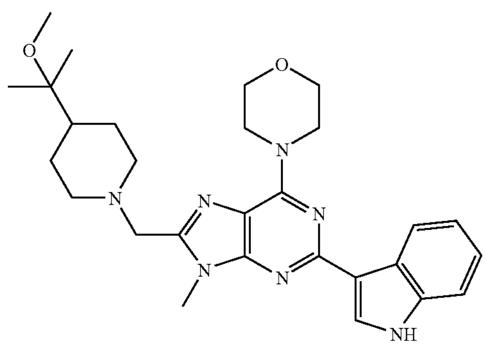 | 4-(2-(1H-indol-3-yl)-8-((4-(2-methoxypropan-2-yl)piperidin-1-yl)methyl)-9-methyl-9H-purin-6-yl)morpholine |
| 131 | 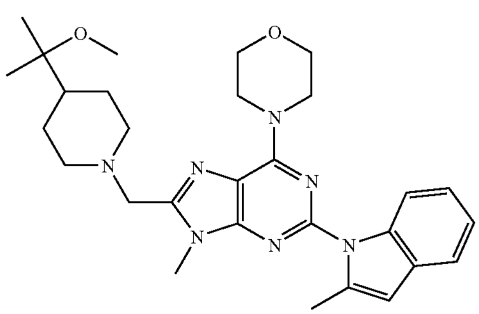 | 4-(8-((4-(2-methoxypropan-2-yl)piperidin-1-yl)methyl)-9-methyl-2-(2-methyl-1H-indol-1-yl)-9H-purin-6-yl)morpholine |
| 132 | 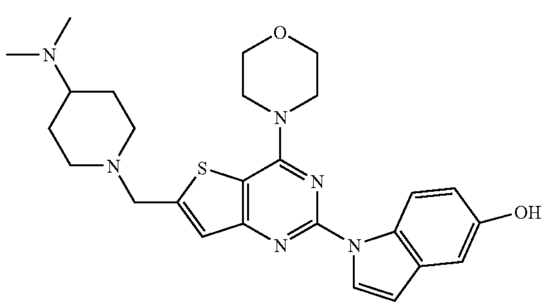 | 1-(6-((4-(dimethylamino)piperidin-1-yl)methyl)-4-morpholinothieno[3,2-d]pyrimidin-2-yl)-1H-indol-5-ol |

TABLE 1-continued

| No. | Structure | Name |
|---|---|---|
| 133 | 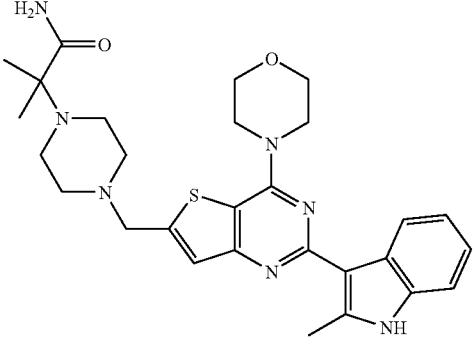 | 2-methyl-2-(4-((2-(2-methyl-1H-indol-3-yl)-4-morpholinothieno[3,2-d]pyrimidin-6-yl)methyl)piperazin-1-yl)propanamide |
| 134 | 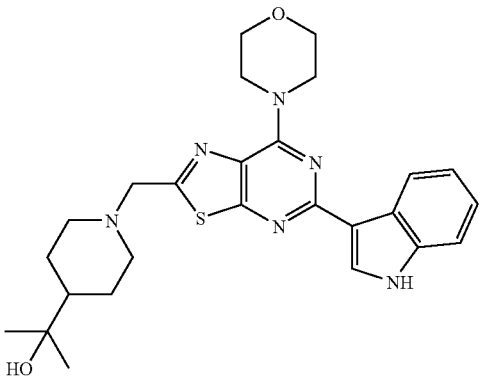 | 2-(1-((5-(1H-indol-3-yl)-7-morpholinothiazolo[5,4-d]pyrimidin-2-yl)methyl)piperidin-4-yl)propan-2-ol |
| 135 | 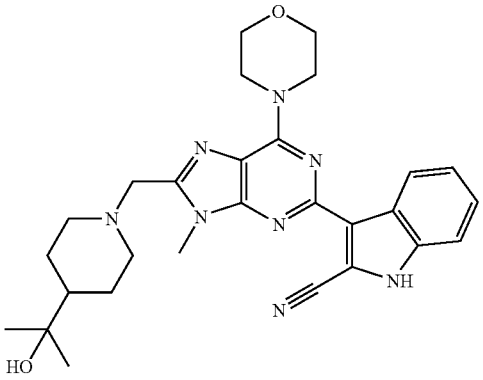 | 3-(8-((4-(2-hydroxypropan-2-yl)piperidin-1-yl)methyl)-9-methyl-6-morpholino-9H-purin-2-yl)-1H-indole-2-carbonitrile |
| 136 | 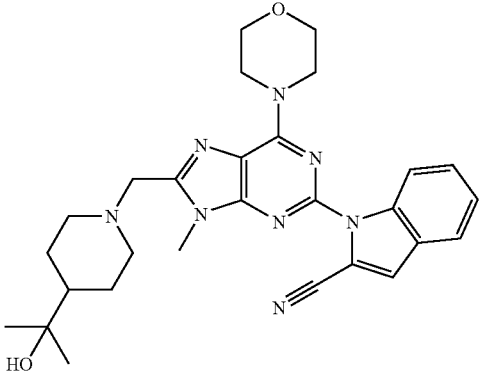 | 1-(8-((4-(2-hydroxypropan-2-yl)piperidin-1-yl)methyl)-9-methyl-6-morpholino-9H-purin-2-yl)-1H-indole-2-carbonitrile |

TABLE 1-continued

| No. | Structure | Name |
|---|---|---|
| 137 | 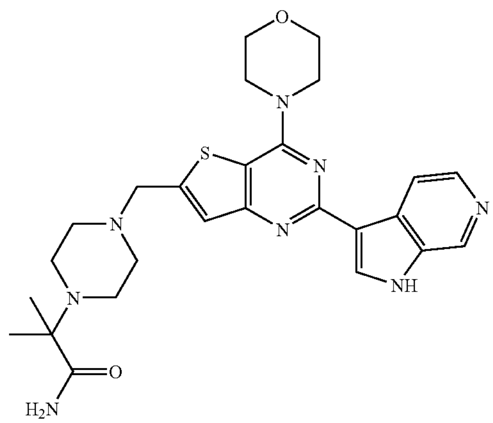 | 2-methyl-2-(4-((4-morpholino-2-(1H-pyrrolo[2,3-c]pyridin-3-yl)thieno[3,2-d]pyrimidin-6-yl)methyl)piperazin-1-yl)propanamide |

Administration of Formula I Compounds

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating a human or animal patient suffering from a disease or disorder arising from abnormal cell growth, function or behavior associated with PI3 kinase, in particular with the p110δ (delta) isoform of PI3 kinase such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Formula I compounds may be useful for in vitro, in situ, and in vivo diagnosis or treatment of mammalian cells, organisms, or associated pathological conditions, such as systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Methods of the invention also include treating such diseases as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated opthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as chronic inflammatory bowel disease (CIBD), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjögren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

The methods of the invention can have utility in treating subjects who are or can be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of PI3K delta activity may result in reduced amounts of reperfusion injury in such situations.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as inflammation or a hyperproliferative disorder (e.g., cancer). In certain embodiments, a compound of Formula I is combined in a pharmaceutical combination formulation, or dosing regimen as combination therapy, with a second therapeutic compound that has anti-inflammatory or anti-hyperproliferative properties or that is useful for treating an inflammation, immune-response disorder, or hyperproliferative disorder (e.g., cancer). The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, tautomer, solvate, metabolite, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, or a stereoisomer, tautomer, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, tautomer, solvate, metabolite, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^3H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I, or a stereoisomer, tautomer, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula Ia and Ib Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

In certain embodiments, thiazolopyrimidine compounds of Formula I ($X^1$ is N and $X^2$ is S) may be readily prepared using procedures well-known to prepare thiazoles, pyrimidines, and thiazolopyrimidines (U.S. Pat. No. 6,608,053; U.S. Pat. No. 6,492,383; U.S. Pat. No. 6,232,320; U.S. Pat. No. 6,187,777; U.S. Pat. No. 3,763,156; U.S. Pat. No. 3,661,908; U.S. Pat. No. 3,475,429; U.S. Pat. No. 5,075,305; US 2003/220365; GB 1390658; GB 1393161; WO 93/13664).

In certain embodiments, purine compounds of Formula I ($X^1$ is N and $X^2$ is $NR^2$) may be readily prepared using well-known procedures to prepare purines (Hammarstrom et al (2007) Tetrahedron Lett. 48(16):2823-2827; Cerna et al (2006) Organic Letters 8(23):5389-5392; Chang et al (2006) J. Med. Chem. 49(10):2861-2867; Yang et al (2005) J. Comb. Chem. 7:474-482; Liu et al (2005) J. Comb. Chem. 7:627-636; Hocek et al (2004) Synthesis 17:2869-2876; Hammarstrom et al (2003) Tetrahedron Lett. 44:8361-8363; Hammarstrom et al (2002) Tetrahedron Lett. 43:8071-8073; Booth et al (1987) J. Chem. Soc, Perkin Trans. 1: Organic and Bio-Organic Chem. 7:1521-1526; Booth et al (1981) J. Chem. Soc., Chemical Communications 15:788-789; Yoneda et al (1976) J. Chem. Soc., Perkin Trans. 1: Organic and Bio-Organic Chem. 14:1547-1550; Taylor et al (1971) J. Org. Chem. 36(21):3211-3217; Lister, J. H.; Fenn, M. D. The Purines, Supplementary 1, John Wiley & Sons, 1996, Volume 54; The Chemistry of Heterocyclic Compounds, Editors Weissberger, A.; Taylor E. C., Wiley Interscience, 1971, Volume 24; Legraverend, M.; Grierson, D. S. (2006) Bioorg. Med. Chem. 14:3987-4006; Hocek, M. (2003) Eur. J. Org. Chem. 245-254; U.S. Pat. No. 7,122,665; U.S. Pat. No. 6,743,919; U.S. Pat. No. 5,332,744; U.S. Pat. No. 4,728,644; U.S. Pat. No. 3,016,378; US 2008/0058297; US 2003/0139427; WO 2008/043031).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, 3rd Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

A purine compound may be prepared by using 2,4,8-trichloropurine as a starting material. The three chloro groups can be displaced by various substituents. More specifically, the most reactive chloro group (i.e., chloro at position 4) is substituted with a morpholino group to form morpholinopurine.

For illustrative purposes, Scheme 1 shows a general method for preparing Formula I purine compounds, as well as key intermediates. For a more detailed description of the individual reaction steps, see the General Procedures and Examples sections. Those skilled in the art will appreciate that other synthetic routes may be used to synthesize the inventive compounds. Although specific starting materials and reagents are depicted and discussed in the General Procedures and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

General Preparative Procedures
General Procedure A C-2 Suzuki Coupling

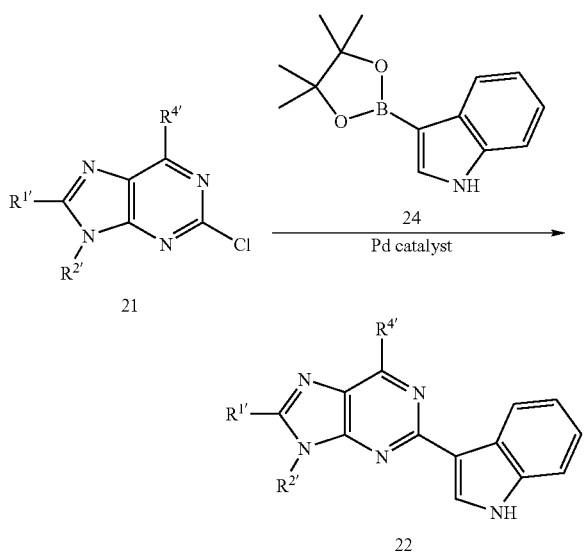

The Suzuki-type coupling reaction is useful to attach an indole or indole-analog at the 2-position of the pyrimidine ring of a 2-chloro-purine 21. The Suzuki-type coupling reaction is useful to attach a fused bicyclic heterocycle or a fused bicyclic heteroaryl at the 2-position of the pyrimidine ring of thiazolopyrimidines (i), thienopyrimidines (ii), furanopyrimidines (iv), and pyrrolopyrimidines (v). For example, 21 may be combined with about 1.5 equivalents of 3-(4,4,5,5-tetramethyl-1,3,2-dioxaborolan-2-yl)-1H-indole 24, and dissolved in 3 equivalents of sodium carbonate as a 1 molar solution in water and an equal volume of acetonitrile. A catalytic amount, or more, of a low valent palladium reagent, such as bis(triphenylphosphine)palladium(II) dichloride, is added. A variety of boronic acids or boronic esters can be used in place of the indazole boronic ester indicated. Also alternatively, a nitrogen of the fused bicyclic heterocycle or a fused bicyclic heteroaryl may be protected, for example as N-THP. In some cases potassium acetate was used in place of sodium carbonate to adjust the pH of the aqueous layer. The reaction is then heated to about 140-150° C. under pressure in a microwave reactor such as the Biotage Optimizer (Biotage, Inc.) for 10 to 30 minutes. The contents are extracted with ethyl acetate, or another organic solvent. After evaporation of the organic layer the Suzuki coupling products 22 may be purified on silica or by reverse phase HPLC. Substituents $R^{1'}$, $R^{2'}$, $R^{4'}$ may be $R^1$, $R^2$, $R^4$ as defined, or protected forms or precursors thereof.

A variety of palladium catalysts can be used during the Suzuki coupling step to form compounds, including exemplary embodiments 22. Suzuki coupling is a palladium mediated cross coupling reaction of a heteroarylhalide, such as 21, with a boronic acid such as 24. Low valent, Pd(II) and Pd(0) catalysts may be used in the Suzuki coupling reaction, including PdCl2(PPh$_3$)$_2$, Pd(t-Bu)$_3$, PdCl$_2$ dppf CH$_2$Cl$_2$, Pd (PPh$_3$)$_4$, Pd(OAc)/PPh$_3$, Cl$_2$Pd[(Pet$_3$)]$_2$, Pd(DIPHOS)$_2$, Cl$_2$Pd(Bipy), [PdCl(Ph$_2$PCH$_2$PPh$_2$)]$_2$, Cl$_2$Pd[P(o-tol)$_3$]$_2$, Pd$_2$(dba)$_3$/P(o-tol)$_3$, Pd$_2$(dba)/P(furyl)$_3$, Cl$_2$Pd[P(furyl)$_3$]$_2$, Cl$_2$Pd(PMePh$_2$)$_2$, Cl$_2$Pd[P(4-F-Ph)$_3$]$_2$, Cl$_2$Pd[P(C$_6$F$_6$)$_3$]$_2$, Cl$_2$Pd[P(2-COOH-Ph)(Ph)$_2$]$_2$, Cl$_2$Pd[P(4-COOH-Ph)(Ph)$_2$]$_2$, and encapsulated catalysts Pd EnCat™ 30, Pd EnCat™ TPP30, and Pd(II) EnCat™ BINAP30 (US 2004/0254066).

General Procedure B C-6 Nitrogen Substitution

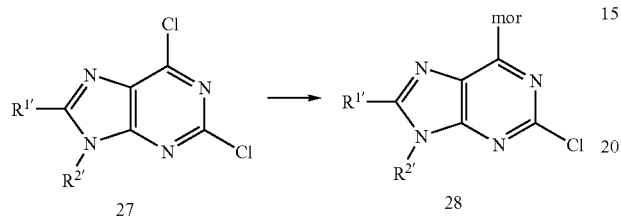

To a 2,6-dichloro purine intermediate 27 in a solvent such as ethanol is added a morpholine or a morpholine analog, and a non-nucleophilic base such as triethylamine (NEt$_3$, 1.5 eq, 63 µl). Alternatively, acetonitrile may be used as the solvent and potassium carbonate may be used as the base. The reaction mixture is stirred at room temperature for about 1 hour or overnight, volatiles removed in vacuo and residue partitioned between DCM and brine. If the mixture is insoluble it may be sonicated and the solid product was collected by filtration. Drying with magnesium sulfate and evaporation of the solvent gives N'-(2-chloro purin-6-yl)-amine substituted intermediate 28, often as a crystalline solid, or by trituration. Substituents R$^{1'}$ and R$^{2'}$ may be R$^1$ and R$^2$ as defined, or protected forms or precursors thereof.

General Procedure C N-9 Nitrogen Alkylation

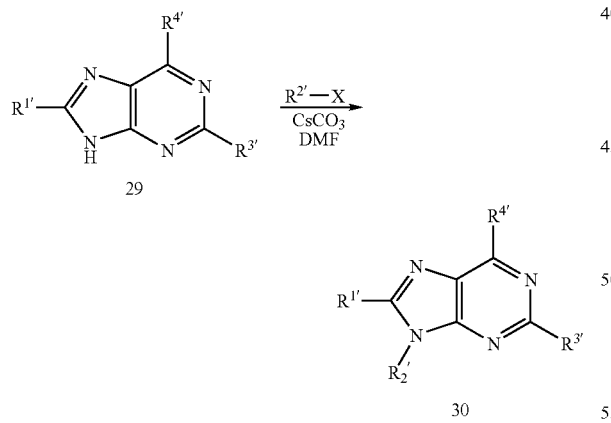

9-H Purine intermediate 29 is brought up into DMF and 2 equiv of cesium carbonate is added to the reaction mixture. The reaction is heated to 50° C. whereupon 1 to 3 equivalents of an alkyl halide R$^{2'}$—X are added to the reaction mixture. The reaction is monitored by TLC or LC/MS and stirred until completion, typically several hours. The reaction mixture is extracted with EtOAc and water, and the organic layer is dried, filtered and concentrated to get crude 9-alkylated purine 30 which is used directly in the next reaction or purified by reverse phase HPLC. Substituents R$^{1'}$, R$^{3'}$ and R$^{4'}$ may be R$^1$, R$^3$ and R$^4$ as defined, or protected forms or precursors thereof.

General Procedure D THP Deprotection

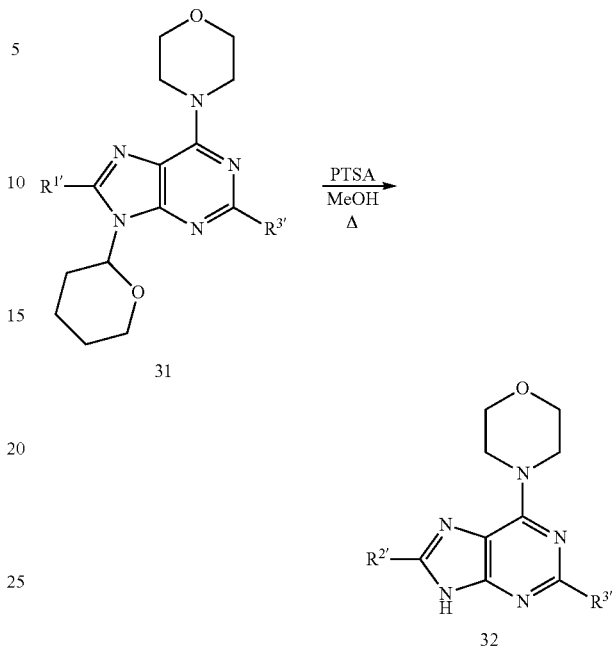

Generally, N-9-tetrahydropyranyl substituted 31 may be treated with catalytic amounts of para-toluenesulfonic acid (PTSA) in a solution of methanol and heated to about 50° C. until the tetrahydropyran (THP) group is removed to afford compound 32. The reaction may be monitored by LC-MS or TLC. Substituents R$^{1'}$ and R$^{3'}$ may be R$^1$ and R$^3$ as defined, or protected forms or precursors thereof.

General Procedure E Displacement of Alkyl Bromide with Amines:

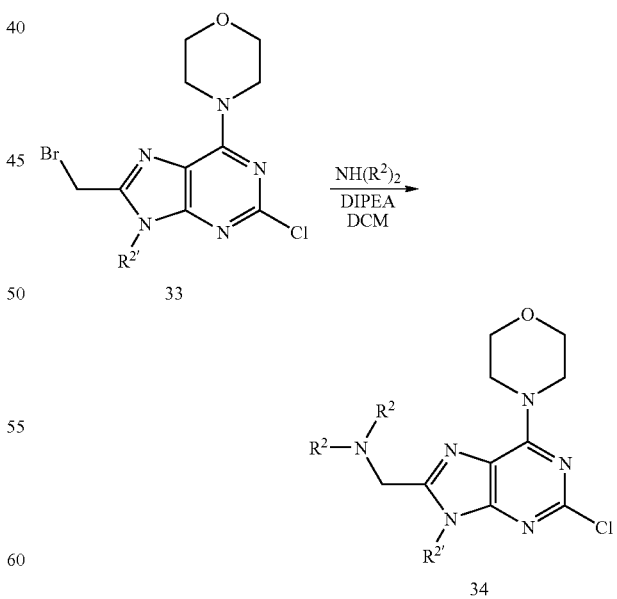

Generally, substituted 33 is suspended in dichloromethane whereupon 3 equivalents of Hunig's base (DIPEA) and 1.5 equivalents of an amine (NH(R$^2$)$_2$) are added to the reaction mixture. The reaction is monitored by TLC or LC-MS until complete, usually within 30 minutes. The reaction mixture is extracted with water and the organic layer is dried, filtered and concentrated to dryness. The intermediate 34 can be taken as crude into subsequent reactions or in some cases is purified by column chromatography.

General Procedure F Amide Coupling

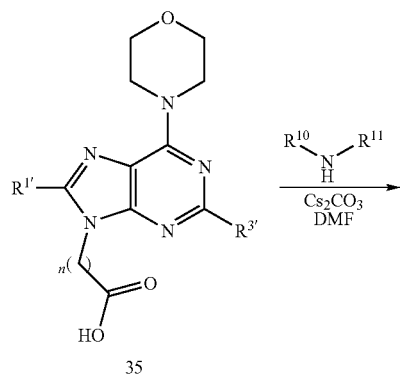

35

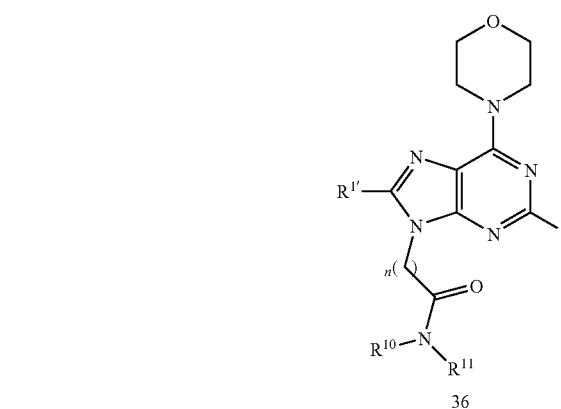

36

A 2,6,8 substituted, 9-alkylcarboxyl purine 35, where n is 1 to 12, is treated with 1.5 eq HATU (2-(7-aza-1H-benzotriazole-1-yl)-1,3,3-tetramethyluronium hexafluorophosphate), an excess (such as 3 eq) of an alkylamine (HNR$^{10}$R$^{11}$) and an excess (such as 3 eq) of cesium carbonate in dimethylformamide (DMF). Alternatively, other coupling reagents may be used. The reaction is stirred until complete and extracted in ethylacetate with saturated bicarbonate solution. The organic layer is dried, filtered and concentrated to yield the acylated, crude intermediate, which is purified via reverse phase HPLC to yield product 36. Substituents R$^{1'}$ and R$^{3'}$ may be R$^{1}$ and R$^{3}$ as defined, or protected forms or precursors thereof.

General Procedure G Stille Coupling

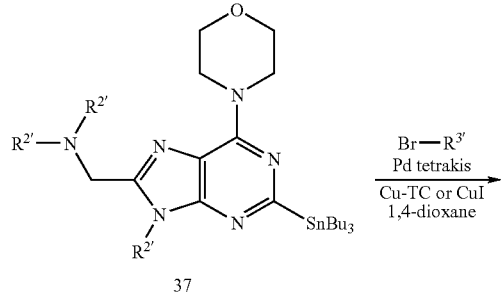

37

-continued

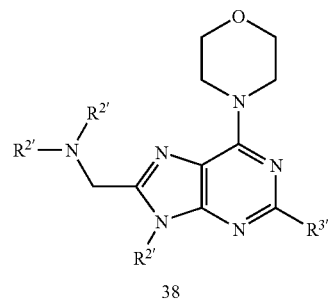

38

To intermediate 37 in a microwave vial is added 1.2 equivalents of an aryl bromide, 1 equivalent of copper (I) iodide or copper thiophene-carboxylate, and 1,4-dioxane as solvent. The reaction mixture is degassed under nitrogen for 5 minutes prior to addition of 0.12 equivalents of tetrakis(triphenylphosphine)palladium(0). The reaction is heated in a CEM or Biotage microwave for 20-30 minutes at 140° C. The crude reaction mixture is filtered and periodically passed through a Biotage Isolute scx-2 basic spe cartridge before being purified via normal or reverse phase chromatography to afford pure product 38. Substituents R$^{2'}$ and R$^{3'}$ may be R$^{2}$ and R$^{3}$ as defined, or protected forms or precursors thereof.

General Procedure H N-9 Alkylation of Purines

Scheme 1 shows a general method for preparation of polyfunctionalized purines begins with protection of the N-9 nitrogen of 2,6-dichloro-9H-purine as the tetrahydropyranyl group (THP). Displacement of the more reactive chloro group with morpholine gives 4-(2-chloro-9-(tetrahydro-2H-pyran-2-yl)-9H-purin-6-yl)morpholine. The C-8 proton is removed with strong base and reacted with various electrophiles (R$^{1}$). After deprotection with mild acid, N-9 is alkylated of N-9 with various electrophiles (R$^{2}$). Suzuki coupling at C-2 chloro by General Procedure A with various boronate reagents and palladium catalysts gives carbon-linked indole and indole-analogs as R$^{3}$.

Scheme 1

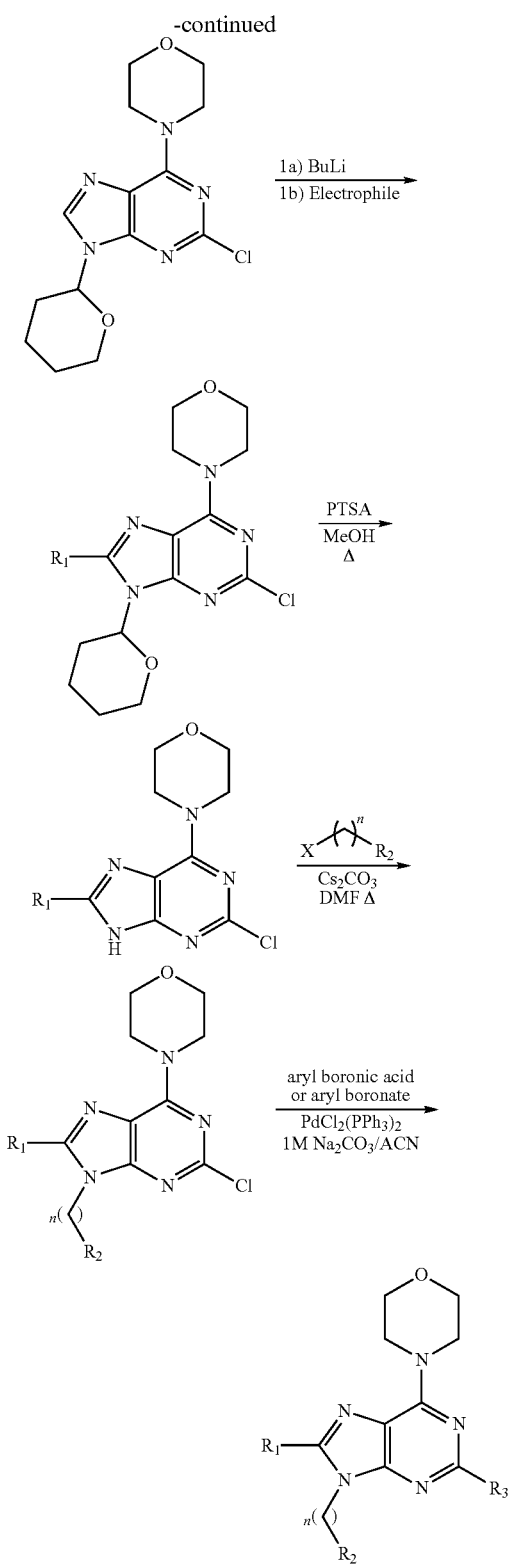

EXAMPLES

The chemical reactions described in the Examples may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting reactive functional groups, by utilizing other suitable reagents known in the art other than those described, and/or by making routine modifications of reaction conditions. Alternatively, other reactions disclosed herein or known in the art will be recognized as having applicability for preparing other compounds of the invention.

$^1$H NMR spectra were recorded at ambient temperature using a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography-Mass Spectrometry (LCMS) experiments to determine retention times ($R_T$) and associated mass ions were performed using one of the following methods. The spectrometers have an electrospray source operating in positive and negative ion mode. Additional detection was achieved using a Sedex 85 evaporative light scattering detector.

Method A: Experiments performed on a Waters Platform LC quadrupole mass spectrometer linked to a Hewlett Packard HP1100 LC system, with diode array detector and a 100 position autosampler, using a Phenomenex Luna 3 μm $C_{18}$(2) 30×4.6 mm and a 2 mL/minute flow rate. The mobile phase consisted of formic acid 0.1% in water (solvent A) and formic acid 0.1% in methanol (solvent B). The initial solvent system was 95% solvent A and 5% solvent B for the first 0.5 minute followed by a gradient up to 5% solvent A and 95% solvent B over the next 4 minutes. The final solvent system was held constant for a further 1 minute.

Method B: Experiments performed on a Waters Platform LC quadrupole mass spectrometer linked to a Hewlett Packard HP1100 LC system, with diode array detector and a 100 position autosampler, using a using a Phenomenex Luna 3 μm $C_{18}$(2) 30×4.6 mm and a 2 mL/minute flow rate The mobile phase consisted of formic acid 0.1% in water (solvent A) and formic acid 0.1% in acetonitrile (solvent B). The initial solvent system was 95% solvent A and 5% solvent B for the first 0.50 minute followed by a gradient up to 5% solvent A and 95% solvent B over the next 4 minutes. The final solvent system was held constant for a further 1 minute.

Method C: Experiments performed on a Waters ZMD quadrupole mass spectrometer linked to a Waters 1525 LC system, with a Waters 996 diode array detector and a Waters 2700 autosampler, using a Phenomenex Luna 3 μm $C_{18}$(2) 30×4.6 mm and a 2 mL/minute flow rate. The mobile phase consisted of formic acid 0.1% in water (solvent A) and formic acid 0.1% in methanol (solvent B). The initial solvent system was 95% solvent A and 5% solvent B for the first 0.5 minute followed by a gradient up to 5% solvent A and 95% solvent B over the next 4 minutes. The final solvent system was held constant for a further 1 minute.

Method D: Experiments performed on a Waters ZMD quadrupole mass spectrometer linked to a Waters 1525 LC system, with a Waters 996 diode array detector and a Waters 2700 autosampler, using a Phenomenex Luna 3 μm $C_{18}$(2) 30×4.6 mm and a 2 mL/minute flow rate. The mobile phase consisted of formic acid 0.1% in water (solvent A) and formic acid 0.1% in acetonitrile (solvent B). The initial solvent system was 95% solvent A and 5% solvent B for the first 0.5 minute followed by a gradient up to 5% solvent A and 95% solvent B over the next 4 minutes. The final solvent system was held constant for a further 1 minute.

Method E: Experiments performed on a Waters Micromass ZQ2000 quadrupole mass spectrometer linked to a Hewlett Packard HP1100 LC system, with a DAD UV detector and a CTC HTS PAL autosampler, using a Higgins Clipeus 5 μm C18 100×3.0 mm column (at 40° C.) and a 1 mL/minute flow rate. The mobile phase consisted of formic acid 0.1% in water (solvent A) and formic acid 0.1% in methanol (solvent B). The initial solvent system was 85% solvent A and 15% solvent B for the first 1 minute followed by a gradient up to 5% solvent A and 95% solvent B over the next 12 minutes. The final solvent system was held constant for a further 7 minutes.

Method F: Experiments performed on a Waters Micromass ZQ2000 quadrupole mass spectrometer linked to a Hewlett Packard HP1100 LC system, with a DAD UV detector and a CTC HTS PAL autosampler, using a Higgins Clipeus 5 micron $C_{18}$ 100×3.0 mm column and a 1 mL/minute flow rate. The mobile phase consisted of formic acid 0.1% in water (solvent A) and formic acid 0.1% in acetonitrile (solvent B). The initial solvent system was 85% solvent A and 15% solvent B for the first 1 minute followed by a gradient up to 5% solvent A and 95% solvent B over the next 14 minutes. The final solvent system was held constant for a further 5 minutes.

Microwave experiments were carried out using a CEM Explorer, Smith Synthesizer or a Biotage Initiator™, which uses a single-mode resonator and dynamic field tuning, both of which give reproducibility and control. Temperatures from 40-250° C. can be achieved and pressures up to 20 bar can be reached.

Unless otherwise stated, all reactions were performed under an inert, i.e. argon or nitrogen, atmosphere.

Example 1

2,6-dichloro-9-methyl-9H-purine 4

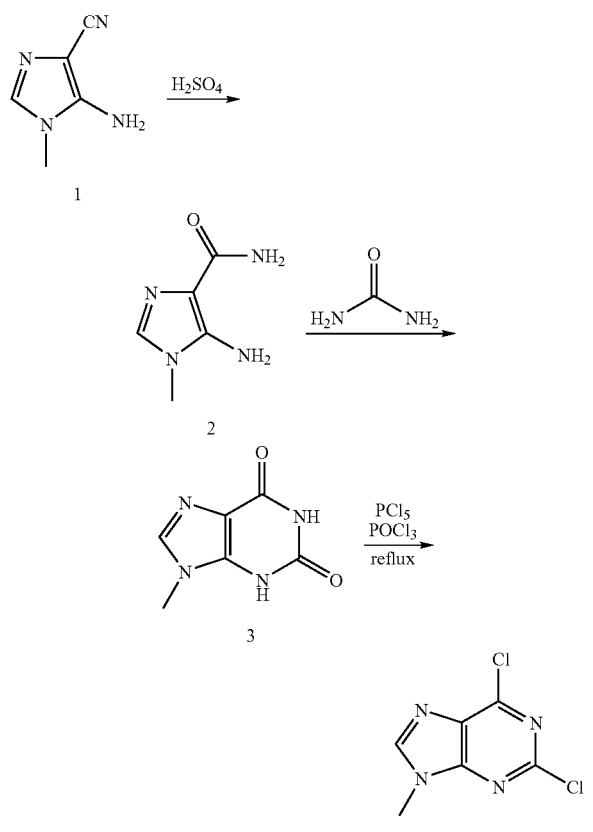

The cyano group of 5-amino-1-methyl-1H-imidazole-4-carbonitrile 1 is hydrolyzed with sulfuric acid to give 5-amino-1-methyl-1H-imidazole-4-carboxamide 2. Cyclization with urea gives 9-methyl-1H-purine-2,6(3H,9H)-dione 3. Chlorination with phosphorus pentachloride and phosphorusoxychloride gives 2,6-dichloro-9-methyl-9H-purine 4 (CAS Registry 2382-10-7).

Example 2

5-Chloro-7-morpholin-4-yl-2-(3-morpholin-4-ylazetidin-1-ylmethyl)thiazolo[5,4-d]pyrimidine

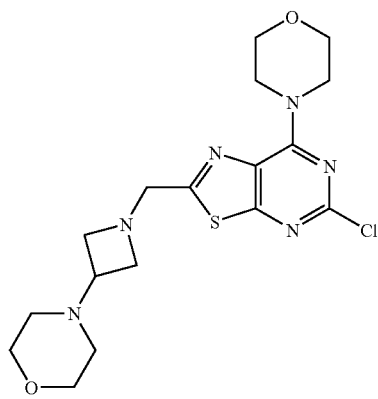

A solution of 5-chloro-7-morpholin-4-yl-thiazolo[5,4-d]pyrimidine-2-carbaldehyde (3.0 g, 10.54 mmol) and 4-azetidin-3-ylmorpholine (1.8 g, 12.66 mmol) in DCE (200 mL) was stirred at ambient temperature for 2 h. Sodium triacetoxyborohydride (3.5 g, 16.5 mmol) was added and the mixture stirred for 18 h, then loaded onto an Isolute® SCX-2 cartridge (50 g). The cartridge was then washed with MeOH and the desired product was subsequently eluted using 2 M $NH_3$ in MeOH. The eluent was collected and concentrated in vacuo. The resultant residue was purified by flash chromatography (Si-PPC, DCM: MeOH 100:0 to 99:1 to 98:2 to 95:5) to afford the title compound as a cream solid (2.66 g, 61%). LCMS (Method C): $R_T$=2.68 min, $[M+H]^+$ 411.3

Example 3

9-(2-Chloro-4-morpholin-4-yl-thieno[3,2-d]pyrimidin-6-ylmethyl)-1-oxa-4,9-diazaspiro[5.5]undecan-3-one

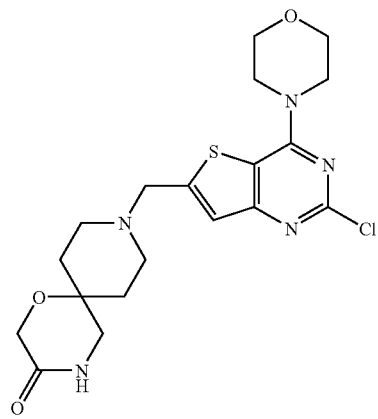

A solution of 6-bromomethyl-2-chloro-4-morpholin-4-yl-thieno[3,2-d]pyrimidine (500 mg, 1.43 mmol), 1-oxa-4,9-diaza-spiro[5.5]undecan-3-one (315 mg, 1.85 mmol) and potassium carbonate (450 mg, 3.26 mmol) in DMF (40 mL) was stirred at ambient temperature for 18 hours, then loaded onto an Isolute® SCX-2 cartridge (10 g). The cartridge was washed with MeOH and the desired product was subsequently eluted using 2 M $NH_3$ in MeOH. The eluent was collected and concentrated in vacuo. The resultant residue was purified by flash chromatography (Si-PPC, DCM:MeOH 100:0 to 98:2 to 95:5) to afford the title compound as a white solid (515 mg, 82%). LCMS (Method A): R$_T$=2.51 min, [M+H]$^+$ 438.1

Example 4

2-[4-(4-Morpholin-4-yl-2-(tributylstannanyl)thieno[3,2-d]pyrimidin-6-ylmethyl)-piperazin-1-yl]isobutyramide

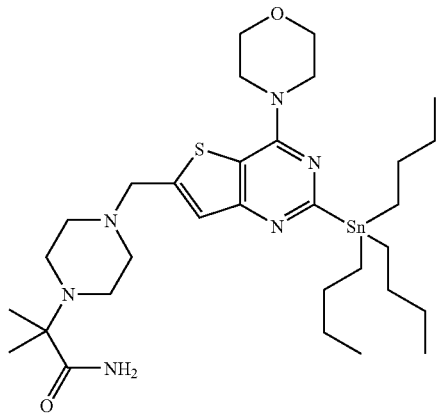

A mixture of 2-[4-(2-chloro-4-morpholin-4-yl-thieno[3,2-d]pyrimidin-6-ylmethyl)-piperazin-1-yl]isobutyramide (1.0 g, 2.3 mmol), hexabutylditin (1.4 mL, 2.7 mmol), and PdCl$_2${P$^t$Bu$_2$(Ph-p-NMe$_2$)}$_2$ (161 mg, 0.2 mmol) in dioxane (10 mL) was degassed and then subjected to microwave irradiation at 150° C. for 30 min. The reaction mixture was diluted with MeOH and loaded onto a Isolute® SCX-2 cartridge (25 g). The cartridge was then washed with MeOH and the desired product was subsequently eluted using 2 M NH$_3$ in MeOH. Appropriate fractions were combined and concentrated to give a residue which was subjected to flash chromatography (Si-PPC, MeOH:DCM, gradient 0:100 to 10:90). Appropriate fractions were combined and concentrated to give the title compound as white foam (0.9 g, 56%). LCMS (Method C)R$_T$=3.88 min; [M+H]$^+$ 693.1 ($^{116}$Sn) 695.1 ($^{118}$Sn)

Example 5

2-[4-(7-Morpholin-4-yl-5-(tributylstannanyl)thiazolo[5,4-d]pyrimidin-2-ylmethyl)-piperazin-1-yl]isobutyramide

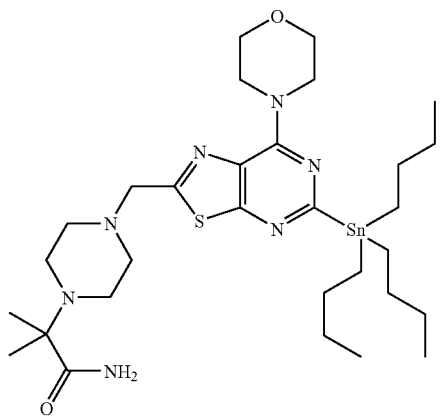

A mixture of 2-[4-(5-chloro-7-morpholin-4-yl-thiazolo[5,4-d]pyrimidin-2-ylmethyl)-piperazin-1-yl]-isobutyramide (1.0 g, 2.2 mmol), hexabutylditin (1.4 mL, 2.7 mmol), and PdCl$_2${P$^t$Bu$_2$(Ph-p-NMe$_2$)}$_2$ (161 mg, 0.2 mmol) in dioxane (10 mL) was degassed and then subjected to microwave irradiation at 150° C. for 30 min. The reaction mixture was diluted with MeOH and loaded onto an Isolute® SCX-2 cartridge (25 g). The cartridge was then washed with MeOH and the desired product was subsequently eluted using 2 M NH$_3$ in MeOH. Appropriate fractions were combined and concentrated to give a residue which was subjected to flash chromatography (Si-PPC, MeOH:DCM, gradient 0:100 to 10:90). Appropriate fractions were combined and concentrated to give the title compound as a yellow oil (1.1 g, 67%). LCMS (Method C) R$_T$=4.83 min; [M+H]$^+$694.1 ($^{116}$Sn) 696.1 ($^{118}$Sn)

Example 6

2-[4-(2-Chloro-7-methyl-4-morpholin-4-yl-thieno[3,2-c]pyrimidin-6-ylmethyl)piperazin-1-yl]isobutyramide

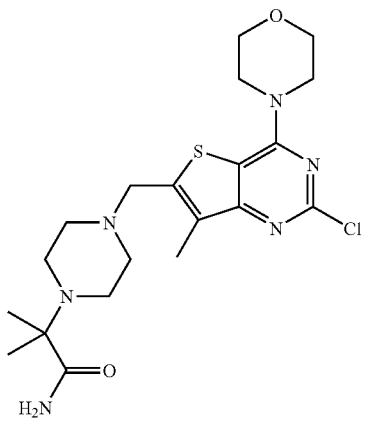

To a solution of 2-chloro-7-methyl-4-morpholin-4-yl-thieno[3,2-c]pyrimidine-6-carbaldehyde (1.00 g, 3.36 mmol) in DCE (50 mL) was added 2-(piperazin-1-yl)isobutyramide (630 mg, 3.69 mmol), trimethyl orthoformate (3.67 mL, 33.58 mmol) and acetic acid (0.19 mL, 3.36 mmol). After stirring at room temperature for 3 h sodium triacetoxyborohydride (1.10 g, 5.03 mmol) was added and the resulting mixture stirred for a further 17 h. The reaction mixture was loaded onto an Isolute® SCX-2 cartridge, washed with MeOH then eluted with 2 M NH$_3$ in MeOH/DCM. The resultant residue was triturated with MeOH to give the title compound as a white solid (1.12 g, 74%). LCMS (Method C): R$_T$=2.88 min, [M+H]$^+$ 453

Example 7

2-[4-(7-Methyl-4-morpholin-4-yl-2-(tributylstannanyl)thieno[3,2-c]pyrimidin-6-ylmethyl)piperazin-1-yl]isobutyramide

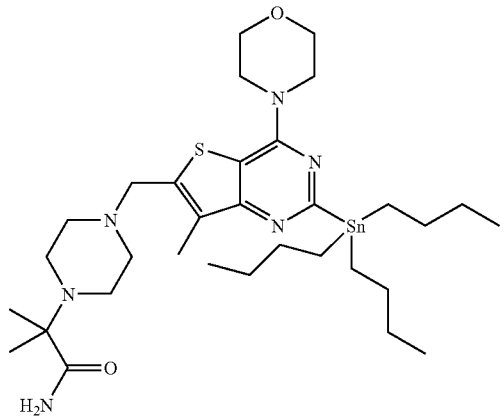

A mixture of 2-[4-(2-chloro-7-methyl-4-morpholin-4-yl-thieno[3,2-d]pyrimidin-6-ylmethyl)piperazin-1-yl]isobutyramide (194 mg, 0.43 mmol), hexabutylditin (373 mg, 0.64 mmol), PdCl$_2${P$^t$Bu$_2$(Ph-p-NMe$_2$)}$_2$ (30 mg, 10 mol %) in dioxane (2 mL) was purged with nitrogen gas then heated at 150° C., for 20 min, in a microwave reactor. The reaction mixture was loaded onto an Isolute® SCX-2 cartridge, washed with MeOH then eluted with 2M NH$_3$ in MeOH. The resulting residue was purified by column chromatography (Si-PPC, MeOH:DCM, gradient 0:100 to 05:95) to afford the title compound as a colorless oil (192 mg, 63%). LCMS (Method D): R$_T$ 2.92 min, [M+H]$^+$ 705 ($^{116}$Sn), 707 ($^{118}$Sn)

Example 8

2-(1-((2-chloro-9-methyl-6-morpholino-9H-purin-8-yl)methyl)piperidin-4-yl)propan-2-ol

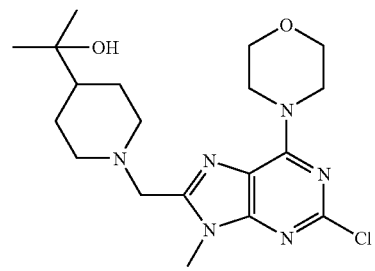

To 4-(2-chloro-9-(tetrahydro-2H-pyran-2-yl)-9H-purin-6-yl)morpholine (100 g) in methanol (500 mL) at 50° C. was added p-toluenesulfonic acid monohydrate (6 g). The reaction was stirred for 30 mins, whereupon white solid has crashed fully out of solution. The solid was filtered and collected through a Buchner funnel, rinsed with methanol and dried under vacuum to get 4-(2-chloro-9H-purin-6-yl)morpholine. Cesium carbonate (200 g) and iodomethane (30 mL) were subsequently added to a stirring solution of 4-(2-chloro-9H-purin-6-yl)morpholine in DMF at 50° C. The reaction was monitored by lc-ms until complete, about 30 minutes, whereupon the solvent was concentrated to dryness. Subsequent suspension of the crude reaction in water crashed out 4-(2-chloro-9-methyl-9H-purin-6-yl)morpholine (72 g) as a white solid, which was filtered and dried under vacuum overnight.

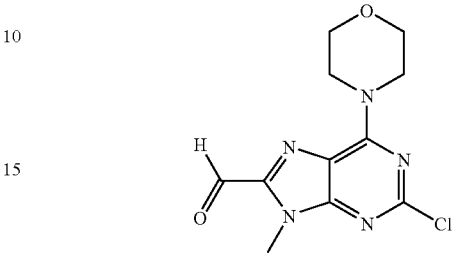

To stirred solution of 4-(2-chloro-9-methyl-9H-purin-6-yl)morpholine (10 g) and N,N,N',N'-tetramethylethylenediamine (9.0 mL) in tetrahydrofuran (200 mL) at −78° C. was added 2.5 M of n-butyllithium in tetrahydrofuran (35 mL). The solution was stirred at −40° C. for 30 minutes, and then re-cooled to −78° C., whereupon DMF (8 mL) was added and the reaction stirred for another hour. The reaction was quenched into cold 0.25N HCl solution via 10 mL serological pipet aliquots. Ice was added to keep quenching solution temperature below 5° C., to avoid formation of by-product during workup. 2-Chloro-9-methyl-6-morpholino-9H-purine-8-carbaldehyde (11 g) crashed out as a light yellow solid which was filtered, rinsed with water and dried under vacuum.

A solution of 2-chloro-9-methyl-6-morpholino-9H-purine-8-carbaldehyde (17.2 g) in MeOH (800 mL) at 0° C. was treated portion wise with sodium borohydride (5 g). The reaction was warmed to room temperature and stirred 15 minutes. The reaction mixture was quenched with saturated solution of sodium bicarbonate. The aqueous layer was extracted twice with ethyl acetate. The combined organic layers were dried over magnesium sulfate and concentrated in vacuo to yield crude 2-chloro-9-methyl-6-morpholino-9H-purin-8-yl)methanol (16.9 g) as a white solid.

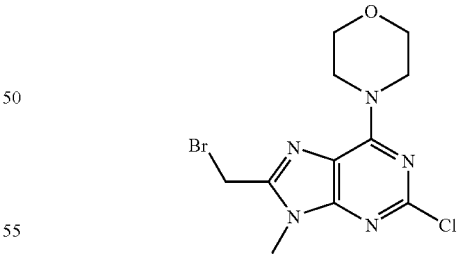

To a solution of crude 2-chloro-9-methyl-6-morpholino-9H-purin-8-yl)methanol (16.5 g) in a mixture of dichloroethane (600 mL) and THF (400 mL) at 0° C. was added phosphorus tribromide (11 mL) dropwise. The reaction was stirred for 1 h whereupon the solid that crashed out was filtered, rinsed with water, collected and dried to give 4-(8-(bromomethyl)-2-chloro-9-methyl-9H-purin-6-yl)morpholine (15.6 g) as a white solid.

2-(Piperidin-4-yl)propan-2-ol (0.73 g) was reacted with 4-(8-(bromomethyl)-2-chloro-9-methyl-9H-purin-6-yl)morpholine (1.6 g) via General Procedure C to yield 2-(1-((2-chloro-9-methyl-6-morpholino-9H-purin-8-yl)methyl)piperidin-4-yl)propan-2-ol (1.76 g) as a white solid.

Example 9

1-((2-(1H-indol-3-yl)-4-morpholinothieno[3,2-d]pyrimidin-6-yl)methyl)-N,N-dimethylpiperidin-4-amine 101

A microwave vessel was charged with [1-(2-chloro-4-morpholin-4-yl-thieno[3,2-d]pyrimidin-6-ylmethyl)-piperidin-4-yl]-dimethyl-amine (0.500 g, 1.26 mmol), 1-BOC-indole-3-yl-boronic acid (363 mg, 1.39 mmol), 1 N sodium carbonate solution (3 mL), acetonitrile (9 mL) and Pd(dppf)Cl$_2$ (103 mg. 0.126 mmol), then the mixture was degassed, sealed, and heated at 140° C. under microwave irradiation for 20 min. The reaction mixture was diluted with dichloromethane (100 mL) and 1 N sodium carbonate solution (10 mL) then the phases were separated. The organic phase was washed with saturated aqueous sodium bicarbonate solution (15 mL) then dried (MgSO$_4$) and concentrated in vacuo. Purification by chromatography (silica, 0 to 15% of a 9.5:0.5 MeOH:NH$_4$OH solution in dichloromethane) followed by trituration with hot ethanol afforded 101 (161 mg, 27%) as a cream powder. MS m/e 477 [M+H]$^+$. $^1$H NMR (400 MHz, CHCl$_3$-d) δ ppm 1.53-1.68 (m, 2H) 1.75 (br. s., 1H) 1.83 (d, J=11.6 Hz, 2H) 2.05-2.22 (m, 3H) 2.30 (s, 6H) 3.04 (d, J=12.1 Hz, 2H) 3.81 (s, 2H) 3.88-3.99 (m, 4H) 4.01-4.13 (m, 4H) 7.21-7.32 (m, 2H) 7.37-7.45 (m, 1H) 8.14 (d, J=2.5 Hz, 1H) 8.64-8.70 (m, 1H) 8.76 (br. s., 1H)

Example 10

1-((2-(indolin-1-yl)-4-morpholinothieno[3,2-d]pyrimidin-6-yl)methyl)-N,N-dimethylpiperidin-4-amine 102

A microwave vessel was charged with [1-(2-chloro-4-morpholin-4-yl-thieno[3,2-d]pyrimidin-6-ylmethyl)-piperidin-4-yl]-dimethyl-amine (0.2 g), indoline (0.12 g), p-toluenesulfonic acid (0.01 g), and DMF (3 mL). The vessel was sealed and heated at 150° C. under microwave irradiation for 4 h. The reaction mixture was cooled to room temperature and the solid precipitate was filtered and purified by chromatography (silica, 0 to 20% of a 49:1 MeOH:NH$_4$OH mixture in dichloromethane) to furnish the title compound (0.09 g, 38%) as an off-white solid. MS m/e 479 [M+H]$^+$; $^1$H NMR (300 MHz, DMSO-d$_6$) δ ppm 1.36-1.65 (m, 2H) 1.85 (d, J=11.30 Hz, 2H) 2.06 (t, J=10.74 Hz, 2H) 2.44 (br. s., 6H) 2.97 (d, J=11.30 Hz, 2H) 3.12 (t, J=8.48 Hz, 3H) 3.67-3.93 (m, 10H) 4.17 (t, J=8.67 Hz, 2H) 6.84 (t, J=7.35 Hz, 1H) 7.03-7.29 (m, 3H) 8.31 (d, J=7.91 Hz, 1H).

Example 11

1-((2-(1H-indol-1-yl)-4-morpholinothieno[3,2-d]pyrimidin-6-yl)methyl)-N,N-dimethylpiperidin-4-amine 103

A solution of indole (0.117 g) in DMF (8 mL) was cooled to 0° C. then sodium hydride (0.06 g) was added. After 15 min, [1-(2-chloro-4-morpholin-4-yl-thieno[3,2-d]pyrimidin-6-ylmethyl)-piperidin-4-yl]-dimethyl-amine (0.395 g) was added. The reaction flask was sealed, heated at 150° C. for 1 h, cooled to room temperature, and diluted with water. The solid precipitate was collected by filtration then purified by chromatography (silica, 0 to 20% of a 49:1 MeOH:NH$_4$OH mixture in dichloromethane) to furnish the title compound (0.156 g, 33%) as an off-white solid. MS m/e 477 [M+H]$^+$; $^1$H NMR (300 MHz, DMSO-d$_6$) δ ppm 1.27-1.57 (m, 2H) 1.55-1.79 (m, 2H) 1.95-2.13 (m, 3H) 2.16 (s, 6H) 2.75-3.06 (m, 2H) 3.74-3.89 (m, 6H) 3.91-4.08 (m, 4H) 6.71 (d, J=3.39 Hz, 1H) 7.18 (s, 1H) 7.30 (s, 1H) 7.36 (s, 1H) 7.61 (s, 1H) 8.30 (d, J=3.77 Hz, 1H) 8.78 (d, J=7.91 Hz, 1H)

Example 12

4-(1-((2-(1H-indol-3-yl)-9-methyl-6-morpholino-9H-purin-8-yl)methyl)piperidin-4-yl)morpholine 104

Step 1: 4-(1-((2-chloro-9-methyl-6-morpholino-9H-purin-8-yl)methyl)piperidin-4-yl)morpholine

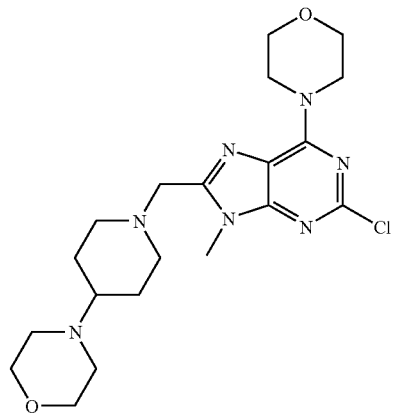

To a solution of 4-(8-(bromomethyl)-2-chloro-9-methyl-9H-purin-6-yl)morpholine (935 mg, 2.7 mmol) in DCM (30 mL) was added 4-morpholino-piperidine (505 mg, 2.97 mmol) and DIEA (0.70 mL). The resulting mixture was stirred at room temperature for 18 hours. The mixture was then poured onto water and the layers were separated. The aqueous layer was extracted with three times with DCM. The combined organic extracts were washed with water, dried over Na$_2$SO$_4$, filtered and concentrated. The crude product was then purified by flash chromatography (0-30% gradient MeOH in DCM) to give the title compound as a white solid (95%). LCMS: M+H$^+$=436.2.

Step 2: 4-(1-((9-methyl-6-morpholino-2-(1-(phenylsulfonyl)-1H-indol-3-yl)-9H-purin-8-yl)methyl)piperidin-4-yl)morpholine

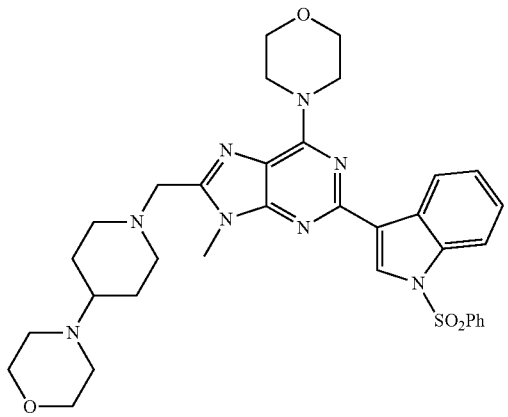

To a degassed suspension of 4-(1-((2-chloro-9-methyl-6-morpholino-9H-purin-8-yl)methyl)piperidin-4-yl)morpholine (249 mg, 0.571 mmol), 1-(phenylsulfonyl)-3-indoleboronic acid (189 mg, 0.628 mmol), 2M Na₂CO₃ aqueous solution (0.571 mL, 1.0 mmol) in toluene (5 mL) and ethanol (2 mL) was added Pd(PPh₃)₄ (33 mg, 0.029 mmol). The suspension was then stirred under nitrogen at 100° C. for 18 hours. The reaction mixture was then diluted with EtOAc and water. The layers were separated. The aqueous layer was extracted three times with EtOAc. The combined organic extracts were washed with water, dried over Na₂SO₄, filtered and concentrated. The crude product was purified by flash chromatography (25% MeOH in DCM) to give the title compound as a white solid (357 mg, 95.2%). LCMS: M+H⁺= 657.2.

Step 3: To a solution of 4-(1-((9-methyl-6-morpholino-2-(1-(phenylsulfonyl)-1H-indol-3-yl)-9H-purin-8-yl)methyl) piperidin-4-yl)morpholine (357 mg, 0.544 mmol) in ethanol (5 mL) was added a 1 M aqueous solution of NaOH (4 mL, 4 mmol). After 18 hours of stirring, the reaction mixture was concentrated and purified by RP-HPLC to give 104 (162 mg, 57.7%). LCMS: M+H⁺=517.3. ¹H-NMR (400 MHz, DMSO-d₆): δ 11.46 (s, 1H), 8.60 (m, 1H), 8.13 (s, 1H), 7.43 (m, 1H), 7.14 (m, 2H), 4.16 (s, 4H), 3.84, (s, 3H), 3.76 (t, 4H), 3.71 (s, 2H), 3.54 (t, 4H), 2.85 (d, 2H), 2.43 (t, 4H), 2.07 (m, 3H), 1.75 (d, 2H), 1.38 (m, 2H)

Example 13

N,N-dimethyl-1-((2-(2-methyl-1H-indol-1-yl)-4-morpholinothieno[3,2-d]pyrimidin-6-yl)methyl)piperidin-4-amine 105

A solution of 2-methylindole (0.131 g) in DMF (8 mL) was cooled to 0° C. then sodium hydride (0.06 g) added. After 15 min [1-(2-chloro-4-morpholin-4-yl-thieno[3,2-d]pyrimidin-6-ylmethyl)-piperidin-4-yl]-dimethyl-amine (0.395 g) was added. The reaction vessel was sealed and heated at 150° C. After 1 h the reaction mixture was cooled to room temperature and diluted with water. The resulting precipitate was collected by filtration then purified by chromatography (silica, 0 to 20% of a 49:1 MeOH:NH₄OH mixture in dichloromethane) to furnish the title compound (0.059 g, 12%) as a light brown solid. MS m/e 491 [M+H]⁺; ¹H NMR (300 MHz, DMSO-d₆) δ ppm 1.33-1.57 (m, 2H) 1.74 (d, J=12.43 Hz, 2H) 2.08 (t, J=10.55 Hz, 3H) 2.18 (s, 6H) 2.64 (s, 3H) 2.95 (d, J=11.30 Hz, 2H) 3.74-3.87 (m, 6H) 3.89-4.04 (m, 4H) 6.42 (s, 1H) 6.98-7.20 (m, 2H) 7.37 (s, 1H) 7.43-7.56 (m, 1H) 8.03 (d, J=7.54 Hz, 1H)

Example 14

(S)-2-(4-((2-(1H-indol-3-yl)-7-methyl-4-(3-methyl-morpholino)thieno[3,2-d]pyrimidin-6-yl)methyl) piperazin-1-yl)-2-methylpropanamide 106

Following the procedures to prepare 104, (S)-2-((4(2-chloro-7-methyl-4-(3-methylmorpholino)thieno[3,2-d]pyrimidin-6-yl)methyl)piperazin-1-yl)-2-methylpropanamide was converted to 106. LCMS: M+H⁺=548.3. ¹H-NMR (400 MHz, DMSO-d₆): δ 11.50 (s, 1H), 8.62 (m, 1H), 8.17 (s, 1H), 7.45 (m, 1H), 7.13 (m, 2H), 7.05 (s, 1H), 6.94 (s, 1H), 4.77 (m, 1H), 4.45 (d, 1H), 4.05 (d, 1H), 3.73-3.88 (m, 4H), 3.58 (m, 1H), 3.45 (m, 1H), 2.38-2.63 (m, 11H), 1.34 (d, 3H), 1.08 (s, 6H)

Example 15

2-(1-((9-(2-hydroxyethyl)-2-(1H-indol-3-yl)-6-morpholino-9H-purin-8-yl)methyl)piperidin-4-yl)propan-2-ol 107

Step 1: 2-chloro-6-morpholino-9-(tetrahydro-2H-pyran-2-yl)-9H-purine-8-carbaldehyde

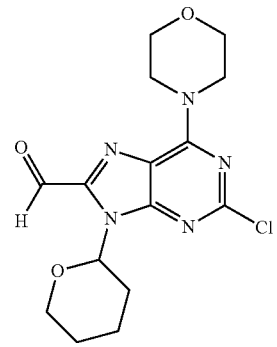

To a solution of 4-(2-chloro-9-(tetrahydro-2H-pyran-2-yl)-9H-purin-6-yl)morpholine (1.96 g, 6.05 mmol) in THF (75 mL) was a 2.5 M solution of n-BuLi in hexanes (3.2 mL, 7.9 mmol) at −78° C. The reaction mixture was then stirred at −78° C. for 45 minutes. DMF (0.94 mL, 12.1 mmol) was then added. The resulting mixture was stirred at −78° C. for 2 hours before being poured slowly onto ice. The mixture was then extracted three times with DCM. The combined extracts were washed with water, dried over sodium sulfate and concentrated. The crude product was purified by flash chromatography (25% EtOAc in heptane) to give the title compound (1.1 g, 52%). LCMS: M+H⁺=352.2.

Step 2: 2-(1-((2-chloro-6-morpholino-9-(tetrahydro-2H-pyran-2-yl)-9H-purin-8-yl)methyl)piperidin-4-yl)propan-2-ol

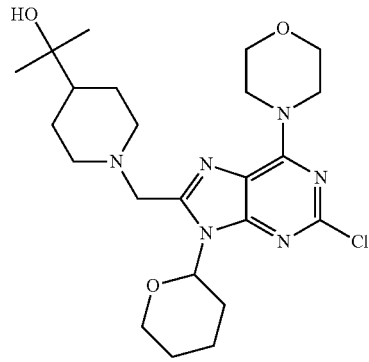

A mixture of 2-chloro-6-morpholino-9-(tetrahydro-2H-pyran-2-yl)-9H-purine-8-carbaldehyde (245 mg, 0.696 mmol), 2-(4-piperidyl)-2-propanol (110 mg, 0.77 mmol) and sodium triacetoxyborohydride (162 mg, 0.77 mmol) in 1,2-dichloroethane (10 mL) was stirred at room temperature for 30 minutes. The reaction mixture was then diluted with saturated aqueous sodium bicarbonate. The aqueous layer was then extracted with DCM. The combined organic extracts were then washed with water, dried over sodium sulfate, filtered and concentrated. The crude product was purified by flash chromatography (0-100% gradient EtOAc-heptane) to give the title compound (328 mg, 98%). LCMS: M+H+=480.2.

Step 3: 2-(2-chloro-8-((4-(2-hydroxypropan-2-yl)piperidin-1-yl)methyl)-6-morpholino-9H-purin-9-yl) ethyl acetate

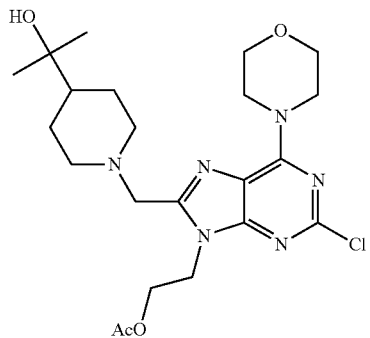

To a solution of 2-(1-((2-chloro-6-morpholino-9-(tetrahydro-2H-pyran-2-yl)-9H-purin-8-yl)methyl)piperidin-4-yl) propan-2-ol (328 mg, 0.685 mmol) in methanol (10 mL) was added concentrated HCl (0.15 mL). The resulting mixture was stirred at 50° C. for 18 hours. The reaction mixture was then concentrated to give a yellow paste which was then taken up in DMF (10 mL) and cooled to 0° C. To this cooled solution was then added sodium hydride (60% dispersion, 88 mg, 2.2 mmol). The mixture was stirred at 0° C. for 5 minutes before the addition of 2-bromoethanol acetate (0.2 mL, 1.8 mmol). After 18 hours of stirring at room temperature, the reaction was diluted with water. The aqueous mixture was the extracted three times with EtOAc. The combined extracts were washed with brine, dried over $Na_2SO_4$, filtered and concentrated. The crude product was purified by flash chromatography (10% MeOH in DCM) to give the title compound (110 mg, 26%). LCMS: M+H+=481.2.

Step 4: To a degassed suspension of 2-(2-chloro-8-((4-(2-hydroxypropan-2-yl)piperidin-1-yl)methyl)-6-morpholino-9H-purin-9-yl)ethyl acetate (110 mg, 0.23 mmol), 1-(phenylsulfonyl)-3-indoleboronic acid (83 mg, 0.27 mmol), 2 M $Na_2CO_3$ aqueous solution (0.23 mL, 0.46 mmol) in toluene (3 mL) and ethanol (1 mL) was added $Pd(PPh_3)_4$ (10 mg, 0.009 mmol). The suspension was then stirred under nitrogen at 95° C. for 18 hours. The reaction mixture was then diluted with EtOAc and water. The layers were then separated. The aqueous layer was extracted three times with EtOAc. The combined organic extracts were washed with water, dried over $Na_2SO_4$, filtered and concentrated. The crude mixture was filtered through a pad of silica gel (10% MeOH in DCM) and the filtrate was concentrated to give a yellow paste which was then taken up in ethanol (10 mL). To the solution was added a 1 M aqueous solution of NaOH (2 mL, 2 mmol). After 2 hours of stirring at 65° C., the reaction mixture was concentrated and purified by RP-HPLC to give 107 (32 mg, 40%). LCMS: M+H+=520.3. $^1$H-NMR (400 MHz, DMSO-$d_6$): δ 11.5 (s, 1H), 8.54 (m, 1H), 8.20 (s, 1H), 8.11 (d, 1H), 7.44 (m, 1H), 7.14 (m, 2H), 4.44 (t, 2H), 4.27 (s, br, 4H), 3.85 (t, 2H), 3.78 (m, 4H), 3.72 (s, 3H), 2.91 (m, 2H), 1.98 (m, 2H), 1.67 (m, 2H), 1.21 (m, 3H), 1.01 (s, 6H)

Example 16

(4-(2-(1H-indol-3-yl)-9-methyl-8-((4-(tetrahydro-2H-1,1-dioxo-thiopyran-4-yl)piperazin-1-yl)methyl)-9H-purin-6-yl)morpholine 108

Following the procedures to prepare 104, 4-tetrahydro-1, 1-dioxo-thiopyran-4-ylpiperazine was converted to 108. LCMS: M+H+=565.3. $^1$H-NMR (400 MHz, DMSO-$d_6$): δ 11.46 (s, 1H), 8.60 (m, 1H), 8.13 (s, 1H), 7.43 (m, 1H), 7.14 (m, 2H), 4.26 (s, 4H), 3.86 (s, 3H), 3.76 (m, 4H), 3.72 (s, 2H), 3.06 (m, 4H), 2.35-2.62 (m, 9H), 1.98 (m, 4H)

Example 17

1-(1-((9-ethyl-2-(5-fluoro-1H-indol-1-yl)-6-morpholino-9H-purin-8-yl)methyl)piperidin-4-yl)pyrrolidin-2-one 109

A mixture of 1-[1-(2-chloro-9-ethyl-6-morpholin-4-yl-9H-purin-8-ylmethyl)-piperidin-4-yl]-pyrrolidin-2-one (115 mg, 0.26 mmol), [1-(tert-butyldimethylsilanyl)-5-fluoro-1H-indol-4-yl]boronic acid (105 mg, 0.36 mmol), $Pd(PPh_3)_4$ (30 mg, 10 mol %) and cesium carbonate (167 mg, 0.51 mmol) in dioxane/water (5:2 mL) was purged with nitrogen gas then heated at 140° C., for 30 min, in a microwave reactor. The reaction mixture was loaded onto an Isolute® SCX-2 cartridge, washed with MeOH then eluted with 2 M $NH_3$ in MeOH. The resulting residue was purified by column chromatography (Si-PPC, MeOH:DCM, gradient 0:100 to 07:93) to give 109 as a colourless oil (13 mg, 9%). LCMS (Method F) $R_T$ 8.15 min, [M+H]+ 547.3. $^1$H NMR (CDCl$_3$, 400 MHz): δ 8.74 (dd, J=9.1, 4.8 Hz, 1H); 8.30 (d, J=3.6 Hz, 1H); 7.28-7.24 (m, 1H); 7.08-6.99 (m, 1H); 6.58 (d, J=3.6 Hz, 1H); 4.42-4.30 (m, 6H); 4.09-3.97 (m, 1H); 3.88 (t, J=4.75 Hz, 4H); 3.72 (s, 2H); 3.35 (t, J=7.0 Hz, 2H); 2.95 (d, J=11.3 Hz, 2H); 2.39 (t, J=8.1 Hz, 2H); 2.32-2.22 (m, 2H); 2.06-1.95 (m, 2H); 1.77-1.61 (m, 4H); 1.52 (t, J=7.15 Hz, 3H)

Example 18

1-((2-(1H-indol-3-yl)-9-methyl-6-morpholino-9H-purin-8-yl)methyl)-N,N-dimethylpiperidin-4-amine 110

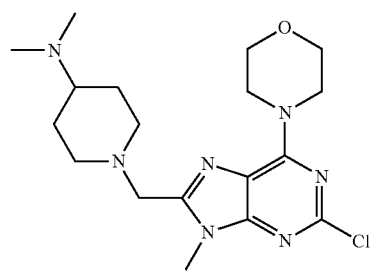

N,N-dimethylpiperidin-4-amine (0.41 g) was reacted with 4-(8-(bromomethyl)-2-chloro-9-methyl-9H-purin-6-yl)morpholine (1.0 g) via General Procedure C to yield 1-((2-chloro-9-methyl-6-morpholino-9H-purin-8-yl)methyl)-N,N-dimethylpiperidin-4-amine (0.52 g) as a white solid. This intermediate was reacted with 1-(phenylsulfonyl)-1H-indol-3-ylboronic acid via General Procedure B to give intermediate N,N-dimethyl-1-((9-methyl-6-morpholino-2-(1-(phenylsulfonyl)-1H-indol-3-yl)-9H-purin-8-yl)methyl)piperidin-4-amine. The intermediate was suspended in MeOH (3 mL) whereupon 3N KOH (0.3 mL) was added and the reaction mixture was heated at 50° C. for several hours until the protecting group was removed. Reverse phase purification gave 110. MS (Q1) 475.3 (M)+. $^1$H NMR (400 MHz, DMSO) δ 11.46 (s, 1H), 8.66-8.51 (m, 1H), 8.13 (d, 1H), 7.48-7.36 (m, 1H), 7.19-7.08 (m, 2H), 4.26 (s, 4H), 3.93 (d, 3H), 3.83-3.75 (m, 4H), 3.70 (s, 2H), 2.84 (d, 2H), 2.15 (s, 6H), 2.11-1.94 (m, 3H), 1.72 (d, 2H), 1.36 (q, 2H)

Example 19

4-(2-(1H-indol-3-yl)-9-methyl-8-((4-(tetrahydro-2H-pyran-4-yl)piperazin-1-yl)methyl)-9H-purin-6-yl)morpholine 111

Following the procedures to prepare 104, 1-(tetrahydro-2H-pyran-4-yl)piperazine was converted to 111. LCMS: M+H+=517.3. $^1$H-NMR (400 MHz, DMSO-d$_6$): δ 11.47 (s, 1H), 8.60 (m, 1H), 8.14 (d, 1H), 7.44 (m, 1H), 7.15 (m, 2H), 4.27 (m, 4H), 3.93 (m, 2H), 3.86 (s, 4H), 3.78 (m, 4H), 2.75-3.31 (s, br, 4H), 1.79-1.98 (s, br, 2H), 1.43-1.68 (s, br, 2H)

Example 20

N,N-dimethyl-1-((2-(5-methyl-1H-indol-3-yl)-4-morpholinothieno[3,2-d]pyrimidin-6-yl)methyl)piperidin-4-amine 112

A microwave vessel was charged with dimethyl-[1-(4-morpholin-4-yl-2-tributylstannanyl-thieno[3,2-d]pyrimidin-6-methyl)-piperidin-4-yl]-amine (0.4 g) in dioxane (8 mL). The vessel was evacuated and back filled with argon. To this mixture was added 3-bromo-5-methyl-indole-1-carboxylic acid tert-butyl ester (0.23 g), copper iodide (0.14 g) and tetrakistriphenylphosphine palladium (0.08 g). The vessel was evacuated and back filled with argon again, then the mixture was then irradiated with microwaves at 150° C. for 35 min. The reaction mixture was cooled to room temperature then filtered through HPLC filter. The filtrate was concentrated and the residue obtained was purified by chromatography (silica, 0 to 20% of a 49:1 MeOH:NH$_4$OH mixture in dichloromethane). The residue obtained was dissolved in anhydrous methanol and 4.0 N HCl in dioxane (6 mL) was added. The mixture was stirred at room temperature overnight and the precipitate collected by filtration then dried to yield the title compound (0.04 g, 11%) as a light yellow solid. MS m/e 491 [M+H]+. $^1$H NMR (300 MHz, DMSO-d$_6$) δ ppm 2.00 (br. s., 2H) 2.11-2.21 (m, 2H) 2.45 (s, 3H) 2.72 (s, 8H) 3.31 (br. s., 3H) 3.86-3.95 (m, 4H) 4.06-4.26 (m, 4H) 4.32 (br. s., 2H) 7.07 (dd, J=8.29, 1.51 Hz, 1H) 7.41 (d, J=8.29 Hz, 1H) 7.84 (s, 1H) 8.17 (s, 1H) 8.76 (br. s., 1H)

Example 21

2-(1-((2-(1H-indol-3-yl)-9-methyl-6-morpholino-9H-purin-8-yl)methyl)piperidin-4-yl)propan-2-ol 115

2-(1-((2-Chloro-9-methyl-6-morpholino-9H-purin-8-yl)methyl)piperidin-4-yl)propan-2-ol was reacted with 1-(phenylsulfonyl)-1H-indol-3-ylboronic acid via General Procedure B to give intermediate 2-(1-((9-methyl-6-morpholino-2-(1-(phenylsulfonyl)-1H-indol-3-yl)-9H-purin-8-yl)methyl)piperidin-4-yl)propan-2-ol. The intermediate was suspended in MeOH (3 mL) whereupon 3N KOH (0.3 mL) was added and the reaction mixture was heated at 50° C. for several hours until the protecting group was removed. Reverse phase purification gave 115. MS (Q1) 490.3 (M)+. $^1$H NMR (400 MHz, DMSO) δ 11.46 (s, 1H), 8.67-8.51 (m, 1H), 8.13 (d, 1H), 7.53-7.25 (m, 2H), 7.20-7.07 (m, 2H), 4.27 (s, 4H), 4.02 (s, 1H), 3.84 (s, 3H), 3.76 (dd, 12.2, 4H), 3.69 (s, 2H), 2.88 (d, 2H), 1.97 (t, 2H), 1.66 (d, 2H), 1.21 (dt, 3H), 1.02 (s, 6H)

Example 22

9-((2-(1H-indol-3-yl)-4-morpholinothieno[3,2-d]pyrimidin-6-yl)methyl)-1-oxa-4,9-diazaspiro[5.5]undecan-3-one 116

A degassed solution of 9-(2-chloro-4-morpholin-4-yl-thieno[3,2-d]pyrimidin-6-ylmethyl)-1-oxa-4,9-diazaspiro[5.5]undecan-3-one (150 mg, 0.34 mmol), 1-(phenylsulfonyl)-3-indoleboronic acid (155 mg, 0.51 mmol), Pd(PPh$_3$)$_4$ (40 mg, 0.035 mmol) and Cs$_2$CO$_3$ (225 mg, 0.69 mmol) in a mixture of 1,4-dioxane (6 mL) and water (3 mL) was subjected to microwave irradiation at 140° C. for 30 min. The reaction mixture was cooled to ambient temperature and loaded onto an Isolute® SCX-2 cartridge (10 g). The cartridge was then washed with MeOH and the desired product was subsequently eluted using 2 M NH$_3$ in MeOH. The eluent was collected and concentrated to give 9-[2-(1-benzenesulfonyl-1H-indol-3-yl)-4-morpholin-4-yl-thieno[3,2-d]pyrimidin-6-ylmethyl]-1-oxa-4,9-diazaspiro[5.5]undecan-3-one as a crude oil. Aqueous NaOH (12.5 M, 0.4 mL) was added to a solution of 9-[2-(1-benzenesulfonyl-1H-indol-3-yl)-4-morpholin-4-yl-thieno[3,2-d]pyrimidin-6-ylmethyl]-1-oxa-4,9-diazaspiro[5.5]undecan-3-one in 1,4-dioxane (4 mL) and IMS (4 mL). The reaction mixture was stirred at ambient temperature for 90 min, and then concentrated in vacuo. The residue was dissolved in MeOH then loaded onto an Isolute® SCX-2 cartridge (10 g). The cartridge was then washed with MeOH and the desired product was subsequently eluted using 2 M NH$_3$ in MeOH. The eluent was collected and concentrated to afford a sticky solid. The solid was purified by flash chromatography (Si-PPC, DCM: MeOH, 100:0 to 99:1 to 95:5) followed by reverse phase HPLC (Phenomenex Luna C-18, 20 mM Et$_3$N in water on a gradient of 20 mM Et$_3$N in acetonitrile 90:10 to 5:95) to afford 116 as a white solid (72 mg, 40%). LCMS: R$_T$=5.05 min, [M+H]+=519.2. $^1$H NMR (CDCl$_3$, 400 MHz): δ 8.69-8.64 (m, 1H); 8.45 (s, 1H); 8.15 (d, J=2.7 Hz, 1H); 7.44-7.40 (m, 1H); 7.30-7.22 (m, 3H); 5.91 (s, 1H); 4.17 (s, 2H); 4.08-4.03 (m, 4H); 3.94-3.89 (m, 4H); 3.85 (s, 2H); 3.26 (d, J=2.6 Hz, 2H); 2.78-2.69 (m, 2H); 2.47 (t, J=11.2 Hz, 2H); 1.96 (d, J=13.8 Hz, 2H); 1.77-1.67 (m, 2H)

Example 23

4-(5-(1H-indol-3-yl)-2-((3-morpholinoazetidin-1-yl)methyl)thiazolo[5,4-d]pyrimidin-7-yl)morpholine 117

A degassed solution of 5-chloro-7-morpholin-4-yl-2-(3-morpholin-4-yl-azetidin-1-ylmethyl)thiazolo[5,4-c]pyrimidine (210 mg, 0.51 mmol), 1-(phenylsulfonyl)-3-indoleboronic acid (231 mg, 0.77 mmol), Pd(PPh$_3$)$_4$ (60 mg, 0.052 mmol) and Cs$_2$CO$_3$ (332 mg, 1.03 mmol) in a mixture of 1,4-dioxane (8 mL) and water (4 mL) was subjected to microwave irradiation at 150° C. for 30 min. The reaction mixture was cooled to ambient temperature and loaded onto an Isolute® SCX-2 cartridge (10 g). The cartridge was then washed with MeOH and the desired product was subsequently eluted using 2 M $NH_3$ in MeOH. The eluent was collected and concentrated to give 5-(1-benzenesulfonyl-1H-indol-3-yl)-7-morpholin-4-yl-2-(3-morpholin-4-yl-azetidin-1-ylmethyl)-thiazolo[5,4-c]pyrimidine as a crude oil. Aqueous NaOH (12.5 M, 0.6 mL) was added to a solution 5-(1-benzenesulfonyl-1H-indol-3-yl)-7-morpholin-4-yl-2-(3-morpholin-4-yl-azetidin-1-ylmethyl)thiazolo[5,4-d]pyrimidine in 1,4-dioxane (6 mL) and IMS (6 mL). The reaction mixture was stirred at ambient temperature for 1 h, then concentrated in vacuo. The resultant residue was dissolved in MeOH then loaded onto an Isolute® SCX-2 cartridge (10 g). The cartridge was then washed with MeOH and the desired product was subsequently eluted using 2 M $NH_3$ in MeOH. The eluent was collected and concentrated to afford a sticky solid. The solid was purified by flash chromatography (Si-PPC, DCM: MeOH, 100:0 to 98:2 to 95:5) followed by trituration from hot MeOH to afford 117 as a tan solid (117 mg, 47%). LCMS (Method E): $R_T$=7.47 min, $[M+H]^+$ 492.2. $^1H$ NMR ($CDCl_3$, 400 MHz): δ 8.65-8.60 (m, 1H); 8.44 (s, 1H); 8.13 (d, J=2.8 Hz, 1H); 7.44-7.39 (m, 1H); 7.31-7.25 (m, 2H); 4.43 (t, J=4.6 Hz, 4H); 3.99 (s, 2H); 3.91 (t, J=4.7 Hz, 4H); 3.73 (t, J=4.5 Hz, 4H); 3.66 (t, J=5.8 Hz, 2H); 3.18-3.07 (m, 3H); 2.40-2.31 (m, 4H)

Example 24

1-((2-(7-fluoro-1H-indol-3-yl)-4-morpholinothieno [3,2-d]pyrimidin-6-yl)methyl)-N,N-dimethylpiperidin-4-amine 118

Step 1:
1-benzenesulfonyl-3-bromo-7-fluoro-1H-indole

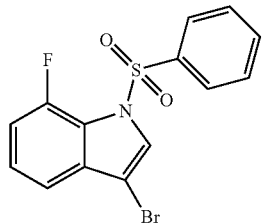

To a solution of 1-benzenesulfonyl-7-fluoro-1H-indole (1.00 g, 3.63 mmol) in $CCl_4$ (20 mL) was added a solution of saturated sodium bicarbonate (40 mL) and bromine (0.19 mL, 3.81 mmol) at room temperature. After stirring at room temperature for 16 hours, the reaction was diluted with DCM and water. The organic extract was washed with saturated sodium bicarbonate, 10% aqueous sodium thiosulfate, dried over sodium sulfate, filtered, and concentrated. The product was obtained as an off-white solid (1.22 g, 95%)

Step 2:
To a mixture of dimethyl-[1-(4-morpholin-4-yl-2-tributyl-stannanyl-thieno[3,2-d]pyrimidin-6-ylmethyl)-piperidin-4-yl]-amine (250 mg, 0.396 mmol), 1-benzenesulfonyl-3-bromo-7-fluoro-1H-indole (163 mg, 0.460 mmol), copper(I) thiophene-2-carboxylate (37 mg, 0.19 mmol), and $Pd(PPh_3)_4$ (44 mg, 0.038 mmol) was added THF (2 mL). The reaction vessel was evacuated and back filled with argon. The reaction mixture was diluted with hexane, filtered through a plug of solka floc, and the filtrate was concentrated. The residue was triturated with hexane and then purified by flash chromatography (silica, 0-10% $MeOH/NH_4OH$ (9:1) in DCM). The elutant was then concentrated to give an off-white solid which was taken up in ethanol (2 mL). A 1 M aqueous NaOH solution (0.25 mL) was then added and the resulting mixture was stirred at reflux for 2 hours. The reaction mixture was concentrated and triturated with water. The crude product was purified by flash chromatography (silica, 0-10% MeOH/$NH_4OH$ (9:1) in DCM) to give 118 as an off white solid (41.5 mg, 30%). LCMS: $M+H^+$=495. $^1H$-NMR (300 MHz, DMSO-$d_6$): δ 12.1 (s, 1H), 8.38 (d, 1H), 8.19 (d, 1H), 7.32 (s, 1H), 7.08 (m, 1H), 6.98 (m, 1H), 3.96 (m, 4H), 3.81 (m, 6H), 2.93 (d, 2H), 2.16 (s, 6H), 2.05 (t, 3H), 1.72 (d, 2H), 1.40 (m, 2H)

Example 25

1-((2-(5-fluoro-2-methyl-1H-indol-1-yl)-4-morpholinothieno[3,2-d]pyrimidin-6-yl)methyl)-N,N-dimethylpiperidin-4-amine 119

A solution of 2-methyl-5-fluoroindole (0.164 g) in DMF (6 mL) was cooled to 0° C. then sodium hydride (0.066 g) added. After 30 min [1-(2-chloro-4-morpholin-4-yl-thieno[3,2-d]pyrimidin-6-ylmethyl)-piperidin-4-yl]-dimethyl-amine (0.395 g) was added. The reaction vessel was sealed and heated at 150° C. After 3 h the reaction mixture was cooled to room temperature and diluted with water and saturated aqueous sodium chloride solution. The resulting residual oil was separated from the aqueous layer, and then purified by chromatography (silica, 0 to 20% of a 49:1 MeOH:$NH_4OH$ mixture in dichloromethane) to furnish 119 (0.053 g, 10%) as a yellow solid. MS m/e 509 $[M+H]^+$; $^1H$ NMR (300 MHz, DMSO-$d_6$) δ ppm 1.33-1.57 (m, 2H) 1.74 (d, 2H) 2.08 (t, 3H) 2.18 (s, 6H) 2.64 (s, 3H) 2.95 (d, 2H) 3.74-3.87 (m, 6H) 3.89-4.04 (m, 4H) 6.42 (s, 1H) 6.98-7.20 (m, 1H) 7.37 (m, 1H) 7.43 (s, 1H) 8.03 (m, 1H).

Example 26

1-((2-(5-fluoro-1H-indol-1-yl)-4-morpholinothieno [3,2-d]pyrimidin-6-yl)methyl)-N,N-dimethylpiperidin-4-amine 120

A solution of 5-fluoroindole (0.148 g) in DMF (6 mL) was cooled to 0° C. then sodium hydride (0.06 g) added. After 30 min [1-(2-chloro-4-morpholin-4-yl-thieno[3,2-d]pyrimidin-6-ylmethyl)-piperidin-4-yl]-dimethyl-amine (0.395 g) was added. The reaction vessel was sealed and heated at 150° C. After 3 h the reaction mixture was cooled to room temperature and diluted with water and saturated aqueous sodium chloride solution. The solid separated was filtered, and then purified by chromatography (silica, 0 to 20% of a 49:1 MeOH:$NH_4OH$ mixture in dichloromethane) to furnish 120 (0.252 g, 51%) as a off white solid. MS m/e 495 $[M+H]^+$; $^1H$ NMR (300 MHz, DMSO-$d_6$) δ ppm 1.33-1.57 (m, 2H) 1.74 (d, 2H) 2.08 (t, 3H) 2.18 (s, 6H) 2.95 (d, 2H) 3.74-3.87 (m, 6H) 3.89-4.04 (m, 4H) 6.75 (d, 1H) 7.0-7.10 (m, 1H) 7.37 (s, 1H) 7.6-7.7 (m, 1H) 8.33 (d, 1H) 8.5-8.6 (d, 1H).

Example 27

2-(2-(2-(1H-indol-3-yl)-4-morpholinothieno[3,2-d] pyrimidin-6-yl)propan-2-yloxy)-1-(pyrrolidin-1-yl) ethanone 121

To a degassed mixture of 2-methyl-2-(4-((4-morpholino-2-(tributylstannyl)thieno[3,2-d]pyrimidin-6-yl)methyl)piperazin-1-yl)propanamide (394 mg, 0.568 mmol), 4-bromo-7-fluoro-1-(phenylsulfonyl)-1H-pyrrolo[3,2-c]pyridine (168 mg, 0.473 mmol), copper(I) iodide (135 mg, 0.709 mmol) in THF (4 mL) was added Pd(PPh$_3$)$_4$ (30 mg, 0.02 mmol). The reaction mixture was reacted in the microwave at 140° C. for 30 min. The reaction mixture was then filtered through paper and concentrated. The crude product dissolved in DCM and filtered through a column of silica gel (5% MeOH in DCM). The elutant was then concentrated to give a yellow paste which was taken up in ethanol (2 mL) and 1,4-dioxane (2 mL). A 12M aqueous NaOH solution was then added and the resulting mixture was stirred at room temperature for 1 hour. The mixture was then loaded onto a Biotage Isolute SPE SCX-2 column. The column was first washed with water, MeOH, and DCM. The product was eluted with 2 M NH$_3$ in MeOH and concentrated. The crude was further purified by flash chromatography using a Biotage KP-NH column (5% MeOH in DCM) to give 121. LCMS: M+H$^+$=539.2. $^1$H-NMR (400 MHz, DMSO-d$_6$): δ 12.21 (s, 1H), 8.27 (d, 1H), 7.60 (s, 1H), 7.44 (s, 1H), 7.27 (m, 1H), 7.06 (m, 1H), 6.93 (m, 1H), 3.98 (t, 4H), 3.85 (s, 2H), 3.81 (t, 4H), 2.43-2.58 (m, 8H), 1.08 (s, 6H)

Example 28

(3R,4S)-1-((2-(1H-indol-3-yl)-9-methyl-6-morpholino-9H-purin-8-yl)methyl)-3-fluoro-N,N-dimethylpiperidin-4-amine 123

Following the procedures to prepare 104, racemic cis-3-fluoro-N,N-dimethylpiperidin-4-amine was converted to 1-((2-(1H-indol-3-yl)-9-methyl-6-morpholino-9H-purin-8-yl)methyl)-3-fluoro-N,N-dimethylpiperidin-4-amine. The enantiomers of the final product were separated by SFC to give 123. LCMS: M+H$^+$=493.2. $^1$H-NMR (400 MHz, DMSO-d$_6$): δ 11.5 (s, 1H), 8.61 (m, 1H), 8.13 (m, 1H), 7.42 (m, 1H), 7.14 (m, 2H), 4.27 (s, br, 4H), 3.85 (s, 3H), 3.79 (m, 6H), 3.04 (m, 1H), 2.91 (m, 1H), 2.05-2.29 (m, 5H), 1.59-1.84 (m, 2H), 1.17 (t, 1H)

Example 29

2-(1-((2-(6-fluoro-1H-indol-3-yl)-9-methyl-6-morpholino-9H-purin-8-yl)methyl)piperidin-4-yl)propan-2-ol 124

Step 1: 3-iodo-6-fluoroindole

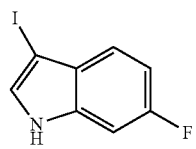

To a solution of 6-fluoroindole (1.14 g, 8.44 mmol) in DMF (20 mL) was added potassium hydroxide (0.521 g, 9.28 mmol) at 0° C. The resulting mixture was stirred at 0° C. for 10 minutes before the addition of iodine (2.57 g, 10.1 mmol). After stirring at room temperature with protection from light for 18 hours, the reaction was diluted with saturated sodium bicarbonate. The aqueous mixture was extracted three times with EtOAc. The combined organic extracts were washed with brine, dried over sodium sulfate, filtered and concentrated. The crude product was purified by flash chromatography (5% MeOH in DCM) to give 3-iodo-6-fluoroindole as a red solid (1.44 g, 65.4%).

Step 2:
6-fluoro-3-iodo-1-(phenylsulfonyl)-1H-indole

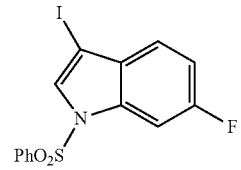

To a cooled (0° C.) solution of 3-iodo-6-fluoroindole (0.50 g, 1.92 mmol) in DMF (10 mL) was added sodium hydride (60% dispersion, 115 mg, 2.87 mmol). The resulting mixture was then stirred at 0° C. for 5 minutes before the addition of benzenesulfonyl chloride (0.37 mL, 2.9 mmol). After stirring at 0° C. for 30 minutes, the reaction was allowed to warm to room temperature and stirred at room temperature for 30 minutes. The reaction mixture was then diluted with saturated ammonium chloride. The aqueous mixture was extracted three times with EtOAc. The combined organic extracts were washed with brine, dried over sodium sulfate, filtered and concentrated. The crude product was purified by flash chromatography (0-50% gradient EtOAc-heptane) to give 6-fluoro-3-iodo-1-(phenylsulfonyl)-1H-indole (0.852 g, quant.).

Step 3: To a degassed mixture of 4-(1-((9-methyl-6-morpholino-2-(tributylstannyl)-9H-purin-8-yl)methyl)piperidin-4-yl)morpholine (200 mg, 0.3 mmol), 6-fluoro-3-iodo-1-(phenylsulfonyl)-1H-indole (75 mg, 0.187 mmol), copper(I) thiophene-2-carboxylate (36 mg, 0.19 mmol) in 1,4-dioxane (3 mL) was added Pd(PPh$_3$)$_4$ (11 mg, 0.0093 mmol). The reaction mixture was heated in the microwave at 140° C. for 30 minutes. The reaction mixture was concentrated and then dissolved in DCM and filtered through a column of silica gel (10% MeOH in DCM). The elutant was then concentrated to give a yellow paste which was taken up in ethanol (2 mL) and 1,4-dioxane (10 mL). A 1 M aqueous NaOH solution (1.0 mL) was then added and the resulting mixture was stirred at room temperature for 1 hour. The reaction mixture was then loaded onto a Biotage Isolute SPE SCX-2 column. The column was first washed with MeOH. The product was then eluted with 2 M NH$_3$ in MeOH and concentrated. The crude was further purified by RP-HPLC to give 124 (12.2 mg, 18%). LCMS: M+H$^+$=508.3. $^1$H-NMR (400 MHz, DMSO-d$_6$): δ 11.5 (s, 1H), 8.58 (m, 1H), 8.12 (s, 1H), 7.21 (m, 1H), 6.99 (m, 1H), 4.26 (s, br, 4H), 4.02 (s, 1H), 3.82 (s, 3H), 3.76 (m, 4H), 3.69 (s, 2H), 2.88 (m, 2H), 1.97 (m, 2H), 1.66 (m, 2H), 1.17 (m, 3H), 1.02 (s, 6H)

Example 30

2-(4-((2-(2-(methoxymethyl)-1H-indol-3-yl)-4-morpholinothieno[3,2-d]pyrimidin-6-yl)methyl)piperazin-1-yl)-2-methylpropanamide 126

To a degassed mixture of 2-methyl-2-(4-((4-morpholino-2-(tributylstannyl)thieno[3,2-d]pyrimidin-6-yl)methyl)piperazin-1-yl)propanamide (150 mg, 0.22 mmol), 3-bromo-2-(methoxymethyl)-1-(phenylsulfonyl)-1H-indole (82 mg, 0.22 mmol), copper(I) thiophene-2-carboxylate (41 mg, 0.22 mmol) in dioxane (2 mL) was added Pd(PPh$_3$)$_4$ (12 mg, 0.011 mmol). The reaction mixture was reacted in the microwave at 140° C. for 35 min. The reaction mixture was filtered through paper and concentrated. The crude product was purified by flash chromatography (20% MeOH in DCM) to give a yellow paste which was dissolved in dioxane (5 mL) and ethanol (1 mL). A 12 M aqueous solution of NaOH was then added. The resulting mixture was then stirred at 65° C. for 15 hours. The reaction mixture was then loaded onto a Biotage Isolute SPE SCX-2 column. The column was washed with MeOH and the desired product was then eluted with 2 M $NH_3$ in MeOH and further purified by RP-HPLC to give 126 (12.4 mg, 10.2%). LCMS: $M+H^+$=564.3. $^1$H-NMR (400 MHz, DMSO-$d_6$): δ 11.48 (s, 1H), 8.55 (m, 1H), 7.44 (m, 1H), 7.35 (s, 1H), 7.10 (m, 2H), 7.05 (m, 1H), 6.93 (m, 1H), 5.19 (s, 2H), 3.90 (m, 4H), 3.83 (m, 6H), 3.47 (s, 3H), 2.42-2.58 (m, 8H), 1.08 (s, 6H)

Example 31

2-(1-((2-(2-(methoxymethyl)-1H-indol-1-yl)-9-methyl-6-morpholino-9H-purin-8-yl)methyl)piperidin-4-yl)propan-2-ol 127

To a solution of 2-(methoxymethyl)-1H-indole (57 mg, 0.35 mmol) in DMF (2 mL) was added sodium hydride (60% dispersion, 15 mg, 0.38 mmol) at 0° C. The mixture was stirred at 0° C. for 10 minutes before the addition of 2-(1-((2-chloro-9-methyl-6-morpholino-9H-purin-8-yl)methyl)piperidin-4-yl)propan-2-ol (120 mg, 0.29 mmol). The mixture was heated in the microwave at 180° C. for 15 minutes. The reaction mixture was then diluted with water. The mixture was extracted with three times with EtOAc. The combined extracts were washed with water, dried over $Na_2SO_4$, filtered and concentrated. The crude product was then purified by flash chromatography (0-100% gradient EtOAc-heptane) followed by RP-HPLC to give 127 (29.2 mg, 19%). LCMS: $M+H^+$=534.3. $^1$H-NMR (400 MHz, DMSO-$d_6$): δ 8.18 (d, 1H), 7.57 (d, 1H), 7.20 (t, 1H), 7.12 (t, 1H), 6.66 (s, 1H), 4.98 (s, 2H), 4.25 (s, br, 4H), 4.02 (s, 1H), 3.81 (s, 3H), 3.77 (m, 4H), 3.72 (s, 2H), 2.90 (d, 2H), 1.99 (m, 2H), 1.67 (m, 2H), 1.21 (m, 3H), 1.02 (s, 6H)

Example 32

2-(4-((2-(2-cyano-1H-indol-3-yl)-4-morpholinothieno[3,2-d]pyrimidin-6-yl)methyl)piperazin-1-yl)-2-methylpropanamide 129

Following the procedures for 126, 3-bromo-2-(cyano)-1-(phenylsulfonyl)-1H-indole was converted to 129. LCMS: $M+H^+$=545.2. $^1$H-NMR (400 MHz, DMSO-$d_6$): δ 12.8 (s, 1H), 8.75 (d, 1H), 7.49 (d, 1H), 7.44 (s, 1H), 7.40 (t, 1H), 7.28 (t, 1H), 7.06 (m, 1H), 6.93 (m, 1H), 4.04 (m, 4H), 3.87 (s, 2H), 3.80 (m, 4H), 2.41-2.64 (m, 8H), 1.08 (s, 6H)

Example 33

1-(6-((4-(dimethylamino)piperidin-1-yl)methyl)-4-morpholinothieno[3,2-d]pyrimidin-2-yl)-1H-indol-5-ol 132

A solution of 5-benzyloxyindole (0.245 g) in DMF (5 mL) was cooled to 0° C. then sodium hydride (0.06 g) added. After 30 min [1-(2-chloro-4-morpholin-4-yl-thieno[3,2-d]pyrimidin-6-ylmethyl)-piperidin-4-yl]-dimethyl-amine (0.395 g) was added. The reaction vessel was sealed and heated at 150° C. After 1 h the reaction mixture was cooled to room temperature and diluted with water and saturated aqueous sodium chloride solution. The solid separated was filtered and then purified by chromatography (silica, 0 to 20% of a 49:1 MeOH:$NH_4$OH mixture in dichloromethane). The residue obtained was dissolved in ethanol (30 mL) and dichloromethane (20 mL). Palladium on carbon (10%, 40 mg) was added. The mixture was degassed and was purged with hydrogen, and continued under a hydrogen balloon overnight. The reaction mixture was filtered through solka floc. The filtrate was concentrated and purified by chromatography (silica, 0 to 20% of a 49:1 MeOH:NH4OH mixture in dichloromethane) to furnish 132 (0.012 g, 15%) as a white solid. MS m/e 493 $[M+H]^+$; $^1$H NMR (300 MHz, DMSO-$d_6$) δ ppm 1.7-1.8 (m, 2H), 2.0-2.1 (d, 2H), 2.3 (m, 3H), 2.7 (s, 6H), 2.95 (d, 2H), 3.2 (m, 2H), 3.89-4.04 (m, 10H), 6.5 (d, 1H), 6.75 (d, 1H), 6.95 (d, 1H), 7.2 (br. s, 1H), 7.4 (s, 1H), 8.2 (d, 1H), 8.5 (d, 1H).

Example 34

2-methyl-2-(4-((2-(2-methyl-1H-indol-3-yl)-4-morpholinothieno[3,2-d]pyrimidin-6-yl)methyl)piperazin-1-yl)propanamide 133

A microwave vessel was charged with 2-[4-(4-morpholin-4-yl-2-tributylstannanyl-thieno[3,2-d]pyrimidin-6-ylmethyl)-piperazin-1-yl]-isobutyramide (0.50 g) in dioxane (10 mL). The vessel was evacuated and back filled with argon. To this mixture was added 3-bromo-2-methyl-indole-1-carboxylic acid tert-butyl ester (0.30 g), copper thiocarboxylate (0.07 g) and tetrakistriphenylphosphine palladium (0.084 g). The vessel was evacuated and back filled with argon again, then the mixture was irradiated with microwaves at 150° C. for 40 min. The reaction mixture was cooled to room temperature then filtered through HPLC filter. The filtrate was concentrated and the residue obtained was purified by chromatography (silica, 0 to 10% of a 49:1 MeOH:NH4OH mixture in dichloromethane). The residue obtained was dissolved in anhydrous methanol and 4.0 N HCl in dioxane (20 mL) was added. The mixture was stirred at room temperature for 6 h followed by heating at 50° C. for 2 h. The reaction mixture was concentrated and the residue obtained was diluted with water and neutralized with saturated aqueous sodium carbonate solution. The precipitated solid was collected by filtration and the residue obtained was purified by chromatography (silica, 0 to 10% of a 49:1 MeOH:NH4OH mixture in dichloromethane) to furnish 133 (0.057 g, 15%) as a white solid. MS m/e 534 $[M+H]^+$. $^1$H NMR (300 MHz, DMSO-$d_6$) δ ppm 1.1 (s, 6H), 2.6 (app. t, 4H), 2.85 (s, 3H), 3.8 (m, 6H), 3.91 (m, 4H), 6.6-6.7 (br. s, 2H), 7.07 (m, 2H), 7.31 (m, 2H), 8.5 (m, 1H), 11.0 (s, 1H)

Example 35

2-methyl-2-(4-((4-morpholino-2-(1H-pyrrolo[2,3-c]pyridin-3-yl)thieno[3,2-d]pyrimidin-6-yl)methyl)piperazin-1-yl)propanamide 137

Step 1: 3-bromo-pyrrolo[2,3-c]pyridine-1-carboxylic acid tert-butyl ester

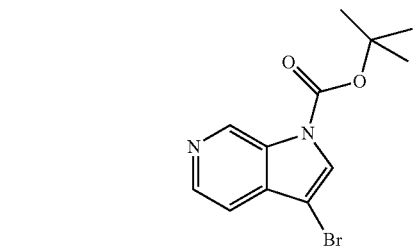

To a solution of 3-bromo-1H-pyrrolo[2,3-c]pyridine (0.500 g, 2.54 mmol) in DCM (25 mL) was added dimethyl-pyridin-4-yl-amine (3 mg, 0.02 mmol) and boc-anhydride (0.554 g, 2.54 mmol). The reaction mixture was stirred at room temperature for 20 hours. The reaction mixture was concentrated in vacuo and water was added. The solids were collected by filtration and the crude product was dissolved in ethyl acetate. The remaining fine precipitate was filtered and the filtrate concentrated to give 3-bromo-pyrrolo[2,3-c]pyridine-1-carboxylic acid tert-butyl ester as an off-white crystalline solid (0.659 g, 87%).

Step 2: To a mixture of 2-[4-(4-morpholin-4-yl-2-tributylstannanyl-thieno[3,2-d]pyrimidin-6-ylmethyl)-piperazin-1-yl]-isobutyramide (275 mg, 0.396 mmol), 3-bromo-pyrrolo[2,3-c]pyridine-1-carboxylic acid tert-butyl ester (177 mg, 0.596 mmol), copper(I) thiophene-2-carboxylate (76 mg, 0.40 mmol), and Pd(PPh$_3$)$_4$ (46 mg, 0.040 mmol) was added 1,4-dioxane (2 mL). The reaction vessel was evacuated and back filled with argon under sonication. The reaction mixture was heated in the microwave at 140° C. for 20 minutes. The reaction mixture volume was doubled with a solution of 10% MeOH in DCM. The mixture was filtered through a plug of solka floc and the filtrate was concentrated. The green residue was triturated with hexane and dried in vacuo. The light green solid was purified by flash chromatography (silica, 0-10% of a 9:1 MeOH/NH$_4$OH solution in DCM) to give 137 (20.6 mg, 10%) as an off-white solid. LCMS: M+H$^+$=521. $^1$H-NMR (300 MHz, DMSO-d$_6$): δ 12.0 (s, 1H), 8.79 (s, 1), 8.39 (d, 1H), 8.37 (d, 1H), 8.23 (d, 1H), 7.35 (s, 1H), 7.07 (d, 1H), 6.95 (d, 1H), 3.97 (m, 4H), 3.83 (m, 6), 2.55 (m, 4H), 2.46 (m, 4H), 1.08 (s, 6H)

Example 901

PI3K Isoform Inhibition Assay (p110 Alpha, Beta, Gamma, Delta: α, β, γ, δ)

PI3K enzymatic activity was assayed by measuring the amount of product phosphatidylinositol 3,4,5-phosphate (PIP3) formed from substrate 4,5 phosphatidylinositol 4,5-phosphate (PIP2) using a fluorescence polarization displacement assay. The decrease in fluorescence polarization of a fluorescent PIP$_3$ probe is measured as it is displaced from a PIP$_3$-binding protein GRP-1 detector by PI3K-catalyzed product. Assays were conducted in 384-well black Proxiplates in the presence of 10 mM Tris (pH 7.5), 50 mM NaCl, 4 mM MgCl$_2$, 5% glycerol, 25 μM ATP, 10 μM PIP$_2$ (Echelon Biosciences), 0.05% 3-[(3-cholamidopropyl)dimethylammonio]-1-propanesulfonate, 1 mM dithiothreitol, and 2% DMSO. The kinase reactions were initiated by the addition of 40 ng/mL p110α/p85α, 300 ng/mL p110β/p85α, 40 ng/mL p110γ, or 40 ng/mL p110δ/p85α (Upstate Group, Millipore; Dundee, UK), and 10 μM PIP$_2$ (Echelon Biosciences) to the wells. The reactions were stopped at timepoints that yielded a fixed change in fluorescence polarization consistent with initial rate conditions (typically 30 minutes), by the addition of 12.5 mM EDTA, 100 nM GRP-1 detector, and 5 nM tetramethylrhodamine-labeled PIP$_3$ (TAMRA-PIP$_3$; Echelon Biosciences). After 60 minutes of incubation at room temperature to allow equilibration of labeled and unlabeled PIP3 binding, the parallel and perpendicular components of the fluorescence emissions from each sample were measured at an excitation wavelength of 530 nm and an emission wavelength of 590 nm using an Envision fluorescent plate reader with a rhodamine filter (PerkinElmer Life and Analytical Sciences; Wellesley, Mass.). The assay is capable of detecting 0.1-2.0 μM PIP$_3$ product. The IC$_{50}$ values were obtained by fitting the dose-dependent inhibition data to a 4-parameter equation using Assay Explorer software (MDL, San Ramon, Calif.).

Alternatively, inhibition of PI3K was determined in a radiometric assay using purified, recombinant enzyme and ATP at a concentration of 1 uM. The Formula I compound was serially diluted in 100% DMSO. The kinase reaction was incubated for 1 h at room temperature, and the reaction was terminated by the addition of PBS. IC$_{50}$ values were subsequently determined using sigmoidal dose-response curve fit (variable slope).

The same protocol was used to establish IC$_{50}$ values for p110α (alpha) PI3K binding.

Recombinant PI3K p110 isoforms alpha, beta, and delta may be prepared and purified according to US 2008/0275067 from recombinant PI3K heterodimeric complexes consisting of a p110 catalytic subunit and a p85 regulatory subunit overexpressed using the BAC-TO-BAC® HT baculovirus expression system (GIBCO/BRL), and then purified for use in biochemical assays. The four Class I PI 3-kinases are cloned into baculovirus vectors as follows:

p110 delta: A FLAG™-tagged (Eastman Kodak Co., U.S. Pat. No. 4,703,004; U.S. Pat. No. 4,782,137; U.S. Pat. No. 4,851,341) version of human p110.delta (Chantry et al., J. Biol. Chem. (1997) 272:19236-41) is subcloned using standard recombinant DNA techniques into the BamH1-Xba1 site of the insect cell expression vector pFastbac HTb (Life Technologies, Gaithersburg, Md.), such that the clone is in frame with the His tag of the vector.

p110 alpha: Similar to the method used for p110 delta, described above, a FLAG™-tagged version of p110 alpha (Volinia et al (1994) Genomics, 24(3):427-77) was subcloned in BamH1-HindIII sites of pFastbac HTb (Life Technologies) such that the clone was in frame with the His tag of the vector.

p110 beta: A p110 beta (see Hu et al. (1993) Mol. Cell. Biol., 13:7677-88) clone was amplified from the human MARATHON™ Ready spleen cDNA library (Clontech, Palo Alto Calif.) according to the manufacturer's protocol using the specified primers.

The p110 delta binding IC50 values and delta/alpha selectivity of selected compounds from Table 1 include:

| Compound No. | p110 delta IC50 (micromolar) | IC50 p110 alpha/IC50 p110 delta |
|---|---|---|
| 101 | 0.0049 | 101 |
| 102 | 0.0208 | 34 |
| 103 | 0.0104 | 54 |
| 104 | 0.0477 | 105 |
| 113 | 0.102 | 13 |
| 116 | 0.055 | 25 |
| 117 | 0.0020 | 198 |
| 119 | 0.0236 | 68 |
| 122 | 0.0075 | 96 |
| 124 | 0.616 | >160 |
| 125 | 0.0084 | 63 |
| 127 | 0.029 | 186 |
| 129 | 0.0034 | 238 |
| 132 | 0.022 | 37 |
| 136 | 0.020 | 265 |

Example 902

Collagen Induced Arthritis Efficacy Test

The efficacy of Formula I compound inhibitors of PI3K delta to inhibit the induction and/or progression of collagen induced arthritis was tested in mice. DBA1/J male mice (Jackson Labs; 5-6 weeks of age) are acclimatized for one week and are then injected intra-dermally at the base of the tail with 0.1 ml of an emulsion of Bovine Type II Collagen (100 mg) and an equal volume of Complete Freunds Adjuvant (200 mg *Mycobacterium tuberculosis*). Three weeks later, mice are injected intra-dermally at the base of the tail with 0.1 ml of an emulsion of Bovine Type II Collagen (100 mg) and an equal volume of Incomplete Freunds Adjuvant for boost. Dosing generally starts as soon as animals display signs of joint inflammation or clinical score 1-2.

All mice are evaluated 2-3 times a week for arthritis using a macroscopic scoring system for each paw. At the end of the experiment clinical scores are obtained to evaluate the intensity of edema in the four paws. A score of 0 to 4 is assigned to each paw. Animals are scored 0 when no inflammatory signs (swelling and redness) are observed in any of the small joints (intraphalangeal, metacarpophalangeal, metatarsophalangeal) or large joints (wrist/carpus, ankle/tarsus). Animals are scored 1 when very slight to slight inflammation was observed (swelling and/or redness of paw or one digit), 2 moderate edema (swelling in two or more joint), 3 severe edema (gross swelling of the paw with more than two joints involved), and 4 when very severe edema (severe arthritis of the entire paw and digits) is present. The arthritic index for each mouse is evaluated by adding the four scores of the individual paws, giving a maximum score of 16. Plasma and serum samples are taken at 1 hour (orbital bleed) post dose and 24 hrs (cardiac puncture) post dose. Samples are stored at −20° C. until analysis. At termination, the hind paws are transected at the distal tibia, just proximal to the tarsal joint. The left and right hind paws are placed in the histology cassettes individually and fixed in 10% formalin. These paws are sent to histology dept for further process.

Materials: Bovine Type II collagen, immunization grade, 2 mg/ml (5 ml/vial) in 0.05 M acetic acid (solution), store at −20° C., from Chondrex, LLC, Seattle, Wash. Adjuvant complete H37 Ra, 6×10 ml/box, contains 1 mg/ml *Mycobacterium tuberculosis*. For use in animal immunological studies, for laboratory use, store at +4° C., from Difco Laboratories, Detroit, Mich. 48232-7058 USA. Adjuvant Incomplete H37 Ra, 6×10 ml/box: For use in animal immunological studies, for laboratory use, store at +4° C., from Difco Laboratories.

Example 903

CD69 Whole Blood Assay

Human blood is obtained from healthy volunteers, with the following restrictions: 1 week drug-free, non-smokers. Blood (approximately 20 mls to test 8 compounds) is collected by venipuncture into Vacutainer tubes with sodium heparin.

Cynomolgus monkey blood is obtained courtesy of the LAT group from monkeys not previously exposed to, or after a washout period from, chemical dosing. Additional cyno blood draws may be collected during the course of pharmacokinetic or toxicology studies. Blood (25-30 mls for naïve monkeys or 3-4 mls from monkeys on studies requiring repeated draws) is collected by venipuncture into Vacutainer tubes with sodium heparin.

Solutions of Formula I compounds at 1000 or 2000 µM in PBS (20×), are diluted by three-fold serial dilutions in 10% DMSO in PBS for a nine point dose-response curve. An aliquot of 5.5 µl of each compound is added in duplicate to a 2 ml 96-well plate; 5.5 µl of 10% DMSO in PBS is added as control and no-stimulus wells. Human whole blood-HWB (100 µl) is added to each well. After mixing the plates are incubated at 37° C., 5% $CO_2$, 100% humidity for 30 minutes. Goat F(ab')$_2$ anti-human IgM (10 µl of a 500 µg/ml solution, 50 µg/ml final) is added to each well (except the no-stimulus wells) with mixing and the plates are incubated for an additional 20 hours. At the end of the 20 hour incubation, samples are incubated with florescent labeled antibodies for 30 minutes, at 37° C., 5% $CO_2$, 100% humidity. Include induced control, unstained and single stains for compensation adjustments and initial voltage settings. Samples are then lysed with Pharmingen Lyse according to the manufacturer's instructions. Samples are then transferred to a 96 well plate suitable to be run on the AMS 96 well system on the BD Calibur FACs machine. Data acquired and Mean Fluorescence Intensity values were obtained using Cell Quest Software. Results are initially analyzed by FACS analysis software (Flow Jo). The IC50 for test compounds is defined as the concentration which decreases by 50% the percent positive of CD69 cells that are also CD20 positive stimulated by anti-IgM (average of 8 control wells, after subtraction of the average of 8 wells for the no-stimulus background). The IC50 values are calculated by ActivityBase using Xlfit version 3, equation 201.

The IC50 values of selected compounds from Table 1 in the CD69 Whole Blood Assay include:

| Compound No. | IC50 (micromolar) |
| --- | --- |
| 101 | 0.0173 |
| 102 | 1.7 |
| 104 | 0.623 |
| 117 | 0.084 |
| 119 | 0.95 |
| 122 | 0.188 |
| 127 | 0.891 |
| 136 | 4.6 |

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

The invention claimed is:

1. A compound having the structure:

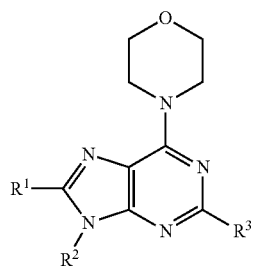

and stereoisomers, tautomers, or pharmaceutically acceptable salts thereof, wherein $R^1$ is selected from the structures:

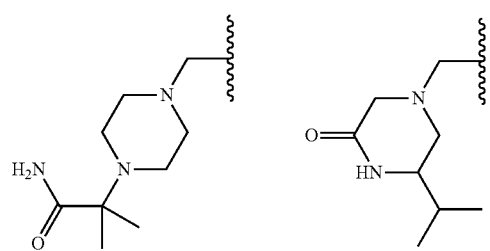
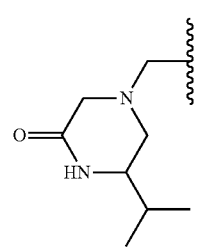
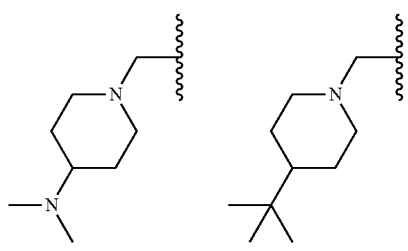
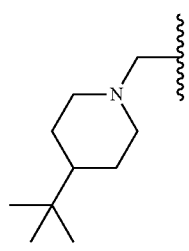
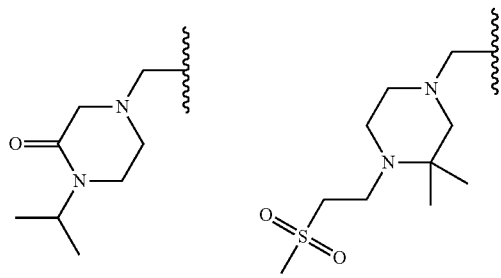
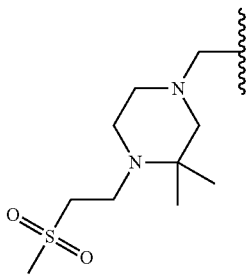
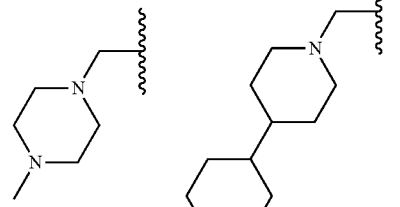
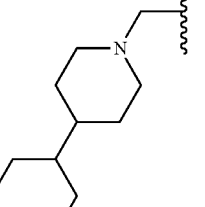
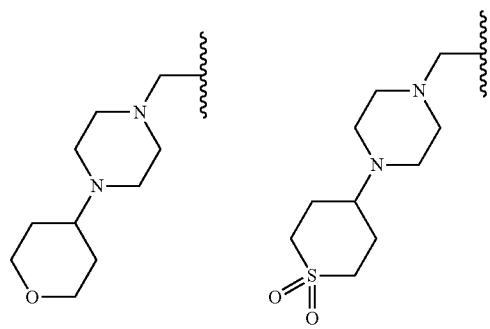
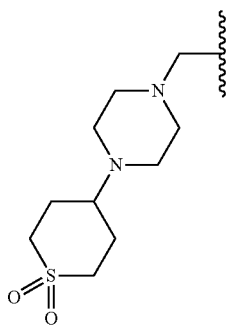
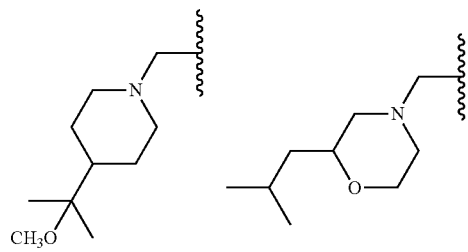
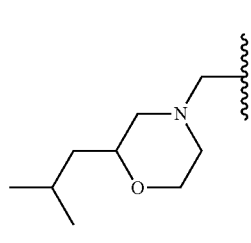
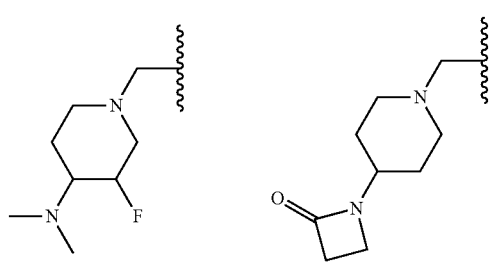
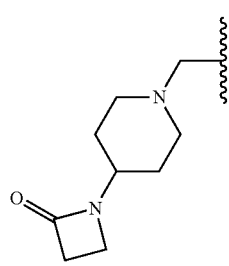
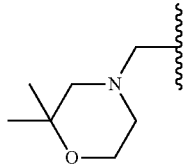
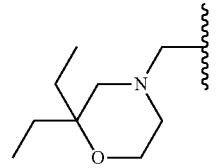
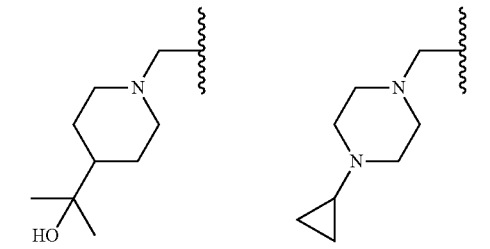
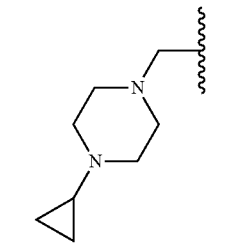
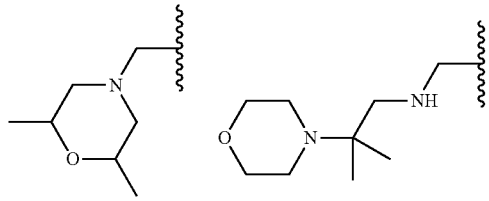
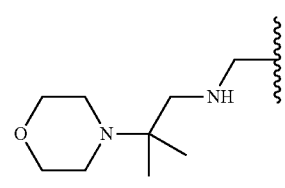
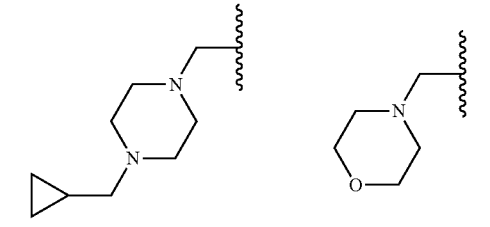
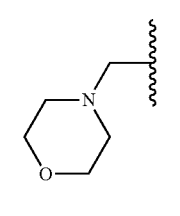
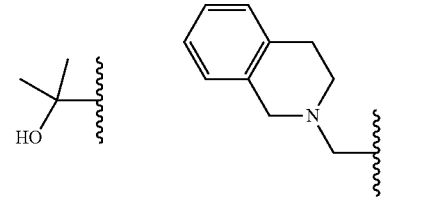
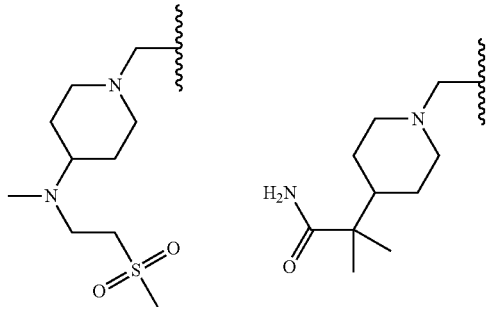

-continued

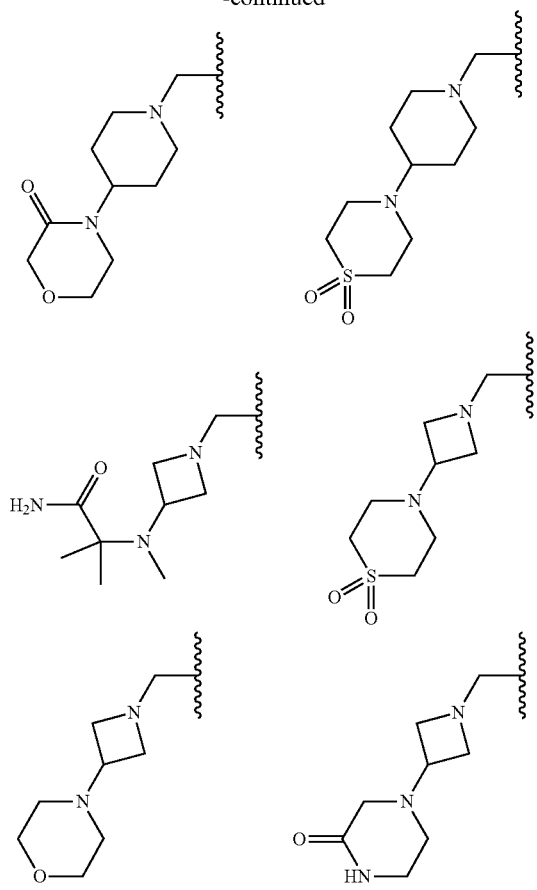

where the wavy line indicates the site of attachment;

$R^2$ is $C_1$-$C_{12}$ alkyl optionally substituted with one or more groups independently selected from F, Cl, Br, I, —CH$_3$, —CH$_2$OH, —CN, —CF$_3$, —CO$_2$H, —COCH$_3$, —CO$_2$CH$_3$, —CONH$_2$, —CONHCH$_3$, —CON(CH$_3$)$_2$, —NO$_2$, —NH$_2$, —NHCH$_3$, —NHCOCH$_3$, —NHS(O)$_2$CH$_3$, —OH, —OCH$_3$, —S(O)$_2$N(CH$_3$)$_2$, —SCH$_3$, —CH$_2$OCH$_3$, and —S(O)$_2$CH$_3$; and $R^3$ is selected from:

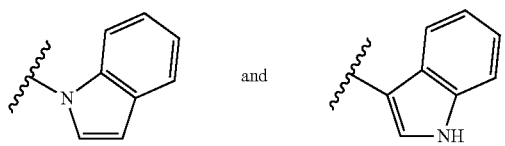

and wherein the IC50 binding activity to p110 delta is ten or more times lower than the binding activity to p110 alpha.

2. The compound of claim 1 wherein $R^2$ is CH$_3$.

3. The compound of claim 1 selected from:
4-(1-((2-(1H-indol-3-yl)-9-methyl-6-morpholino-9H-purin-8-yl)methyl)piperidin-4-yl)morpholine;
2-(1-((9-(2-hydroxyethyl)-2-(1H-indol-3-yl)-6-morpholino-9H-purin-8-yl)methyl)piperidin-4-yl)propan-2-ol;
4-(2-(1H-indol-3-yl)-9-methyl-8-((4-(tetrahydro-2H-1,1-dioxo-thiopyran-4-yl)piperazin-1-yl)methyl)-9H-purin-6-yl)morpholine;
1-(1-((9-ethyl-2-(5-fluoro-1H-indol-1-yl)-6-morpholino-9H-purin-8-yl)methyl)piperidin-4-yl)pyrrolidin-2-one;
1-((2-(1H-indol-3-yl)-9-methyl-6-morpholino-9H-purin-8-yl)methyl)-N,N-dimethylpiperidin-4-amine;
4-(2-(1H-indol-3-yl)-9-methyl-8-((4-(tetrahydro-2H-pyran-4-yl)piperazin-1-yl)methyl)-9H-purin-6-yl)morpholine;
2-(1-((2-(1H-indol-3-yl)-9-methyl-6-morpholino-9H-purin-8-yl)methyl)piperidin-4-yl)propan-2-ol;
(3S,4R)-1-((2-(1H-indol-3-yl)-9-methyl-6-morpholino-9H-purin-8-yl)methyl)-3-fluoro-N,N-dimethylpiperidin-4-amine;
(3R,4S)-1-((2-(1H-indol-3-yl)-9-methyl-6-morpholino-9H-purin-8-yl)methyl)-3-fluoro-N,N-dimethylpiperidin-4-amine;
2-(1-((2-(6-fluoro-1H-indol-3-yl)-9-methyl-6-morpholino-9H-purin-8-yl)methyl)piperidin-4-yl)propan-2-ol;
2-(1-((2-(2-(methoxymethyl)-1H-indol-1-yl)-9-methyl-6-morpholino-9H-purin-8-yl)methyl)piperidin-4-yl)propan-2-ol;
2-(1-((9-methyl-2-(2-methyl-1H-indol-1-yl)-6-morpholino-9H-purin-8-yl)methyl)piperidin-4-yl)propan-2-ol;
4-(2-(1H-indol-3-yl)-8-((4-(2-methoxypropan-2-yl)piperidin-1-yl)methyl)-9-methyl-9H-purin-6-yl)morpholine;
4-(8-((4-(2-methoxypropan-2-yl)piperidin-1-yl)methyl)-9-methyl-2-(2-methyl-1H-indol-1-yl)-9H-purin-6-yl) morpholine;
3-(8-((4-(2-hydroxypropan-2-yl)piperidin-1-yl)methyl)-9-methyl-6-morpholino-9H-purin-2-yl)-1H-indole-2-carbonitrile; and
1-(8-((4-(2-hydroxypropan-2-yl)piperidin-1-yl)methyl)-9-methyl-6-morpholino-9H-purin-2-yl)-1H-indole-2-carbonitrile.

4. A pharmaceutical composition comprised of a compound of claim 1, and a pharmaceutically acceptable carrier, glidant, diluent, or excipient.

5. The pharmaceutical composition according to claim 4, further comprising a chemotherapeutic agent.

6. A process for making a pharmaceutical composition which comprises combining a compound of claim 1 with a pharmaceutically acceptable carrier, glidant, diluent, or excipient.

7. A kit comprising:
a) a first pharmaceutical composition comprising a compound of claim 1; and
b) instructions for use.

* * * * *